(12) United States Patent
Ono et al.

(10) Patent No.: US 8,173,651 B2
(45) Date of Patent: May 8, 2012

(54) PYRIDINE COMPOUNDS

(75) Inventors: Mitsunori Ono, Lexington, MA (US); Lijun Sun, Harvard, MA (US); Yumiko Wada, Billerica, MA (US); Teresa Przewloka, Tewksbury, MA (US); Hao Li, Acton, MA (US); Howard P. Ng, Belmont, MA (US); Zachary Demko, Somerville, MA (US)

(73) Assignee: Synta Pharmaceuticals Corporation, Lexington, MA (US)

(*) Notice: Subject to any disclaimer, the term of this patent is extended or adjusted under 35 U.S.C. 154(b) by 0 days.

(21) Appl. No.: 12/722,066

(22) Filed: Mar. 11, 2010

(65) Prior Publication Data

US 2010/0173413 A1 Jul. 8, 2010

Related U.S. Application Data

(62) Division of application No. 12/041,662, filed on Mar. 3, 2008, now Pat. No. 7,687,498, which is a division of application No. 10/985,696, filed on Nov. 10, 2004, now Pat. No. 7,338,951.

(60) Provisional application No. 60/518,791, filed on Nov. 10, 2003, provisional application No. 60/585,124, filed on Jul. 1, 2004.

(51) Int. Cl.
*A61K 31/5377* (2006.01)

(52) U.S. Cl. ............ 514/235.5; 514/231.2; 514/231.5

(58) Field of Classification Search .............. 514/231.2, 514/231.5, 235.5
See application file for complete search history.

(56) References Cited

U.S. PATENT DOCUMENTS

| | | |
|---|---|---|
| 6,384,032 B1 | 5/2002 | Ono et al. |
| 6,479,510 B2 | 11/2002 | Myers et al. |
| 6,479,951 B2 | 11/2002 | Takekawa et al. |
| 6,660,733 B2 | 12/2003 | Sun et al. |
| 6,680,315 B2 | 1/2004 | Ono et al. |
| 6,693,097 B2 | 2/2004 | Ono et al. |
| 6,858,606 B2 | 2/2005 | Sun et al. |
| 6,958,332 B2 | 10/2005 | Sun et al. |
| 7,045,517 B2 | 5/2006 | Ono et al. |
| 7,067,514 B2 | 6/2006 | Ono et al. |
| 7,338,951 B2 | 3/2008 | Ono et al. |
| 2005/0250787 A1 | 11/2005 | Sun et al. |
| 2005/0282809 A1 | 12/2005 | Ono et al. |
| 2006/0025409 A1 | 2/2006 | Ono et al. |
| 2006/0030560 A1 | 2/2006 | Sun et al. |

FOREIGN PATENT DOCUMENTS

| | | |
|---|---|---|
| JP | S49-62477 | 6/1974 |
| JP | S53-44588 | 4/1978 |
| JP | S61-171469 | 8/1986 |
| JP | 2003-502424 | 1/2003 |
| WO | WO-00/62778 | 10/2000 |
| WO | WO-02/12238 | 2/2002 |
| WO | WO-02/22601 | 3/2002 |
| WO | WO-03/018586 | 3/2003 |
| WO | WO-03/047516 | 6/2003 |
| WO | WO-2004/085388 | 10/2004 |
| WO | WO-2005/016918 | 2/2005 |

OTHER PUBLICATIONS

"Alzheimer's diseases." (URL: <http://www.cnn.com/HEALTH/mentalhealth/alzheimers/#>) Jul. 2, 2011.*
Notice of Reasons for Rejection in related Japanese application JP2006-539795, dated Nov. 2, 2010 (translation included).
Nishigaki et al., "Synthesis of Iminodipyrimidines," Tetrahedron Letters. 7:539-542 (1969).
Stella, Expert Opinion of Therapeutic Patents, "Prodrugs as therapeutics", 14(3): 277-280 (2004).
Wolff et al., Burger's Medicinal Chemistry, 5th Ed., vol. 1, pp. 975-977 (1994).
Testa, Biochemical Pharmacology, "Prodrug Research: futile or fertile?" 68:2097-2106 (2004).
Ettmayer, Medicinal Chemistry, "Lessons Learned from Marketed and Investigational Prodrugs", 47(10) 2394-2404 (2004).
Morissette et al., Advanced Drug Delivery Reviews 56, 275-300 (2004).
Vippagunta et al., abstract, Vippagunta, Sudha R. "Crystalline Solids" Advanced Drug Delivery Reviews 48:3-26 (2001).
International Search Report Written Opinion from corresponding PCT Application No. PCT/USO4/37476, 2004.

* cited by examiner

*Primary Examiner* — Rebecca Anderson
*Assistant Examiner* — Samantha Shterengarts
(74) *Attorney, Agent, or Firm* — Edwards Wildman Palmer LLP; Jeffrey D. Hsi; Weiying Yang

(57) ABSTRACT

This invention features compounds of formula (I):

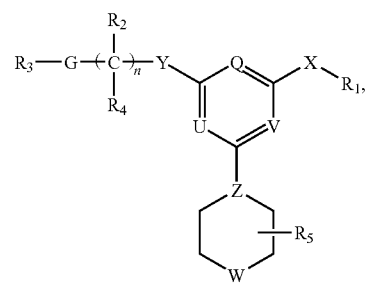

pharmaceutical compositions of the compounds, and methods of using the compounds for the treatment of, inter alia, IL-12-related diseases and disorders.

11 Claims, 1 Drawing Sheet

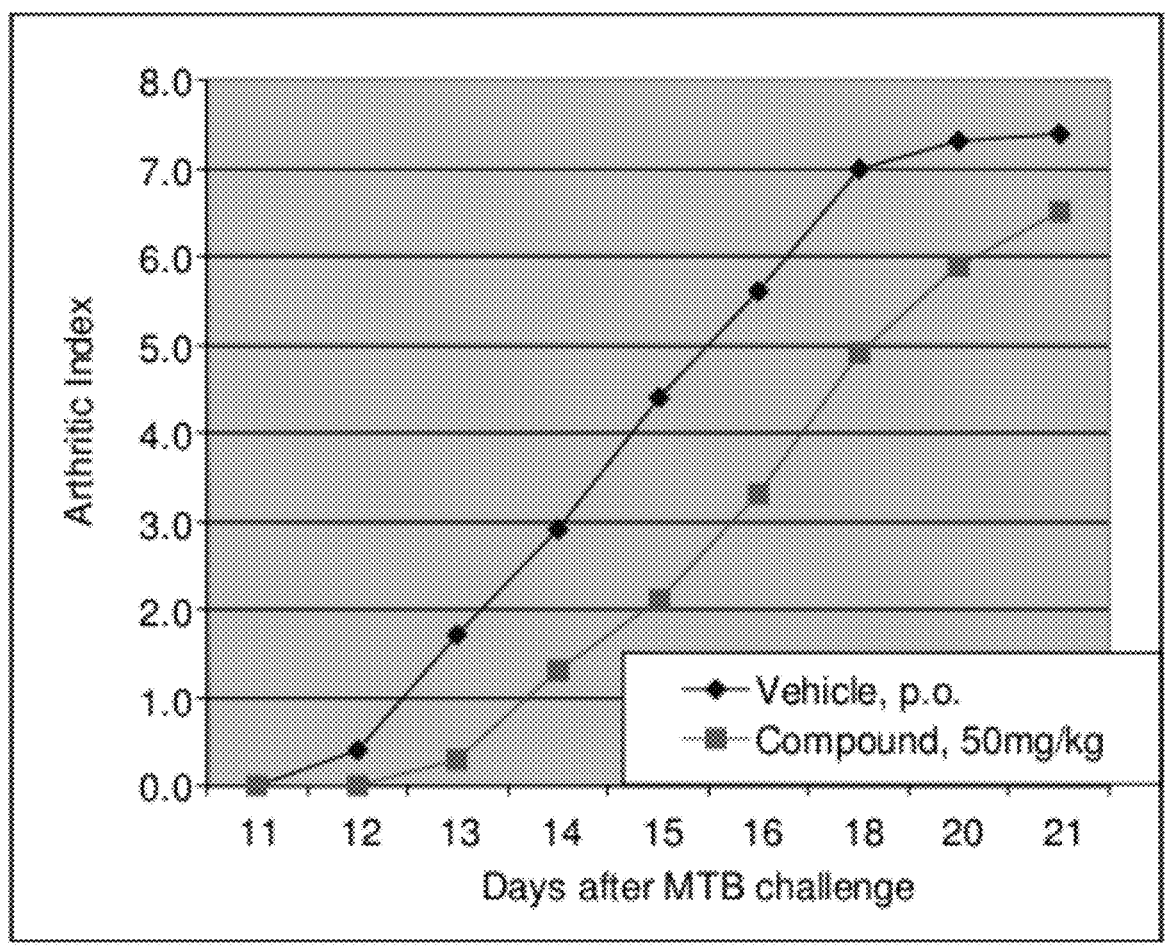

PYRIDINE COMPOUNDS

RELATED APPLICATIONS

This application is a divisional of U.S. patent application Ser. No. 12/041,662, filed Mar. 3, 2008, now allowed, which is a divisional application of U.S. patent application Ser. No. 10/985,696, filed Nov. 10, 2004, now U.S. Pat. No. 7,338,951, which claims the benefit of U.S. Provisional Patent Application Nos. 60/518,791, filed Nov. 10, 2003, and 60/585,124, filed Jul. 1, 2004. The contents of each of these applications are hereby incorporated by reference in their entirety.

BACKGROUND

Interleukin-12 (IL-12) is a heterodimeric cytokine (p70) which plays key roles in immune responses by bridging innate resistance and antigen-specific adaptive immunity. Trinchieri (1993) *Immunol Today* 14: 335. For example, it promotes type 1 T helper cell ($T_H1$) responses and, hence, cell-mediated immunity. Chan et al. (1991) *J Exp Med* 173: 869; Seder et al. (1993) *Proc Natl Acad Sci USA* 90: 10188; Manetti et al. (1993) *J Exp Med* 177: 1199; and Hsieh et al. (1993) *Science* 260: 547. Interleukin-12 (IL-12) is a di-sulfide linked heterodimeric cytokine (p70) composed of two independently regulated subunits, p35 and p40. IL-12 is produced by phagocytic cells and antigen presenting cells, in particular, macrophages and dendritic cells, upon stimulation with bacteria, bacterial products such as lipopolysaccharide (LPS), and intracellular parasites. The well-documented biological functions of IL-12 are induction of interferon-γ expression from T and NK cells and differentiation toward the $T_H1$ T lymphocyte type. IFN-γ, expression of which is induced by IL-12, is a strong and selective enhancer of IL-12 production from monocytes and macrophages. The cytokine IL-23 is a heterodimer composed of a p19 subunit and the same p40 subunit of IL-12. IL-23, similarly to IL-12, is involved in type 1 immune defenses and induces IFN-γ secretion from T cells. IL-27 is formed by the association of EBI3, a polypeptide related to the p40 subunit of IL-12, and p28, a protein related to the p35 subunit of IL-12. IL-27 promotes the growth of T cells and is thought to play a role in the differentiation of $T_H1$ cells. Pflanz et al., *Immunity* (2002), 16:779-790.

It has been suggested that, particularly in chronic diseases in which there is ongoing production of IFN-γ, IL-12 production is augmented by IFN-γ. It is presumed that after an infective or inflammatory stimulus that provokes IL-12 production, the powerful feedback loop promotes IL-12- and IL-23-induced IFN-γ to further augment IL-12 production, leading to consequent excessive production of pro-inflammatory cytokines. Furthermore, it has been suggested that IL-27 induces the expression of T-bet, a major $T_H1$-specific transcription factor, and it's downstream target IL-12R β2, independently of IFN-γ. In addition, IL-27 suppresses the expression of GATA-3. GATA-3 inhibits $T_H1$ development and causes loss of IL-12 signaling through suppression of IL-12R β2 and Stat4 expression. Lucas et al., PNAS (2003), 100: 15047-15052.

IL-12 plays a critical role in multiple-$T_H1$ dominant autoimmune diseases including, but not limited to, multiple sclerosis, sepsis, myasthenia gravis, autoimmune neuropathies, Guillain-Barrésyndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease. See, for example, Gately et al. (1998) *Annu Rev Immunol*. 16: 495; and Abbas et al. (1996) *Nature* 383: 787.

Inhibiting IL-12 overproduction, or inhibiting the production of cytokines such as IL-23 and IL-27 which promote IL-12 production and/or $T_H1$ development is an approach to treating the just-mentioned diseases. Trembleau et al. (1995) *Immunol. Today* 16: 383; and Adorini et al. (1997) *Chem. Immunol.* 68: 175. For example, overproduction of IL-12 and the resultant excessive $T_H1$ type responses can be suppressed by modulating IL-12, IL-23 and/or IL-27 production. Therefore, compounds that down-regulate IL-12, IL-23 and/or IL-27 production can be used for treating inflammatory diseases. Ma et al. (1998) *Eur Cytokine Netw* 9: 54.

SUMMARY OF THE INVENTION

In one aspect, the invention features a compound of formula (I):

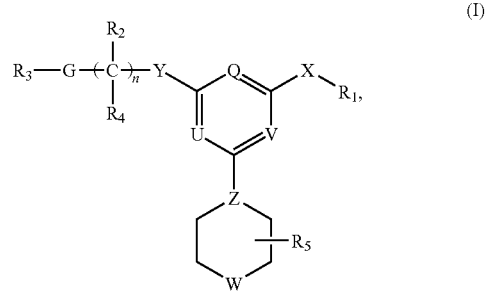

or a pharmaceutically acceptable salt, solvate, clathrate, hydrate, polymorph or prodrug thereof. In formula (I):

$R_1$ is

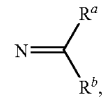

optionally substituted aryl, or optionally substituted heteroaryl;

$R_2$ and $R_4$ are, independently, H, an optionally substituted alkyl, an optionally substituted alkylcarbonyl, —$OR^k$, —$SR^k$, —$NR^hR^j$, hydroxylalkyl, —C(O)$R^c$, —OC(O)$R^c$, —SC(O)$R^c$, —$NR^kC(O)R^c$, —C(S)$R^c$, —OC(S)$R^c$, —SC(S)$R^c$, —$NR^kC(S)R^c$, —C(NR)$R^c$, —OC(NR)$R^c$, —SC(NR)$R^c$, —$NR^kC(NR)R^c$, —$SO_2R^c$, —S(O)$R^c$, —$NR^kSO_2R^c$, —OS(O)$_2R^c$, —OP(O)$R^cR^c$, —P(O)$R^cR^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or $R_2$ and $R_4$ taken together are =O, =S, or =NR;

$R_3$ is $R^g$, —C(O)$R^c$, —OC(O)$R^c$, —SC(O)$R^c$, —N$R^k$C(O)$R^c$, —C(S)$R^c$, —OC(S)$R^c$, —SC(S)$R^c$, —N$R^k$C(S)$R^c$, —C(NR)$R^c$, —OC(NR)$R^c$, —SC(NR)$R^c$, —N$R^k$C(NR)$R^c$, —SO$_2R^c$, —S(O)$R^c$, —N$R^k$SO$_2R^c$, —OS(O)$_2R^c$, —OP(O)$R^cR^c$, or —P(O)$R^cR^c$;

$R_5$ is —H, alkyl, alkylcarbonyl, halo, nitro, nitroso, cyano, azido, isothionitro, —O$R^p$ or —S$R^p$; and $R^p$ is —H, alkyl, or alkylcarbonyl; n, for each occurrence, is independently 0, 1, 2, 3, 4, 5, 6 or 7; X is O, S, S(O), S(O)$_2$, or N$R^k$; Y is (CH($R^g$))$_m$, C(O), C(NR), O, S, S(O), S(O)$_2$, N($R^k$), or absent; Z is N or CH; W is O, S, S(O), S(O)$_2$, N$R^m$, or NC(O)$R^m$, wherein $R^m$ is H, alkyl, aryl, heteroaryl, cycloalkyl, heterocycloalkyl, or alkylcarbonyl.

Furthermore, in formula (I), G is: Hydrazide; Hydrazone; Hydrazine; Hydroxylamine; Oxime; Amide; Ester; Carbonate; Carbamate; Thiocarbamate; —N$R^k$—C(NR)—N$R^k$—; —N$R^k$—C(O)—N$R^k$—; —N$R^k$—C(S)—N$R^k$—; —N$R^k$—S(O)$_2$—N$R^k$—; Phosphoryl; optionally substituted -Cyclyl-; optionally substituted -Heterocyclyl-; optionally substituted -Aryl-; optionally substituted -Heteroaryl-; optionally substituted -Heteroarylalkyl-; optionally substituted -Heteroaryl-N$R^k$—; optionally substituted -Heteroaryl-S—; optionally substituted -Heteroarylalkyl-O—; —Si(O$R^k$)$_2$—; —B(O$R^k$)—; —C(NR)—N$R^k$—; —N($R^k$)—C$R^gR^g$—C(O)—; —C(O)—ON($R^k$)—; —C(O)—N($R^k$)O—; —C(S)—ON($R^k$)—; —C(S)—N($R^k$)O—; —C(N($R^k$))—ON($R^k$)—; —C(N($R^k$))—N$R^k$O—; —OS(O)$_2$—N($R^k$)N($R^k$)—; —OC(O)—N($R^k$)N($R^k$)—; —OC(S)—N($R^k$)N($R^k$)—; —OC(N($R^k$))—N($R^k$)N($R^k$)—; —N($R^k$)N($R^k$)S(O)$_2$O—; —N($R^k$)N($R^k$)C(S)O—; —N($R^k$)N($R^k$)C(N($R^k$))O—; —OP(O)($R^c$)O—; —N($R^k$)P(O)($R^c$)O—; —OP(O)($R^c$)N($R^k$)—; —($R^k$)P(O)($R^c$)N($R^k$)—; —P(O)($R^c$)O—; —P(O)($R^c$)N($R^k$)—; —N($R^k$)P(O)($R^c$)—; —OP(O)($R^c$)—; —O-alkyl-heterocyclyl-N($R^k$)—; —N($R^k$)CH$R^g$C(O)N($R^k$)CH$R^g$C(O)—; —N($R^k$)CH$R^g$C(O)—; —N($R^k$)C(O)CH$R^g$—; —C(O)N($R^k$)CH$R^g$C(O)—; each of which is optionally substituted; or G is absent; and one of Q, U and V is N, and the other two are each C$R^g$ and each C$R^g$ may be the same or different.

Further, in formula (I), R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, —C(O)$R^c$, —O$R^k$, —S$R^k$, —N$R^hR^j$, hydroxylalkyl, nitro, cyano, haloalkyl, aminoalkyl, or —S(O)$_2R^c$; each of $R^a$ and $R^b$, independently, is H, optionally substituted alkyl, an optionally substituted cycloalkyl, an optionally substituted cyclyl, an optionally substituted heterocycloalkyl, an optionally substituted heterocyclyl, optionally substituted aryl, or optionally substituted heteroaryl; $R^c$ and $R^d$, for each occurrence, are independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —O$R^k$, —S$R^k$, —N$R^hR^j$, hydroxylalkyl, alkylcarbonylalkyl, mercaptoalkyl, aminoalkyl, sulfonylalkyl, sulfonylaryl, or thioalkoxy; $R^f$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, —C(O)$R^c$, —C(S)$R^c$, —C(NR)$R^c$, —S(O)$R^c$, —S(O)$_2R^c$, —P(O)$R^cR^c$, or —P(S)$R^cR^c$; $R^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —O$R^k$, —S$R^k$, —N$R^hR^j$, hydroxylalkyl, alkylcarbonylalkyl, mercaptoalkyl, aminoalkyl, sulfonylalkyl, sulfonylaryl, thioalkoxy, —C(O)$R^c$, —OC(O)$R^c$, —SC(O)$R^c$, —N$R^k$C(O)$R^c$, —C(S)$R^c$, —OC(S)$R^c$, —SC(S)$R^c$, —N$R^k$C(S)$R^c$, —C(NR)$R^c$, —OC(NR)$R^c$, —SC(NR)$R^c$, —N$R^k$C(NR)$R^c$, —SO$_2R^c$, —S(O)$R^c$, —N$R^k$SO$_2R^c$, —OS(O)$_2R^c$, —OP(O)$R^cR^c$, —P(O)$R^cR^c$, halo, aminoalkyl, mercaptoalkyl, cyano, nitro, nitroso, or azide; $R^h$ and $R^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or $R^h$ and $R^j$ taken together with the N to which they are attached is an optionally substituted heterocyclyl, an optionally substituted heterocycloalkyl, or an optionally substituted heteroaryl; and $R^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl.

In another aspect, this invention features a pharmaceutical composition that includes a pharmaceutically acceptable carrier and at least one of the heteroaryl compounds of this invention (e.g., a compound of formula (I) herein; any compound delineated herein).

In another aspect, the present invention features a method of inhibiting the production of IL-12 and/or inhibiting the production of a cytokine that stimulates or otherwise augments the production of IL-12 (e.g., IL-23 and IL-27) and/or inhibits the proliferation of $T_H1$ lymphocytes in a subject by administering to the subject an effective amount of a compound represented by formula (I) (or any of the formulae herein) or a pharmaceutically acceptable salt, solvate, clathrate, hydrate, polymorph, or prodrug thereof.

In another aspect, the invention features a method of inhibiting the production and/or development of $T_H1$ cells in a subject by administering to the subject an effective amount of a compound of formula (I) (or any of the formulae herein) or a pharmaceutically acceptable salt, solvate, clathrate, hydrate, polymorph, or prodrug thereof.

In another aspect, the present invention features a method for treating an IL-12 overproduction-related disorder (e.g., multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease). The method includes administering to a subject (e.g., a human or an animal) in need thereof an effective amount of one or more heteroaryl compounds of this invention. The method can also include the step of identifying a subject in need of treatment of diseases or disorders described above. The identification can be in the judgment of a subject or a health professional and can be subjective (e.g., opinion) or objective (e.g., measurable by a test or a diagnostic method).

The methods herein also include those wherein the subject administered the compound or composition herein is treated, including as identified as being treated for an IL-12 overproduction disorder.

Also within the scope of this invention are compositions containing one or more of the compounds described above for use in treating an IL-12 overproduction-related disorder, and the use of such a composition for the manufacture of a medicament for the just-described use.

Other features, objects, and advantages of the invention will be apparent from the description and from the claims.

DESCRIPTION OF THE DRAWINGS

FIG. 1 is a graph showing the effect of a compound of the invention in an in vivo arthritis model.

DETAILED DESCRIPTION OF THE INVENTION

In one aspect, the invention provides a compound of Formula (I):

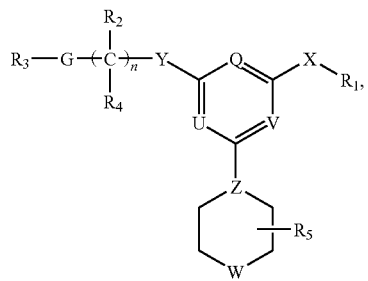

or a pharmaceutically acceptable salt, solvate, clathrate, hydrate, polymorph or prodrug thereof. In formula (I):
$R_1$ is

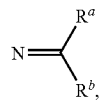

optionally substituted aryl, or optionally substituted heteroaryl;

$R_2$ and $R_4$ are, independently, H, an optionally substituted alkyl, an optionally substituted alkylcarbonyl, —$OR^k$, —$SR^k$, —$NR^hR^j$, hydroxyalkyl, —$C(O)R^c$, —$OC(O)R^c$, —$SC(O)R^c$, —$NR^kC(O)R^c$, —$C(S)R^c$, —$OC(S)R^c$, —$SC(S)R^c$, —$NR^kC(S)R^c$, —$C(NR)R^c$, —$OC(NR)R^c$, —$SC(NR)R^c$, —$NR^kC(NR)R^c$, —$SO_2R^c$, —$S(O)R^c$, —$NR^kSO_2R^c$, —$OS(O)_2R^c$, —$OP(O)R^cR^c$, —$P(O)R^cR^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or $R_2$ and $R_4$ taken together are =O, =S, or =NR;

$R_3$ is $R^g$, —$C(O)R^c$, —$OC(O)R^c$, —$SC(O)R^c$, —$NR^kC(O)R^c$, —$C(S)R^c$, —$OC(S)R^c$, —$SC(S)R^c$, —$NR^kC(S)R^c$, —$C(NR)R^c$, —$OC(NR)R^c$, —$SC(NR)R^c$, —$NR^kC(NR)R^c$, —$SO_2R^c$, —$S(O)R^c$, —$NR^kSO_2R^c$, —$OS(O)_2R^c$, —$OP(O)R^cR^c$, or —$P(O)R^cR^c$;

$R_5$ is —H, alkyl, alkylcarbonyl, halo, nitro, nitroso, cyano, azido, isothionitro, —$OR^p$ or —$SR^p$; and $R^p$ is —H, alkyl, or alkylcarbonyl; n, for each occurrence, is independently 0, 1, 2, 3, 4, 5, 6 or 7; X is O, S, S(O), S(O)$_2$, or $NR^k$; Y is $(CH(R^g))_m$, C(O), C(NR), O, S, S(O), S(O)$_2$, $N(R^k)$, or absent; Z is N or CH; W is O, S, S(O), S(O)$_2$, $NR^m$, or $NC(O)R^m$, wherein $R^m$ is H, alkyl, aryl, heteroaryl, cycloalkyl, heterocycloalkyl, or alkylcarbonyl.

Furthermore, in formula (I), G is: Hydrazide (e.g., —C(O)NHN($R^k$)— or —N($R^k$)NHC(O)—); Hydrazone (e.g., —C($R^g$)=N—N($R^k$)— or >C=N—NR$^h$R$^j$ or —N($R^k$)—N=C($R^g$)—); Hydrazine (e.g., —N($R^k$)—N($R^k$)—); Hydroxylamine (i.e., —N(OH)—); Oxime (i.e., —C(N—OH)—); Amide; Ester; Carbonate (—OC(O)O—); Carbamate (e.g., —OC(O)N($R^k$)— or —N($R^k$)C(O)O—); Thiocarbamate (e.g., —OC(S)N($R^k$)— or —N($R^k$)C(S)O— or —SC(O)N($R^k$)— or —N($R^k$)C(O)S—); —$NR^k$—C(NR)—$NR^k$—; —$NR^k$—C(O)—$NR^k$—; —$NR^k$—C(S)—$NR^k$—; —$NR^k$—S(O)$_2$—$NR^k$—; Phosphoryl; optionally substituted -Cyclyl-; optionally substituted -Heterocyclyl-; optionally substituted -Aryl-; optionally substituted -Heteroaryl-; optionally substituted -Heteroarylalkyl-; optionally substituted -Heteroaryl-$NR^k$—; optionally substituted -Heteroaryl-S—; optionally substituted -Heteroarylalkyl-O—; —Si(O$R^k$)$_2$—; —B(O$R^k$)—; —C(NR)—$NR^k$—; —N($R^k$)—C$R^g$R$^g$—C(O)—; —C(O)—ON($R^k$)—; —C(O)—N($R^k$)O—; —C(S)—ON($R^k$)—; —C(S)—N($R^k$)O—; —C(N($R^k$))—ON($R^k$)—; —C(N($R^k$))—$NR^k$O—; —OS(O)$_2$—N($R^k$)N($R^k$)—; —OC(O)—N($R^k$)N($R^k$)—; —OC(S)—N($R^k$)N($R^k$)—; —OC(N($R^k$))—N($R^k$)N($R^k$)—; —N($R^k$)N($R^k$)S(O)$_2$O—; —N($R^k$)N($R^k$)C(S)O—; —N($R^k$)N($R^k$)C(N($R^k$))O—; —OP(O)($R^c$)O—; —N($R^k$)P(O)($R^c$)O—; —OP(O)($R^c$)N($R^k$)—; —($R^k$)P(O)($R^c$)N($R^k$)—; —P(O)($R^c$)O—; —P(O)($R^c$)N($R^k$)—; —N($R^k$)P(O)($R^c$)—; —OP(O)($R^c$)—; —O-alkyl-heterocyclyl-N($R^k$)—; —N($R^k$)CHR$^g$C(O)N($R^k$)CHR$^g$C(O)—; —N($R^k$)CHR$^g$C(O)—; —N($R^k$)C(O)CHR$^g$—; —C(O)N($R^k$)CHR$^g$C(O)—; each of which is optionally substituted; or G is absent; and one of Q, U and V is N, and the other two are each CR$^g$ and each CR$^g$ may be the same or different.

Further, in formula (I), R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted heteroaryl, an optionally substituted aralkyl, an optionally substituted heteroaralkyl, —C(O)$R^c$, —$OR^k$, —$SR^k$, —$NR^hR^j$, hydroxylalkyl, nitro, cyano, haloalkyl, aminoalkyl, or —S(O)$_2R^c$; each of $R^a$ and $R^b$, independently, is H, optionally substituted alkyl, an optionally substituted cycloalkyl, an optionally substituted cyclyl, an optionally substituted heterocycloalkyl, an optionally substituted heterocyclyl, optionally substituted aryl, or optionally substituted heteroaryl; $R^c$ and $R^d$, for each occurrence, are independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —$OR^k$, —$SR^k$, —$NR^hR^j$, hydroxylalkyl, alkylcarbonylalkyl, mercaptoalkyl, aminoalkyl, sulfonylalkyl, sulfonylaryl, or thioalkoxy; $R^f$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, —C(O)$R^c$, —C(S)$R^c$, —C(NR)$R^c$, —S(O)$R^c$, —S(O)$_2R^c$, —P(O)$R^cR^c$, or —P(S)$R^cR^c$; $R^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —$OR^k$, —$SR^k$, —$NR^hR^j$, hydroxylalkyl, alkylcarbonylalkyl, mercaptoalkyl, aminoalkyl, sulfonylalkyl, sulfonylaryl, thioalkoxy, —C(O)$R^c$, —OC(O)$R^c$, —SC(O)$R^c$, —$NR^k$C(O)$R^c$, —C(S)$R^c$, —OC(S)$R^c$, —SC(S)$R^c$, —$NR^k$C(S)$R^c$, —C(NR)$R^c$, —OC(NR)$R^c$, —SC(NR)$R^c$, —$NR^k$C(NR)$R^c$, —SO$_2R^c$, —S(O)$R^c$, —$NR^k$SO$_2R^c$, —OS(O)$_2R^c$, —OP(O)$R^cR^c$, —P(O)$R^cR^c$, halo, aminoalkyl, mercaptoalkyl, cyano, nitro, nitroso, or azide; $R^h$ and $R^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or $R^h$ and $R^j$ taken together with the N to which they are attached is an optionally substituted heterocyclyl, an optionally substituted heterocycloalkyl, or an optionally substituted heteroaryl; and $R^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl.

In preferred embodiments: $R_1$ is

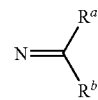

more preferably in which one of Q, U and V is N, and the other two are $CR^g$, wherein each $R^g$ is, independently selected from the group consisting of H, F, Cl, CN, a lower alkyl, a lower haloalkyl, a lower alkoxy, a lower haloalkoxy, a lower alkylamino, a lower dialkylamino, a lower aminoalkyl, and —NH$_2$. More preferably, one of Q, U and V is N, and the other two are independently selected from the group consisting of CH, CF, C(CN), CCl, C(CH$_3$), C(OCH$_3$), C(OCF$_3$), and C(CF$_3$), more preferably one of Q, U and V is N, and the other two are independently selected from the group consisting of CH and CF. In preferred embodiments, U is N and Q and V each are CH. In preferred embodiments, Z is N and W is O; in preferred embodiments, X is O or $NR^k$. In preferred embodiments, Y is a covalent bond, O, S, or CH$_2$, and n is 0, 1, 2, 3, or 4. In preferred embodiments, G is >C=N—R (e.g., an imine or oxime), —$NR^k$C(O)—, —C(O)$NR^k$—, —OC(O)—, —C(O)O—, —OC(O)O—, —$NR^k$C(O)O—, —OC(O)$NR^k$—, —$NR^k$C(S)O—, —OC(S)$NR^k$—, —$NR^k$C(NR)$NR^k$—, —$NR^k$C(O)$NR^k$—, —$NR^k$C(S)$NR^k$—, —$NR^k$S(O)$_2NR^k$—, —C(NR)$NR^k$—, or —$NR^k$C$R^gR^g$C(O)—. In preferred embodiments, $R_3$ is an optionally substituted alkyl, an optionally substituted aryl, an optionally substituted heteroaryl, an optionally substituted cycloalkyl, an optionally substituted cyclyl, an optionally substituted heterocycloalkyl, an optionally substituted heterocyclyl, nitro, cyano, halo, $OR^k$, $SR^k$ or $NR^hR^j$, more preferably optionally substituted aryl or optionally substituted heteroaryl. In preferred embodiments, $R_3$ is an optionally substituted phenyl, an optionally substituted naphthyl, an optionally substituted anthracenyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted tetrazolyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted indazolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo[b]thienyl. In other preferred embodiments, $R_3$ is an optionally substituted heterocycloalkyl. In preferred embodiments, $R_3$ is an optionally substituted piperidinyl, an optionally substituted piperazinyl, an optionally substituted 2-oxopiperazinyl, an optionally substituted 2-oxopiperidinyl, an optionally substituted 2-oxopyrrolidinyl, an optionally substituted 4-piperidonyl, an optionally substituted tetrahydropyranyl, an optionally substituted oxazolidinyl, an optionally substituted 2-oxo-oxazolidinyl, an optionally substituted tetrahydrothiopyranyl, an optionally substituted tetrahydrothiopyranyl sulfone, an optionally substituted morpholinyl, an optionally substituted thiomorpholinyl, an optionally substituted thiomorpholinyl sulfoxide, an optionally substituted thiomorpholinyl sulfone, an optionally substituted 1,3-dioxolanyl, an optionally substituted [1,4]dioxanyl, an optionally substituted 2-oxo-imidazolidinyl, tetrahydrofuranyl, or an optionally substituted tetrahydrothienyl. In preferred embodiments, $R_3$ is —$OR^k$ or —$NR^hR^j$, and $R^f$, $R^h$ and $R^j$ are each, independently, H or alkyl. In certain preferred embodiments, $R_3$ is

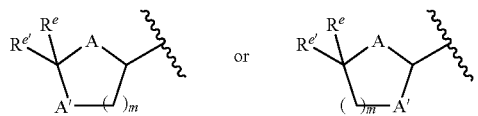

in which each of A and A', independently, is O, S, NH or $NR^y$, wherein $R^y$ is lower alkyl; each of $R^e$ and $R^{e'}$, independently is H, optionally substituted alkyl, substituted aryl, or substituted heteroaryl; and m is 1 or 2. In certain preferred embodiments, $R_3$ is —$C(O)OR^k$, —$OC(O)R^k$, —$C(O)NR^hR^j$, —$NR^kC(O)R^k$, —$C(S)OR^k$, —$OC(S)R^k$, —$NR^kC(O)NR^hR^j$, —$NR^kC(S)NR^hR^j$, —$C(O)NRhRj$, —$S(O)_2R^k$, —$S(O)_2NR^hR^j$, —$OC(O)NR^hR^j$, or —$NR^kC(O)OR^k$.

In certain embodiments of the compounds of Formula (I), one of $R^a$ or $R^b$ is an optionally substituted aryl or an optionally substituted heteroaryl. In certain preferred embodiments, one of $R^a$ and $R^b$ is

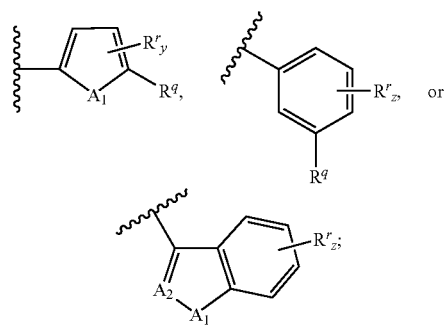

in which $A_1$ is $NR^i$, O, or S; $A_2$ is N or $CR^i$; $R^q$ is H, halogen, CN, optionally substituted alkyl, optionally substituted cyclyl, optionally substituted alkyloxy, optionally substituted alkylcarbonyl, optionally substituted alkyloxycarbonyl, optionally substituted aryloxycarbonyl, optionally substituted heteroaryloxycarbonyl, hydroxyalkyl, alkylamino, or alkylaminocarbonyl; each $R^r$ is, independently, H, halogen, $NO_2$, CN, optionally substituted alkyl, optionally substituted aryl, optionally substituted heteroaryl, $OR^k$, $OC(O)R^k$, $SO_2R^k$, $S(O)R^k$, $S(O_2)NR^hR^j$, $SR^k$, $NR^hR^j$, $NR^kCOR^k$, $NR^kC(O)OR^k$, $NR^kC(O)NR^hR^j$, $NR^kSO_2R^k$, $COR^k$, $C(O)OR^k$, or $C(O)NR^hR^j$; $R^i$ is H, optionally substituted alkyl, or optionally substituted alkylcarbonyl; y is 0, 1, or 2; and z is 0, 1, 2, 3, or 4. In further preferred embodiments, one of $R^a$ and $R^b$ is

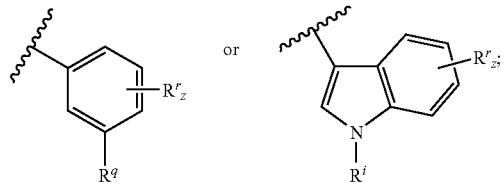

and the other of $R^a$ and $R^b$ is H or alkyl. In certain preferred embodiments, $R^q$ is H, methyl, ethyl, propyl, cyclopropyl, methoxy, ethoxy, methoxycarbonyl, or halogen; each $R^r$ is, independently, F, Cl, CN, methyl, methoxy, ethoxy, —$NH_2$, —$NHCH_3$, —$N(CH_3)_2$, —$NHCH_2CH_3$, —$N(CH_2CH_3)_2$, $OC(O)CH_3$, $OC(O)C_2H_5$, $C(O)OH$, $C(O)OC_2H_5$, $C(O)NH_2$, $NHC(O)CH_3$, or $S(O_2)NH_2$; $R^i$ is H, methyl, ethyl, or acetyl, and z is 0, 1, or 2. In preferred embodiments, one of Q, U and V is N, and the other two are each CH, and more preferably, U is N, Q and V are each CH, Z is N, and W is O; in still more preferred embodiments, X is $NR^k$; and $R^k$ is H, methyl, ethyl, or acetyl, and yet more preferably, Y is a covalent bond, O, S, or NH, $N(CH_3)$, $CH_2$; and n is 0, 1, 2, 3, or 4; still more preferably, $R_3$ is $R^k$, nitro, cyano, halo, $OR^k$, $SR^k$, $C(O)R^k$, $C(O)OR^k$, or $C(O)NR^hR^j$. In other preferred embodiments, Q is N, U and V are each CH, Z is N, and W is O; or V is N, Q and U are each CH, Z is N, and W is O.

In certain preferred embodiments of the compounds of formula (I), $R_1$ is optionally substituted aryl or optionally substituted heteroaryl; more preferably in these embodiments, G is >C=N—R, —$NR^kC(O)$—, —$C(O)NR^k$—, —$OC(O)$—, —$C(O)O$—, —$OC(O)O$—, —$NR^kC(O)O$—, —$OC(O)NR^k$—, —$NR^kC(S)O$—, —$OC(S)NR^k$—, —$NR^kC(NR)NR^k$—, —$NR^kC(O)NR^k$—, —$NR^kC(S)NR^k$—, —$NR^kS(O)_2NR^k$—, —$C(NR)NR^k$—, or —$NR^kCR^gR^gC(O)$—. In certain embodiments, $R_1$ is

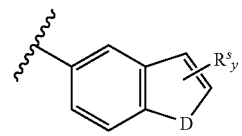

in which D is O, S, or $NR^t$; each $R^s$ is, independently, phenyl, halogen, CN, hydroxyl, optionally substituted alkyl, optionally substituted aryl, optionally substituted heteroaryl, optionally substituted alkoxyl, optionally substituted aryloxyl, or optionally substituted heteroaryloxyl; $R^t$ is H, alkyl, or alkylcarbonyl; and y is 0, 1, or 2; in preferred embodiments, X is $NR^k$ in which $R^k$ is H, methyl, ethyl, or acetyl.

In certain embodiments of Formula (I) in which $R_1$ is optionally substituted aryl or optionally substituted heteroaryl, G is preferably >C=N—R, —$NR^kC(O)$—, —$C(O)NR^k$—, —$OC(O)$—, —$C(O)O$—, —$OC(O)O$—, —$NR^kC(O)O$—, —$OC(O)NR^k$—, —$NR^kC(S)O$—, —$OC(S)NR^k$—, —$NR^kC(NR)NR^k$—, —$NR^kC(O)NR^k$—, —$NR^kC(S)NR^k$—, —$NR^kS(O)_2NR^k$—, —$C(NR)NR^k$—, or —$NR^kCR^gR^gC(O)$—. In certain embodiments of Formula (I) in which $R_1$ is aryl or heteroaryl, $R_1$ is

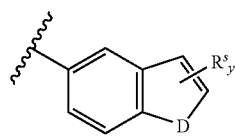

wherein D is O, S, or NR$^t$; each R$^s$ is, independently, phenyl, halogen, CN, hydroxyl, optionally substituted alkyl, optionally substituted aryl, optionally substituted heteroaryl, optionally substituted alkoxyl, optionally substituted aryloxyl, or optionally substituted heteroaryloxyl; R$^t$ is H, alkyl, or alkylcarbonyl; and y is 0, 1, or 2; in preferred embodiments, X is NR$^k$; and R$^k$ is H, methyl, ethyl, or acetyl.

In certain embodiments of Formula (I) in which R$_1$ is optionally substituted aryl or optionally substituted heteroaryl, one of Q, U and V is N, and the other two are each CH; more preferably, Q is N, U and V are each CH, Z is N, and W is O; or V is N, Q and U are each CH, Z is N, and W is O; or U is N, Q and V are each CH, Z is N, and W is O, and more preferably, Y is a covalent bond, O, S, NH, N(CH$_3$) or CH$_2$, and n is 0, 1, 2, 3, or 4; more preferably, R$_3$ is optionally substituted aryl or optionally substituted heteroaryl; still more preferably, R$_3$ is an optionally substituted phenyl, an optionally substituted naphthyl, an optionally substituted anthracenyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted tetrazolyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted indazolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo[b]thienyl; or R$_3$ is an optionally substituted heterocycloalkyl; in certain preferred embodiments, R$_3$ is an optionally substituted piperidinyl, an optionally substituted piperazinyl, an optionally substituted 2-oxopiperazinyl, an optionally substituted 2-oxopiperidinyl, an optionally substituted 2-oxopyrrolidinyl, an optionally substituted 4-piperidonyl, an optionally substituted tetrahydropyranyl, an optionally substituted oxazolidinyl, an optionally substituted 2-oxo-oxazolidinyl, an optionally substituted tetrahydrothiopyranyl, an optionally substituted tetrahydrothiopyranyl sulfone, an optionally substituted morpholinyl, an optionally substituted thiomorpholinyl, an optionally substituted thiomorpholinyl sulfoxide, an optionally substituted thiomorpholinyl sulfone, an optionally substituted 1,3-dioxolanyl, an optionally substituted [1,4]dioxanyl, an optionally substituted 2-oxo-imidazolidinyl, tetrahydrofuranyl, or an optionally substituted tetrahydrothienyl; or R$_3$ is cyano, halo, nitro, —OR$^k$, —SR$^k$, C(O)OR$^k$, NR$^h$R$^j$, C(O)NR$^h$R$^j$, —OC(O)R$^k$, —NR$^k$C(O)R$^k$, —C(S)OR$^k$, —OC(S)R$^k$, —NR$^k$C(O)NR$^h$R$^j$, —NR$^k$C(S)NR$^h$R$^j$, —C(O)NRhRj, —S(O)$_2$R$^k$, —S(O)$_2$NR$^h$R$^j$, —OC(O)NR$^h$R$^j$, or —NR$^k$C(O)OR$^k$, more preferably R$_3$ is

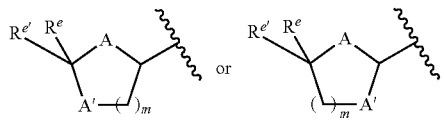

in which each of A and A', independently, is O, S, NH, or NR$^y$, wherein R$^y$ is a lower alkyl; each of R$^e$ and R$^{e'}$, independently, is H, optionally substituted alkyl, optionally substituted aryl, or optionally substituted heteroaryl; and m is 1 or 2; in certain embodiments, R$_1$ is

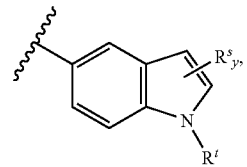

in which R$^t$ is H, alkyl, or alkylcarbonyl; each R$^s$ is, independently, chloro, cyano, methyl, ethyl, propyl, or phenyl; and r is 1 or 2.

In certain preferred embodiments of formula (I), R$_1$ is

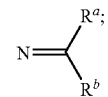

and each of R$_2$ and R$_4$ is H; R$_3$ is H, nitro, cyano, halo, —C(O)OR$^k$, —OC(O)R$^k$, —C(O)NR$^h$R$^j$, —NR$^k$C(O)R$^k$, —C(S)OR$^k$, —OC(S)R$^k$, —NR$^k$C(O)NR$^h$R$^j$, —NR$^k$C(S)NR$^h$R$^j$, —C(O)NRhRj, —S(O)$_2$R$^k$, —S(O)$_2$NR$^h$R$^j$, —OC(O)NR$^h$R$^j$, —NR$^k$C(O)OR$^k$, an optionally substituted alkyl, optionally substituted aryl, optionally substituted heteroaryl, optionally substituted cyclyl, optionally substituted heterocyclyl, optionally substituted alkyloxycarbonyl, optionally substituted alkylaminocarbonyl, or optionally substituted alkylcarbonyl; G is absent; and X is NR$^k$; in more preferred embodiments, X is NH; in other preferred embodiments, one of R$^a$ and R$^b$ is H or alkyl; and the other is aryl or heteroaryl wherein the aryl or the heteroaryl are optionally substituted with R$^q$ and R$^r_z$, in which R$^q$ is halogen, CN, optionally substituted alkyl, optionally substituted alkyloxy, optionally substituted alkylcarbonyl, optionally substituted alkyloxycarbonyl, optionally substituted aryloxycarbonyl, optionally substituted heteroaryloxycarbonyl, hydroxyalkyl, alkylamino, or alkylaminocarbonyl; R$^r$ is halogen, CN, hydroxyl, optionally substituted alkyl, optionally substituted aryl, optionally substituted heteroaryl, optionally substituted alkoxyl, optionally substituted aryloxyl, or optionally substituted heteroaryloxyl; and z is 0, 1, 2, 3, or 4; still more preferably, one of R$^a$ and R$^b$ is H or alkyl; and the other is

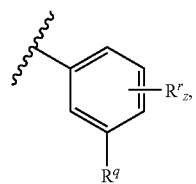

in which $R^q$ is H, —OH, —NH$_2$, alkylamino, dialkylamino, alkyl, alkoxyl, methoxycarbonyl, or halo; each $R^r$ is, independently, halo, CN, hydroxyl, —NH$_2$, alkylamino, dialkylamino, alkyl, aryl, heteroaryl, alkoxyl, aryloxyl, heteroaryloxyl, or —NHC(O)R$^y$, wherein R$^y$ is a lower alkyl; and z is 0, 1, 2, 3, or 4. In certain embodiments, one of Q, U and V is N, and the other two are each CH; more preferably, U is N, Q and V are each CH, Z is N, and W is O; or Q is N, U and V are each CH, Z is N, and W is O; or U is V, Q and U are each CH, Z is N, and W is O. In certain embodiments, R$_3$ is optionally substituted heteroaryl or optionally substituted heterocyclyl; more preferably, R$_3$ is pyridinyl, 1-oxy-pyridinyl, 1H-pyridin-2-one, morpholin-4-yl, 4-methyl-piperazin-1-yl, or 2-oxo-oxazolidin-3-yl; still more preferably, G is absent, n is 2, and Y is O; yet more preferably, X is NH; and still more preferably, one of R$^a$ and R$^b$ is H or alkyl, and the other is

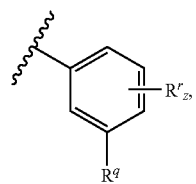

in which $R^q$ is H, —OH, —NH$_2$, alkylamino, dialkylamino, alkyl, alkoxyl, methoxycarbonyl, or halogen; each $R^r$ is, independently, halogen, CN, —OH, —NH$_2$, —NHCH$_3$, —N(CH$_3$)$_2$, —NHC(O)CH$_3$, lower alkoxy, alkyl, aryl, heteroaryl, alkoxyl, aryloxyl, eteroaryloxyl, or —NHC(O)R$^y$, wherein R$^y$ is a lower alkyl; and z is 0, 1, 2, 3, or 4. In more preferred embodiments, one of R$^a$ and R$^b$ is H or methyl, and the other is

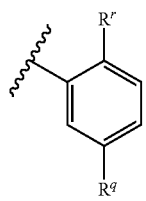

in which $R^r$ is H, halo, CN, —OH, —NH$_2$, —NHCH$_3$, —N(CH$_3$)$_2$, —NHC(O)CH$_3$, lower alkoxy, or lower alkyl; more preferably, R$^r$ is H, OH, NH$_2$, CN or F.

In still other embodiments of formula (I), Q, U and V is N, and the other two are each CH; more preferably Q is N and U and V are each CH; or V is N and Q and U are each CH; or U is N and Q and V are each CH.

In certain preferred embodiments of the compounds of formula (I), Y is O, n is 2, R$_2$ and R$_4$ are H for all occurrences, G is absent, and R$_3$ is R$^g$, in which R$^g$ is optionally substituted heterocyclyl, more preferably morpholinyl, still more preferably morpholin-4-yl.

In another aspect, the invention provides a pharmaceutical composition comprising a pharmaceutically acceptable carrier and a compound of formula (I), supra. In preferred embodiments, R$_1$ is

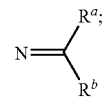

each of R$_2$ and R$_4$ is H; R$_3$ is H, —C(O)OR$^k$, —OC(O)R$^k$, —C(O)NR$^h$R$^j$, —NR$^k$C(O)R$^k$, —C(S)OR$^k$, —OC(S)R$^k$, —NR$^k$C(O)NR$^h$R$^j$, —NR$^k$C(S)NR$^h$R$^j$, —C(O)NRhRj, —S(O)$_2$R$^k$, —S(O)$_2$NR$^h$R$^j$, —OC(O)NR$^h$R$^j$, or —NR$^k$C(O)OR$^k$, a halo, nitro, cyano, an optionally substituted alkyl, optionally substituted aryl, optionally substituted heteroaryl, optionally substituted cyclyl, optionally substituted heterocyclyl, optionally substituted alkyloxycarbonyl, optionally substituted alkylaminocarbonyl, or optionally substituted alkylcarbonyl; and X is NR$^k$. In certain preferred pharmaceutical compositions, the compound is characterized in that one of R$^a$ and R$^b$ is H or alkyl; and the other is aryl or heteroaryl, wherein the aryl or heteroaryl is optionally substituted with R$^q$ and R$^r_z$, in which R$^q$ is halogen, CN, —NH$_2$, alkylamino, dialkylamino, alkyl, alkyloxy, alkylcarbonyl, alkyloxycarbonyl, aryloxycarbonyl, heteroaryloxycarbonyl, hydroxyalkyl, alkylamino, or alkylaminocarbonyl; each R$^r$ is, independently, halogen, CN, hydroxyl, —NH$_2$, alkylamino, dialkylamino, alkyl, aryl, heteroaryl, alkoxyl, aryloxyl, heteroaryloxyl or —NHC(O)R$^y$, wherein R$^y$ is a lower alkyl; and z is 0, 1, 2, 3, or 4.

In more preferred embodiments, compounds of the invention include the following:

Compound 1: N-{2-[2-(3,4-Dimethoxy-phenyl)-ethoxy]-6-morpholin-4-yl-pyridin-4-yl}-N'-(1H-indol-3-ylmethylene)-hydrazine;

Compound 2: N-{6-[2-(3,4-Dimethoxy-phenyl)-ethoxy]-4-morpholin-4-yl-pyridin-2-yl}-N'-(1H-indol-3-ylmethylene)-hydrazine;

Compound 3: N-{4-[2-(3,4-Dimethoxy-phenyl)-ethoxy]-6-morpholin-4-yl-pyridin-2-yl}-N'-(1H-indol-3-ylmethylene)-hydrazine;

Compound 4: {6-[2-(3,4-Dimethoxy-phenyl)-ethoxy]-4-morpholin-4-yl-pyridin-2-yl}-(2,3-dimethyl-1H-indol-5-yl)-amine;

Compound 5: N-{4-[2-(3,4-Dimethoxy-phenyl)-ethoxy]-6-morpholin-4-yl-pyridin-2-yl}-N'-(3-methyl-benzylidene)-hydrazine;

Compound 6: N-{2-[2-(3,4-Dimethoxy-phenyl)-ethoxy]-6-morpholin-4-yl-pyridin-4-yl}-N'-(3-methyl-benzylidene)-hydrazine;

Compound 7: N-{6-[2-(3,4-Dimethoxy-phenyl)-ethoxy]-4-morpholin-4-yl-pyridin-2-yl}-N'-(3-methyl-benzylidene)-hydrazine;

Compound 8: {2-[2-(3,4-Dimethoxy-phenyl)-ethoxy]-6-morpholin-4-yl-pyridin-4-yl}-(2,3-dimethyl-1H-indol-5-yl)-amine;

Compound 9: {4-[2-(3,4-Dimethoxy-phenyl)-ethoxy]-6-morpholin-4-yl-pyridin-2-yl}-(2,3-dimethyl-1H-indol-5-yl)-amine;

Compound 10: {4-[2-(3,4-Dimethoxy-phenyl)-ethoxy]-6-morpholin-4-yl-pyridin-2-yl}-m-tolyl-amine.

Their structures are delineated below.
-continued
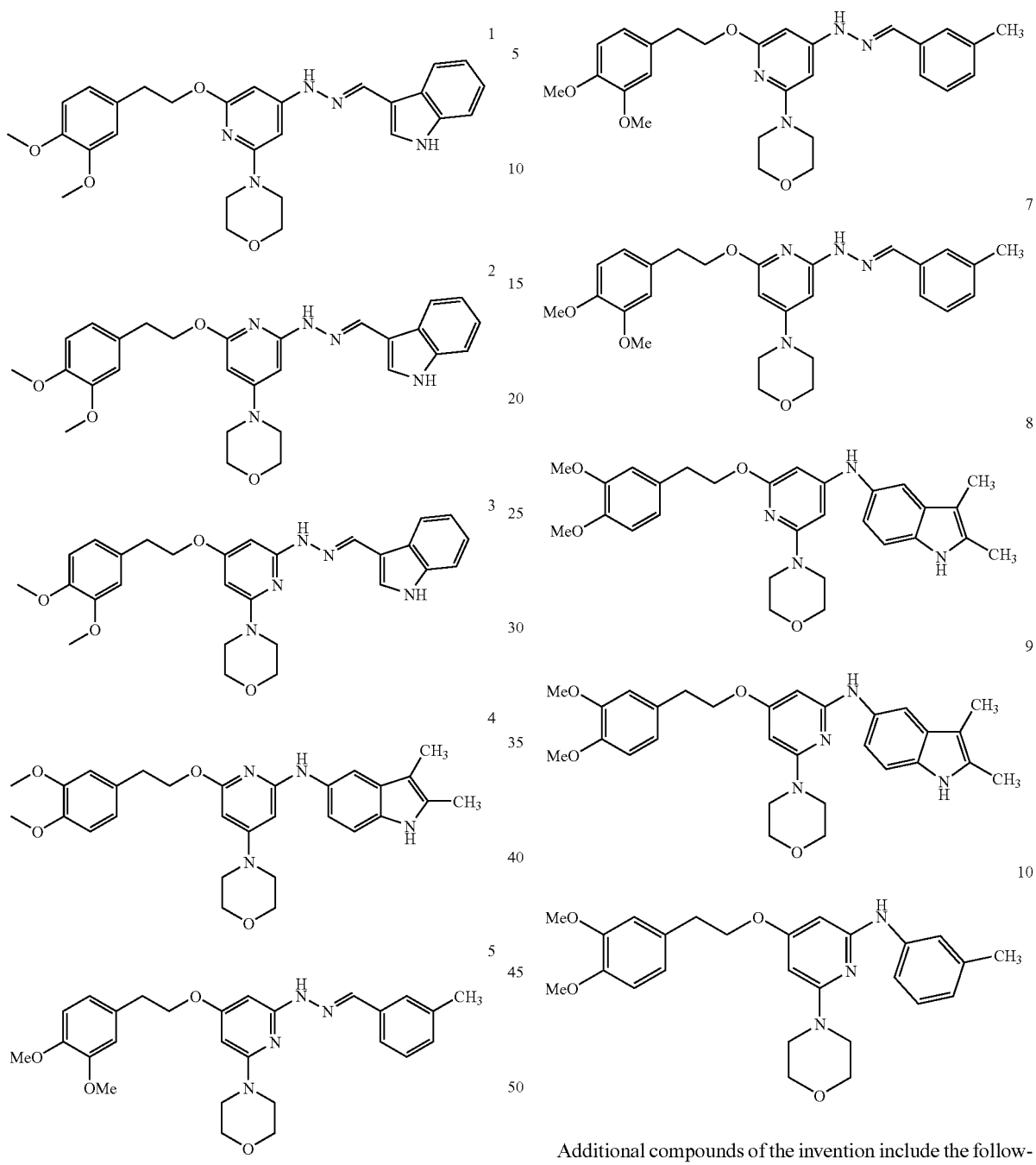
Additional compounds of the invention include the following:
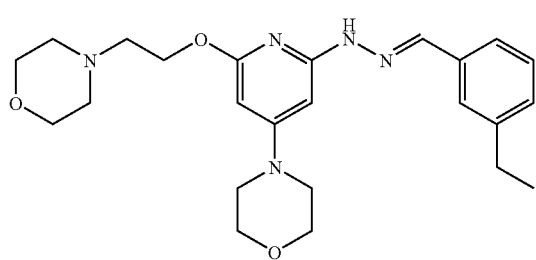
N-(3-Ethyl-benzylidene)-N'-[4-morpholin-4-yl-6-(2-morpholin-4-yl-ethoxy)-pyridin-2-yl]-hydrazine -continued

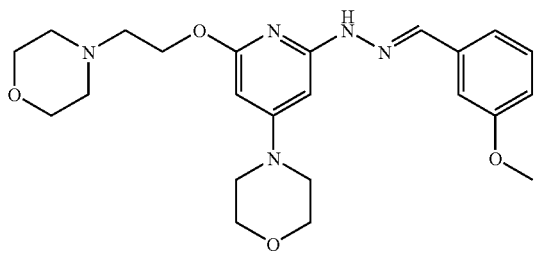

N-(3-Methoxy-benzylidene)-N'-[4-morpholin-4-yl-6-(2-morpholin-4-yl-ethoxy)-pyridin-2-yl]-hydrazine

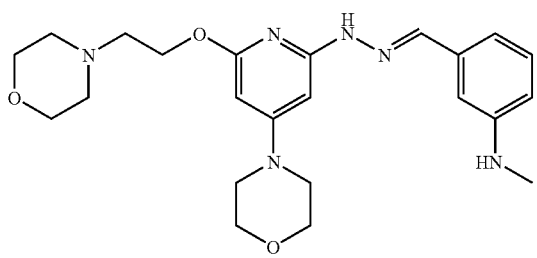

Methyl-(3-{[4-morpholin-4-yl-6-(2-morpholin-4-yl-ethoxy)-pyridin-2-yl]-hydrazonomethyl}-phenyl)-amine

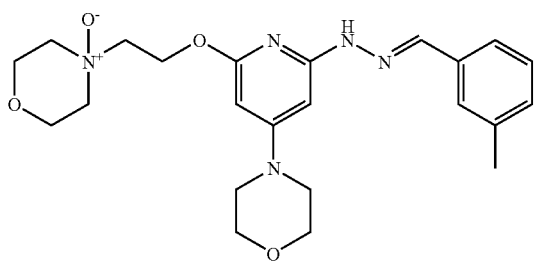

N-(3-Methyl-benzylidene)-N'-{4-morpholin-4-yl-6-[2-(4-oxy-morpholin-4-yl)-ethoxy]-pyridin-2-yl}-hydrazine

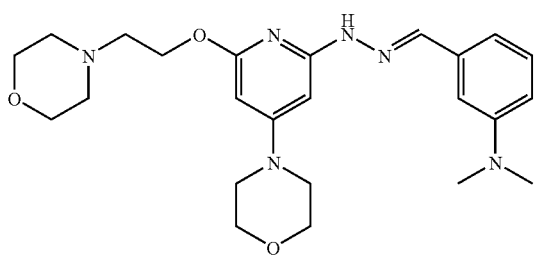

Dimethyl-(3-{[4-morpholin-4-yl-6-(2-morpholin-4-yl-ethoxy)-pyridin-2-yl]-hydrazonomethyl}-phenyl)-amine

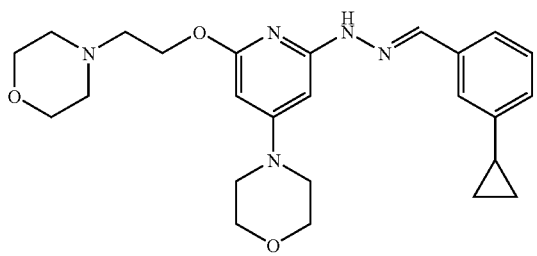

N-(3-Cyclopropyl-benzylidene)-N'-[4-morpholin-4-yl-6-(2-morpholin-4-yl-ethoxy)-pyridin-2-yl]-hydrazine

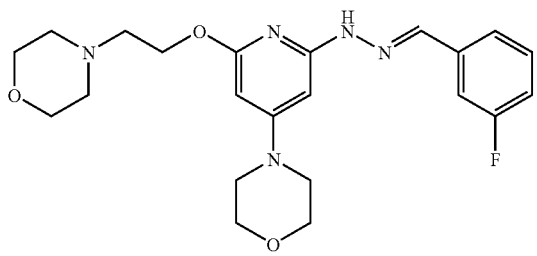

N-(3-Fluoro-benzylidene)-N'-[4-morpholin-4-yl-6-(2-morpholin-4-yl-ethoxy)-pyridin-2-yl]-hydrazine -continued

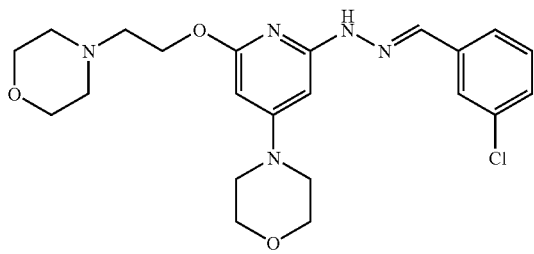
N-(3-Chloro-benzylidene)-N'-[4-morpholin-4-yl-6-(2-morpholin-4-yl-ethoxy)-pyridin-2-yl]-hydrazine

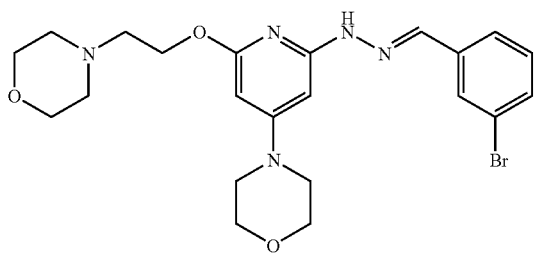
N-(3-Bromo-benzylidene)-N'-[4-morpholin-4-yl-6-(2-morpholin-4-yl-ethoxy)-pyridin-2-yl]-hydrazine

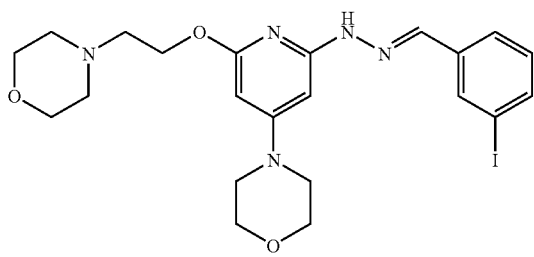
N-(3-Iodo-benzylidene)-N'-[4-morpholin-4-yl-6-(2-morpholin-4-yl-ethoxy)-pyridin-2-yl]-hydrazine

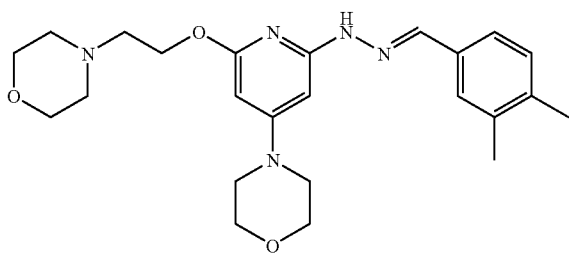
N-(3,4-Dimethyl-benzylidene)-N'-[4-morpholin-4-yl-6-(2-morpholin-4-yl-ethoxy)-pyridin-2-yl]-hydrazine

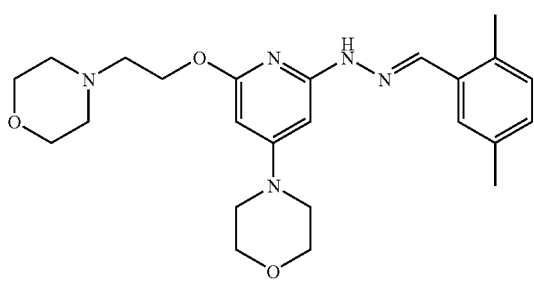
N-(2,5-Dimethyl-benzylidene)-N'-[4-morpholin-4-yl-6-(2-morpholin-4-yl-ethoxy)-pyridin-2-yl]-hydrazine

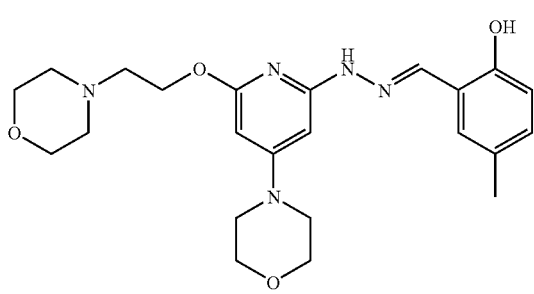
4-Methyl-2-{[4-morpholin-4-yl-6-(2-morpholin-4-yl-ethoxy)-pyridin-2-yl]-hydrazonomethyl}-phenol

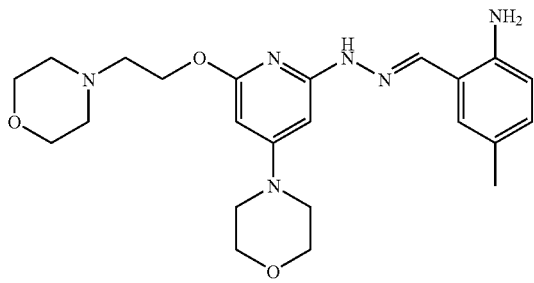

4-Methyl-2-{[4-morpholin-4-yl-6-(2-morpholin-4-yl-ethoxy)-pyridin-2-yl]-hydrazonomethyl}-phenylamine

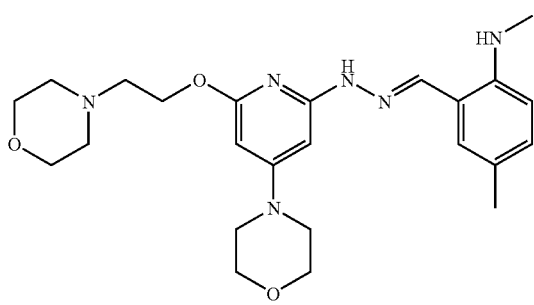

Methyl-(4-methyl-2-{[4-morpholin-4-yl-6-(2-morpholin-4-yl-ethoxy)-pyridin-2-yl]-hydrazonomethyl}-phenyl)-amine

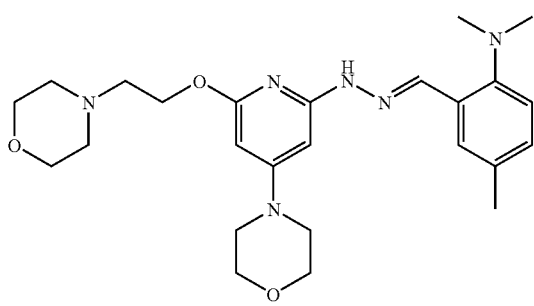

Dimethyl-(4-methyl-2-{[4-morpholin-4-yl-6-(2-morpholin-4-yl-ethoxy)-pyridin-2-yl]-hydrazonomethyl}-phenyl)-amine

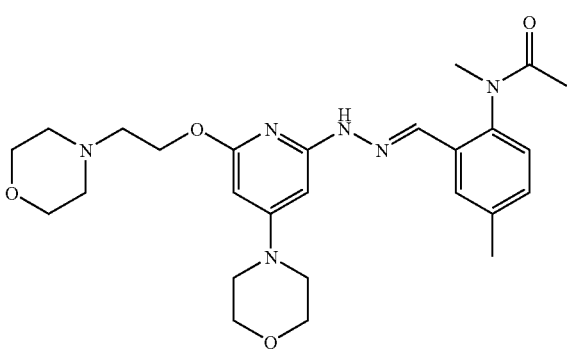

N-Methyl-N-(4-methyl-2-{[4-morpholin-4-yl-6-(2-morpholin-4-yl-ethoxy)-pyridin-2-yl]-hydrazonomethyl}-phenyl)-acetamide

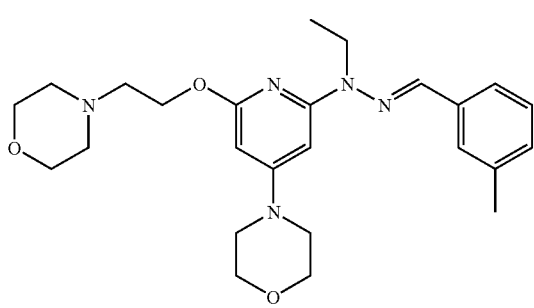

N-Ethyl-N'-(3-methyl-benzylidene)-N-[4-morpholin-4-yl-6-(2-morpholin-4-yl-ethoxy)-pyridin-2-yl]-hydrazine

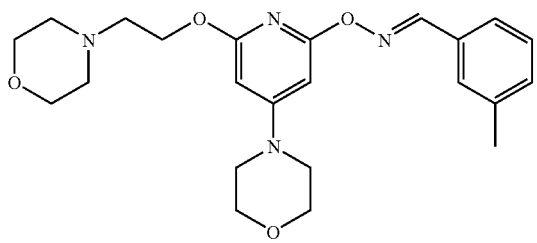

3-Methyl-benzaldehyde O-[4-morpholin-4-yl-6-(2-morpholin-4-yl-ethoxy)-pyridin-2-yl]-oxime

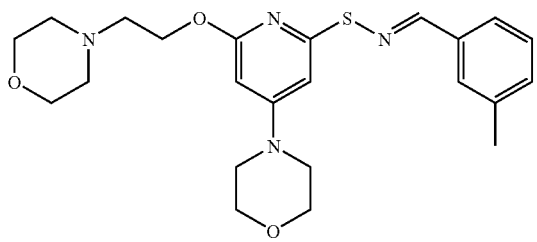

3-Methyl-benzaldehyde O-[4-morpholin-4-yl-6-(2-morpholin-4-yl-ethoxy)-pyridin-2-yl]-thiooxime

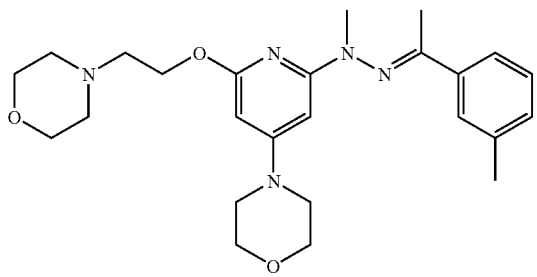

N-Methyl-N-[4-morpholin-4-yl-6-(2-morpholin-4-yl-ethoxy)-pyridin-2-yl]-N'-(1-m-tolyl-ethylidene)-hydrazine

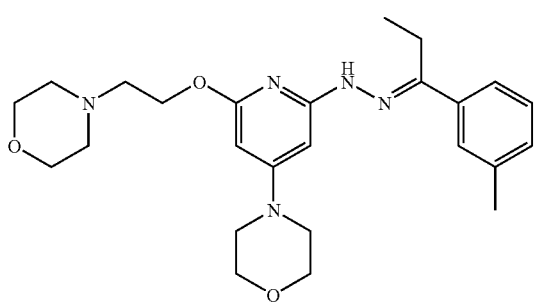

N-[4-Morpholin-4-yl-6-(2-morpholin-4-yl-ethoxy)-pyridin-2-yl]-N'-(1-m-tolyl-propylidene)-hydrazine

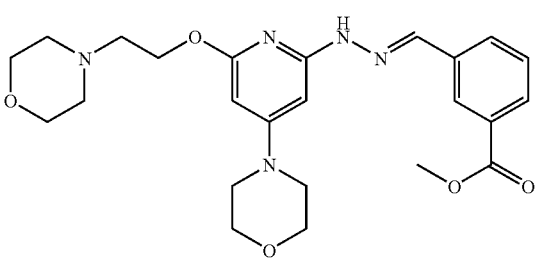

3-{[4-Morpholin-4-yl-6-(2-morpholin-4-yl-ethoxy)-pyridin-2-yl]-hydrazonomethyl}-benzoic acid methyl ester

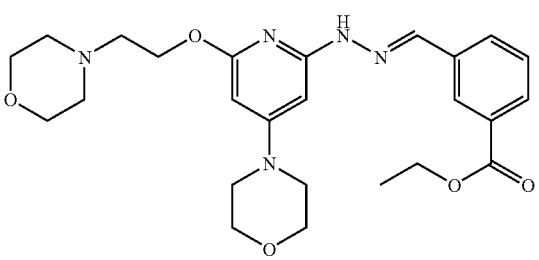

3-{[4-Morpholin-4-yl-6-(2-morpholin-4-yl-ethoxy)-pyridin-2-yl]-hydrazonomethyl}-benzoic acid ethyl ester -continued

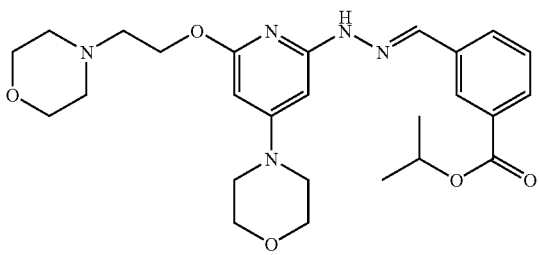

3-{[4-Morpholin-4-yl-6-(2-morpholin-4-yl-ethoxy)-pyridin-2-yl]-hydrazonomethyl}-benzoic acid isopropyl ester

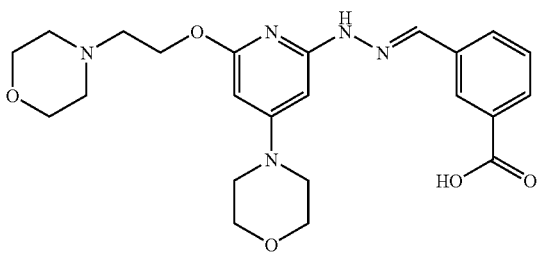

3-{[4-Morpholin-4-yl-6-(2-morpholin-4-yl-ethoxy)-pyridin-2-yl]-hydrazonomethyl}-benzoic acid

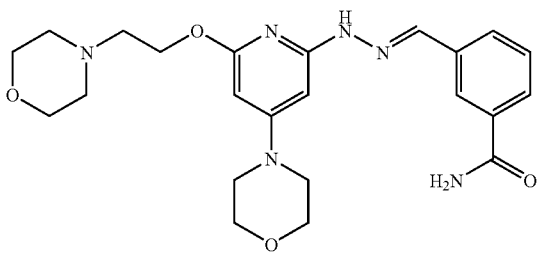

3-{[4-Morpholin-4-yl-6-(2-morpholin-4-yl-ethoxy)-pyridin-2-yl]-hydrazonomethyl}-benzamide

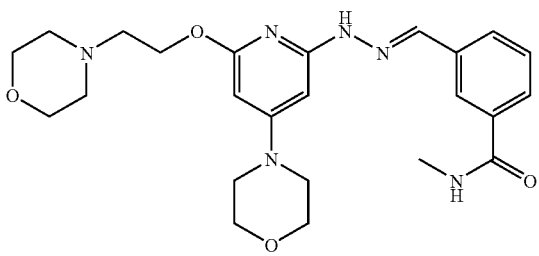

N-Methyl-3-{[4-morpholin-4-yl-6-(2-morpholin-4-yl-ethoxy)-pyridin-2-yl]-hydrazonomethyl}-benzamide

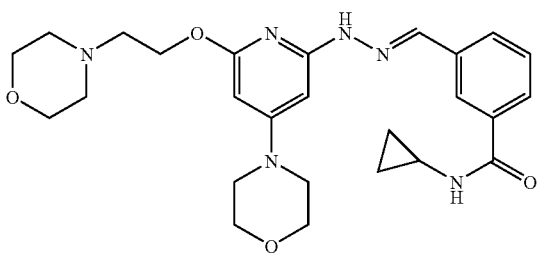

N-Cyclopropyl-3-{[4-morpholin-4-yl-6-(2-morpholin-4-yl-ethoxy)-pyridin-2-yl]-hydrazonomethyl}-benzamide

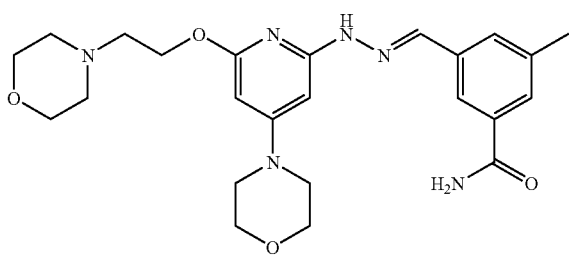

3-Methyl-5-{[4-morpholin-4-yl-6-(2-morpholin-4-yl-ethoxy)-pyridin-2-yl]-hydrazonomethyl}-benzamide

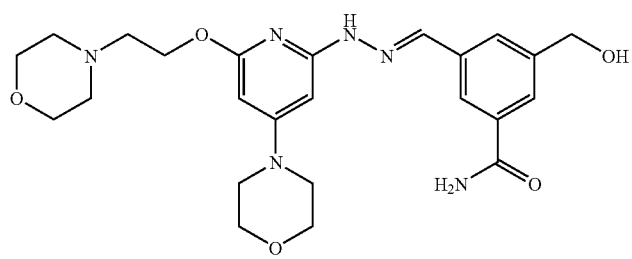

3-Hydroxymethyl-5-{[4-morpholin-4-yl-6-(2-morpholin-4-yl-ethoxy)-pyridin-2-yl]-hydrazonomethyl}-benzamide

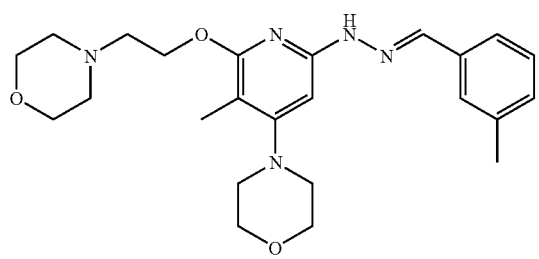

N-(3-Methyl-benzylidene)-N'-[5-methyl-4-morpholin-4-yl-6-(2-morpholin-4-yl-ethoxy)-pyridin-2-yl]-hydrazine

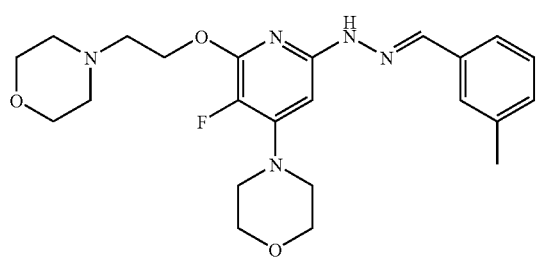

N-[5-Fluoro-4-morpholin-4-yl-6-(2-morpholin-4-yl-ethoxy)-pyridin-2-yl]-N'-(3-methyl-benzylidene)-hydrazine

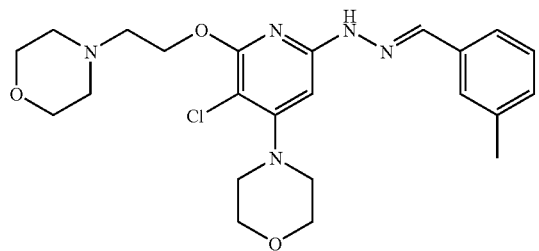

N-[5-Chloro-4-morpholin-4-yl-6-(2-morpholin-4-yl-ethoxy)-pyridin-2-yl]-N'-(3-methyl-benzylidene)-hydrazine

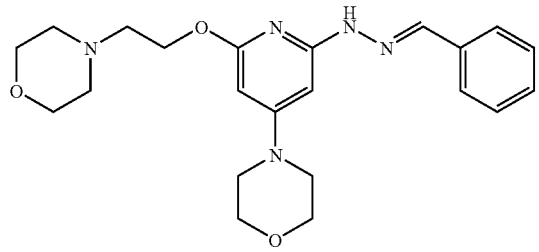

N-Benzylidene-N'-[4-morpholin-4-yl-6-(2-morpholin-4-yl-ethoxy)-pyridin-2-yl]-hydrazine

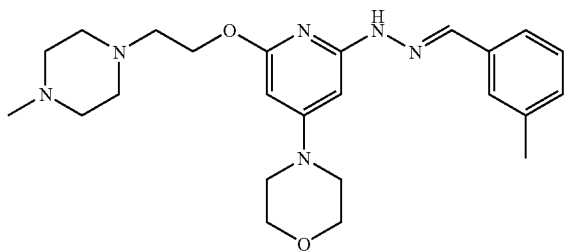

N-(3-Methyl-benzylidene)-N'-{6-[2-(4-methyl-piperazin-1-yl)-ethoxy]-4-morpholin-4-yl-pyridin-2-yl}-hydrazine -continued

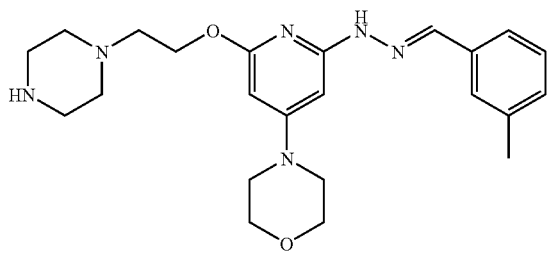
N-(3-Methyl-benzylidene)-N'-[4-morpholin-4-yl-6-(2-piperazin-1-yl-ethoxy)-pyridin-2-yl+9-hydrazine

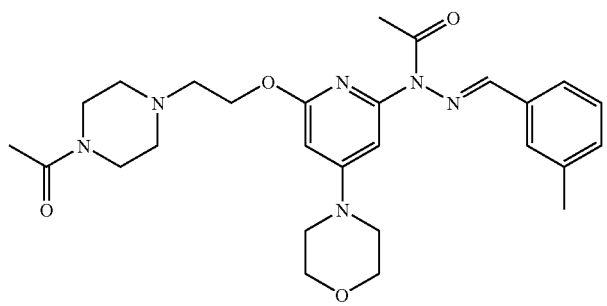
Acetic acid N-{6-[2-(4-acetyl-piperazin-1-yl)-ethoxy]-4-morpholin-4-yl-pyridin-2-yl}-N'-(3-methyl-benzylidene)-hydrazide

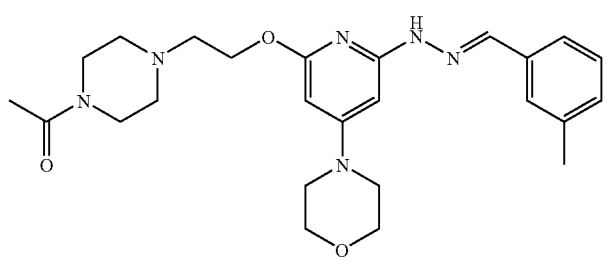
1-[4-(2-{6-[N'-(3-Methyl-benzylidene)-hydrazino]-4-morpholin-4-yl-pyridin-2-yloxy}-ethyl)-piperazin-1-yl]-ethanone

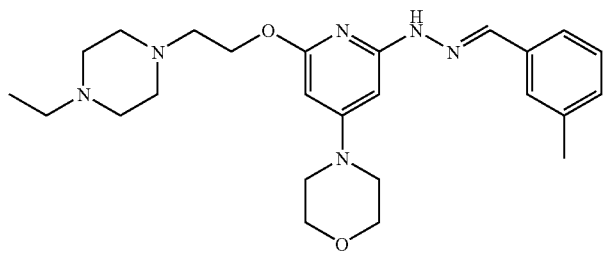
N-{6-[2-(4-Ethyl-piperazin-1-yl)-ethoxy]-4-morpholin-4-yl-pyridin-2-yl}-N'-(3-methyl-benzylidene)-hydrazine

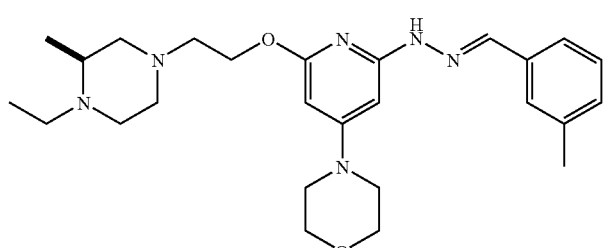
N-{6-[2-(4-Ethyl-3-methyl-piperazin-1-yl)-ethoxy]-4-morpholin-4-yl-pyridin-2-yl}-N'-(3-methyl-benzylidene)-hydrazine

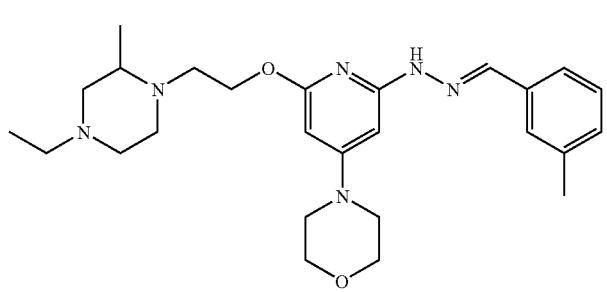
N-{6-[2-(4-Ethyl-2-methyl-piperazin-1-yl)-ethoxy]-4-morpholin-4-yl-pyridin-2-yl}-N'-(3-methyl-benzylidene)-hydrazine

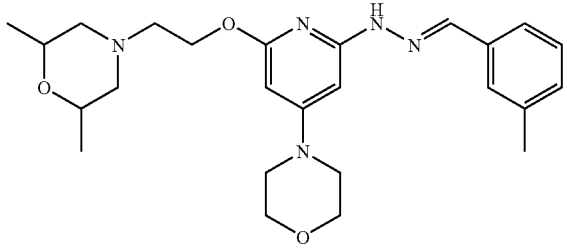

N-{6-[2-(2,6-Dimethyl-morpholin-4-yl)-ethoxy]-4-morpholin-4-yl-pyridin-2-yl}-N'-(3-methyl-benzylidene)-hydrazine

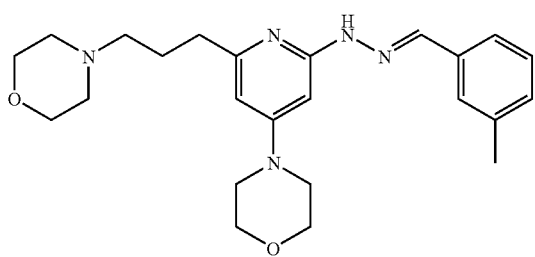

N-(3-Methyl-benzylidene)-N'-[4-morpholin-4-yl-6-(3-morpholin-4-yl-propyl)-pyridin-2-yl]-hydrazine

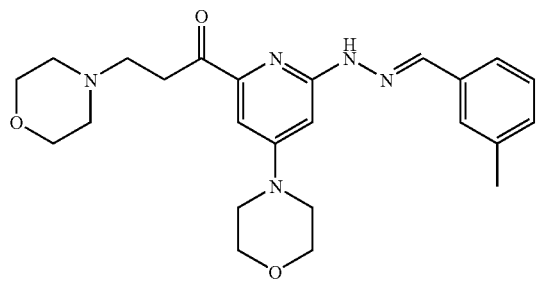

1-{6-[N'-(3-Methyl-benzylidene)-hydrazino]-4-morpholin-4-yl-pyridin-2-yl}-3-morpholin-4-yl-propan-1-one

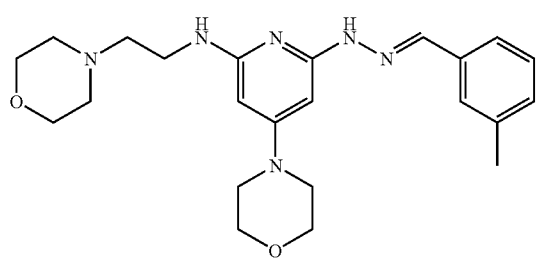

{6-[N'-(3-Methyl-benzylidene)-hydrazino]-4-morpholin-4-yl-pyridin-2-yl}-(2-morpholin-4-yl-ethyl)-amine

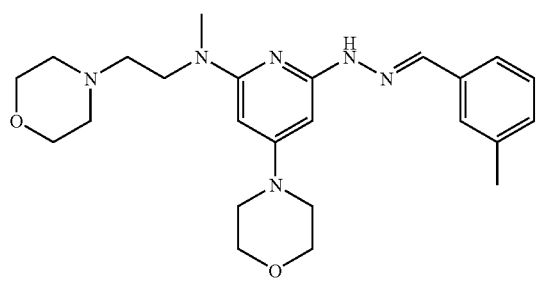

Methyl-{6-[N'-(3-methyl-benzylidene)-hydrazino]-4-morpholin-4-yl-pyridin-2-yl}-(2-morpholin-4-yl-ethyl)-amine

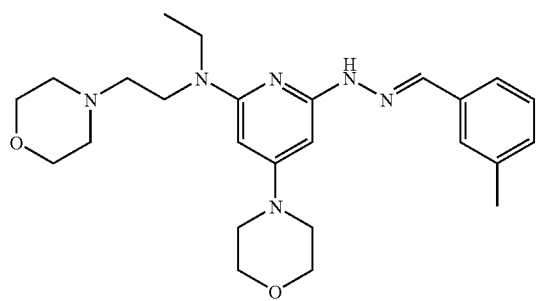

Ethyl-{6-[N'-(3-methyl-benzylidene)-hydrazino]-4-morpholin-4-yl-pyridin-2-yl}-(2-morpholin-4-yl-ethyl)-amine

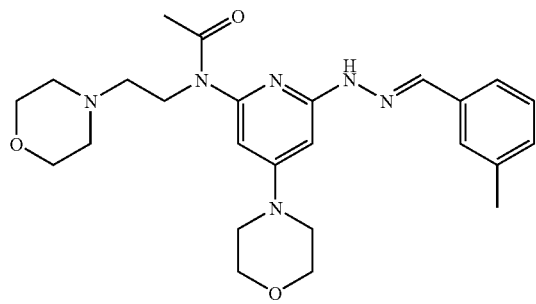

N-{6-[N'-(3-Methyl-benzylidene)-hydrazino]-4-morpholin-4-yl-pyridin-2-yl}-N-(2-morpholin-4-yl-ethyl)-acetamide

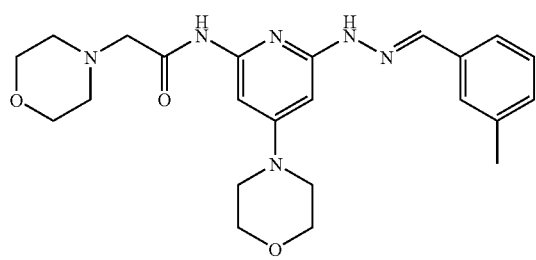

N-{6-[N'-(3-Methyl-benzylidene)-hydrazino]-4-morpholin-4-yl-pyridin-2-yl}-2-morpholin-4-yl-acetamide

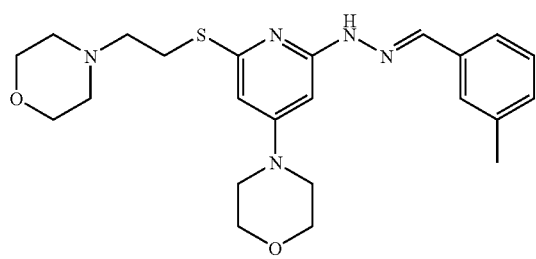

N-(3-Methyl-benzylidene)-N'-[4-morpholin-4-yl-6-(2-morpholin-4-yl-ethylsulfanyl)-pyridin-2-yl]-hydrazine

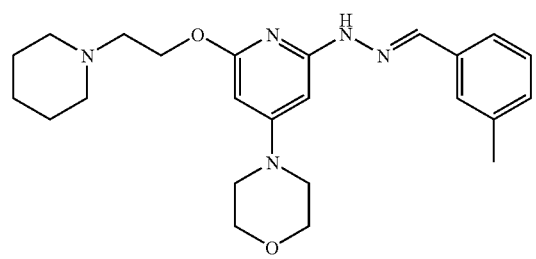

N-(3-Methyl-benzylidene)-N'-[4-morpholin-4-yl-6-(2-piperidin-1-yl-ethoxy)-pyridin-2-yl]-hydrazine

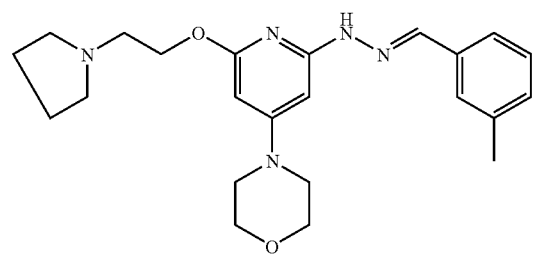

N-(3-Methyl-benzylidene)-N'-[4-morpholin-4-yl-6-(2-pyrrolidin-1-yl-ethoxy)-pyridin-2-yl]-hydrazine

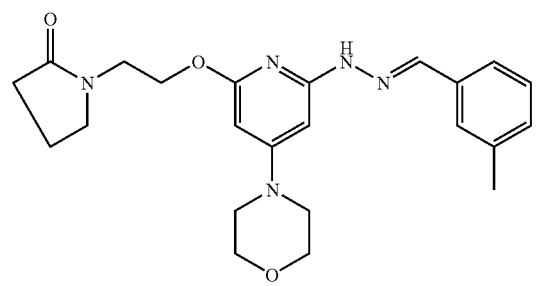

1-(2-{6-[N'-(3-Methyl-benzylidene)-hydrazino]-4-morpholin-4-yl-pyridin-2-yloxy}-ethyl)-pyrrolidin-2-one

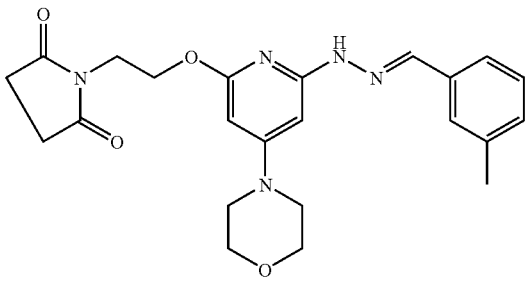

1-(2-{6-[N'-(3-Methyl-benzylidene)-hydrazino]-4-morpholin-4-yl-pyridin-2-yloxy}-ethyl)-pyrrolidine-2,5-dione

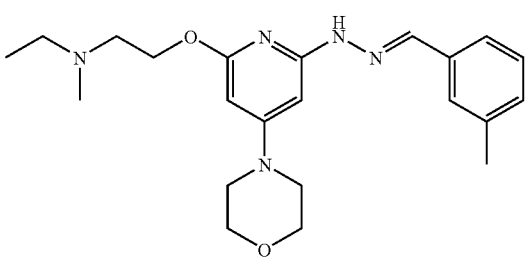

Ethyl-methyl-(2-{6-[N'-(3-methyl-benzylidene)-hydrazino]-4-morpholin-4-yl-pyridin-2-yloxy}-ethyl)-amine

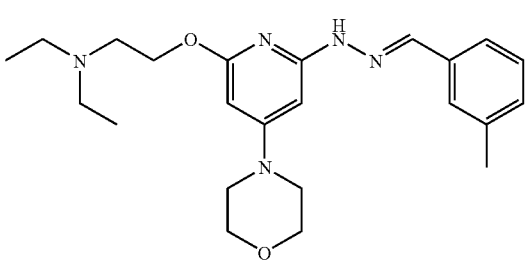

Diethyl-(2-{6-[N'-(3-methyl-benzylidene)-hydrazino]-4-morpholin-4-yl-pyridin-2-yloxy}-ethyl)-amine

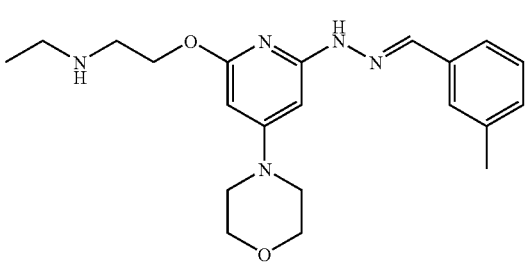

Ethyl-(2-{6-[N'-(3-methyl-benzylidene)-hydrazino]-4-morpholin-4-yl-pyridin-2-yloxy}-ethyl)-amine

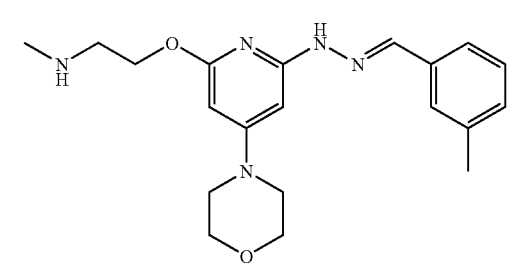

Methyl-(2-{6-[N'-(3-methyl-benzylidene)-hydrazino]-4-morpholin-4-yl-pyridin-2-yloxy}-ethyl)-amine

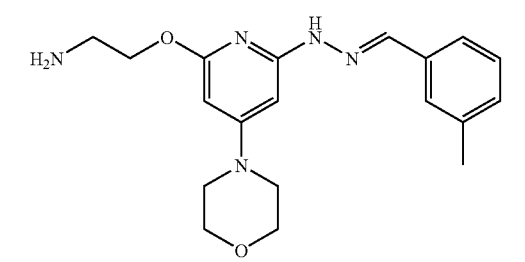

2-{6-[N'-(3-Methyl-benzylidene)-hydrazino]-4-morpholin-4-yl-pyridin-2-yloxy}-ethylamine -continued

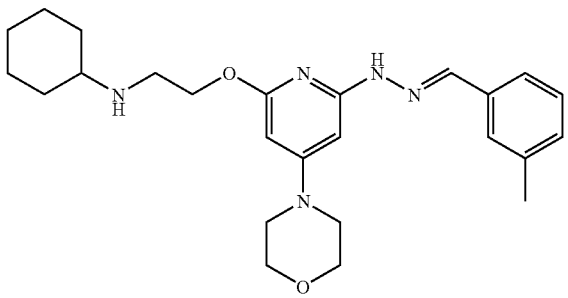

Cyclohexyl-(2-{6-[N'-(3-methyl-benzylidene)-hydrazino]-4-morpholin-4-yl-pyridin-2-yloxy}-ethyl)-amine

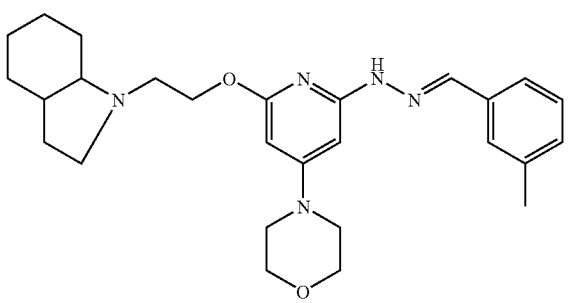

N-(3-Methyl-benzylidene)-N'-{4-morpholin-4-yl-6-[2-(octahydro-indol-1-yl)-ethoxy]-pyridin-2-yl}-hydrazine

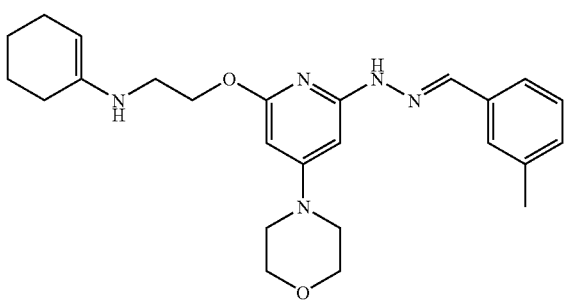

Cyclohex-1-enyl-(2-{6-[N'-(3-methyl-benzylidene)-hydrazino]-4-morpholin-4-yl-pyridin-2-yloxy}-ethyl)-amine

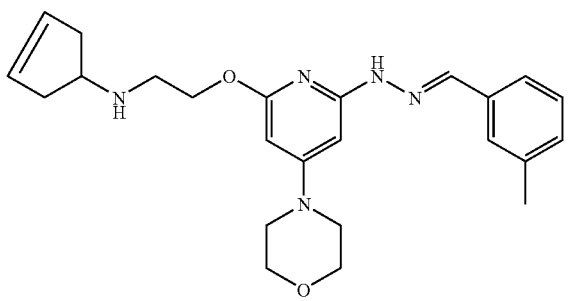

Cyclopent-3-enyl-(2-{6-[N'-(3-methyl-benzylidene)-hydrazino]-4-morpholin-4-yl-pyridin-2-yloxy}-ethyl)-amine

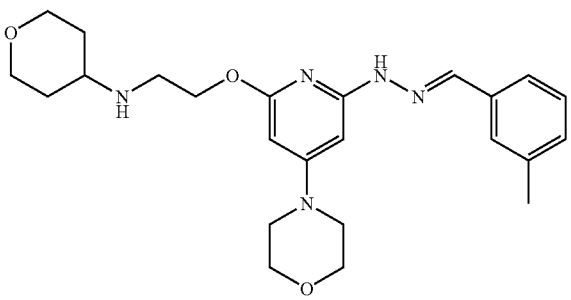

(2-{6-[N'-(3-Methyl-benzylidene)-hydrazino]-4-morpholin-4-yl-pyridin-2-yloxy}-ethyl)-(tetrahydro-pyran-4-yl)-amine

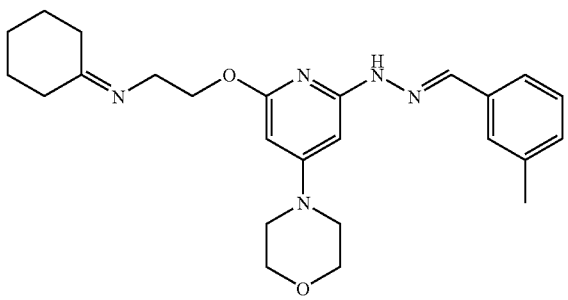

Cyclohexylidene-(2-{6-[N'-(3-methyl-benzylidene)-hydrazino]-4-morpholin-4-yl-pyridin-2-yloxy}-ethyl)-amine

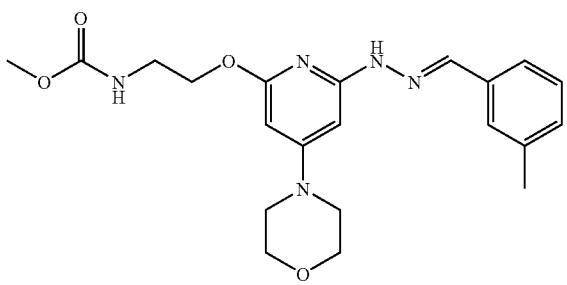

(2-{6-[N'-(3-Methyl-benzylidene)-hydrazino]-4-morpholin-4-yl-pyridin-2-yloxy}-ethyl)-carbamic acid methyl ester

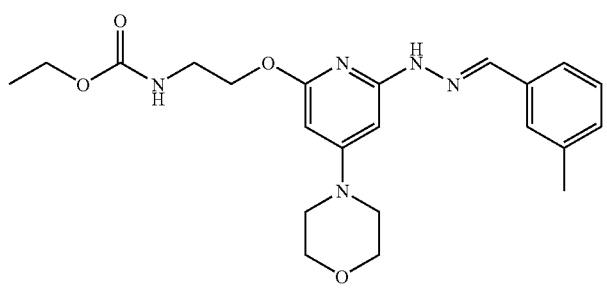

(2-{6-[N'-(3-Methyl-benzylidene)-hydrazino]-4-morpholin-4-yl-pyridin-2-yloxy}-ethyl)-carbamic acid ethyl ester

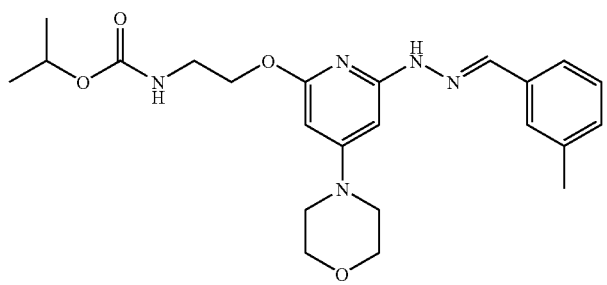

(2-{6-[N'-(3-Methyl-benzylidene)-hydrazino]-4-morpholin-4-yl-pyridin-2-yloxy}-ethyl)-carbamic acid isopropyl ester

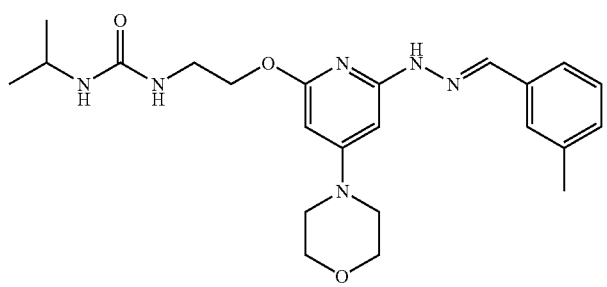

1-Isopropyl-3-(2-{6-[N'-(3-methyl-benzylidene)-hydrazino]-4-morpholin-4-yl-pyridin-2-yloxy}-ethyl)-urea

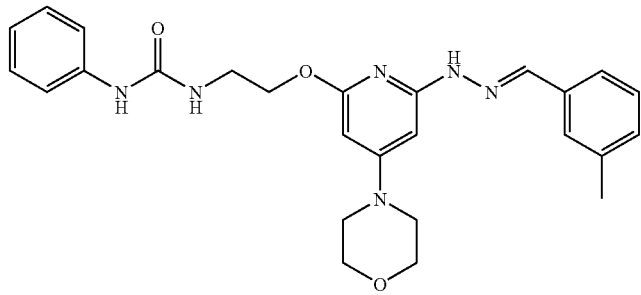

1-(2-{6-[N'-(3-Methyl-benzylidene)-hydrazino]-4-morpholin-4-yl-pyridin-2-yloxy}-ethyl)-3-phenyl-urea

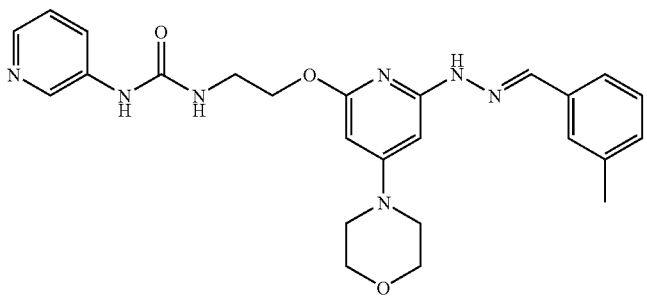

1-(2-{6-[N'-(3-Methyl-benzylidene)-hydrazino]-4-morpholin-4-yl-pyridin-2-yloxy}-ethyl)-3-pyridin-3-yl-urea

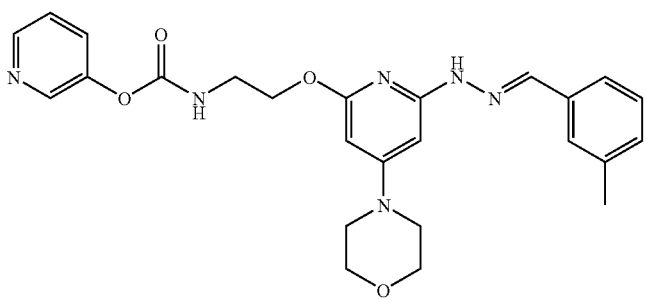

(2-{6-[N'-(3-Methyl-benzylidene)-hydrazino]-4-morpholin-4-yl-pyridin-2-yloxy}-ethyl)-carbamic acid pyridin-3-yl ester

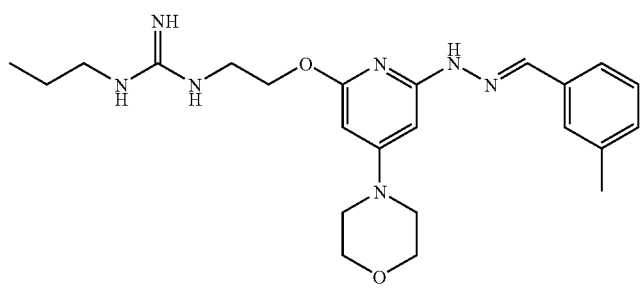

N-(2-{6-[N'-(3-Methyl-benzylidene)-hydrazino]-4-morpholin-4-yl-pyridin-2-yloxy}-ethyl)-N'-propyl guanidine

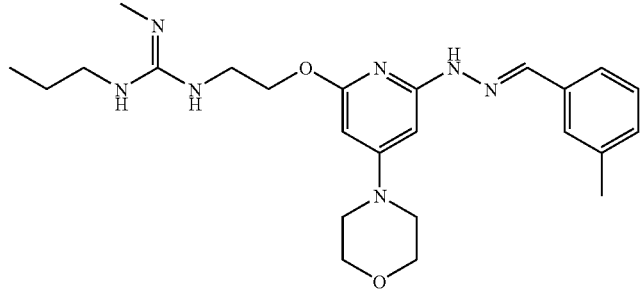

N-Methyl-N'-(2-{6-[N'-(3-methyl-benzylidene)-hydrazino]-4-morpholin-4-yl-pyridin-2-yloxy}-ethyl)-N''-propyl-guanidine -continued

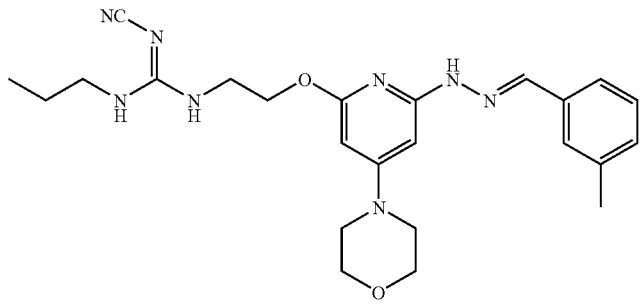

N-Cyano-N'-(2-{6-[N'-(3-methyl-benzylidene)-hydrazino]-4-morpholin-4-yl-pyridin-2-yloxy}-ethyl)-N''-propyl-guanidine

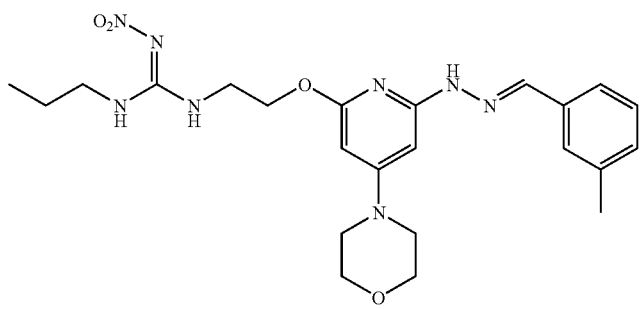

N-Nitro-N'-(2-{6-[N'-(3-methyl-benzylidene)-hydrazino]-4-morpholin-4-yl-pyridin-2-yloxy}-ethyl)-N''-propyl-guanidine

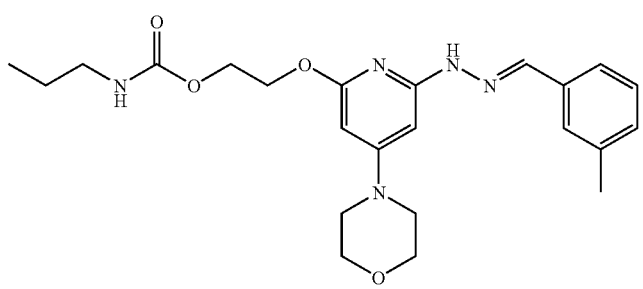

Propyl-carbamic acid 2-{6-[N'-(3-methyl-benzylidene)-hydrazino]-4-morpholin-4-yl-pyridin-2-yloxy}-ethyl ester

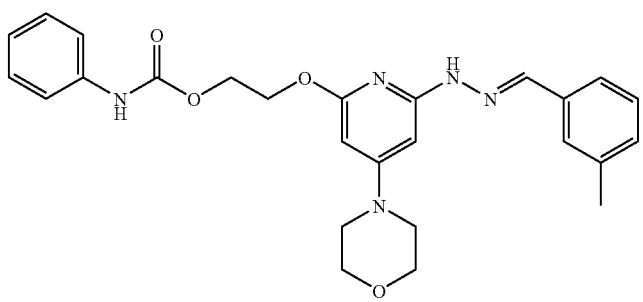

Phenyl-carbamic acid 2-{6-[N'-(3-methyl-benzylidene)-hydrazino]-4-morpholin-4-yl-pyridin-2-yloxy}-ethyl ester

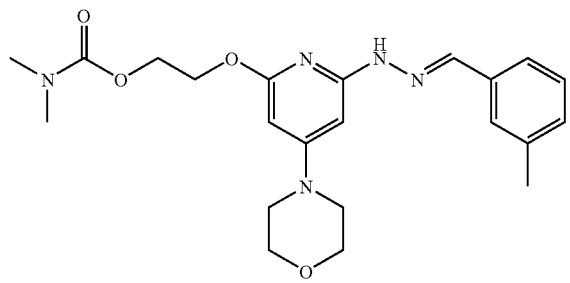

Dimethyl-carbamic acid 2-{6-[N'-(3-methyl-benzylidene)-hydrazino]-4-morpholin-4-yl-pyridin-2-yloxy}-ethyl ester -continued

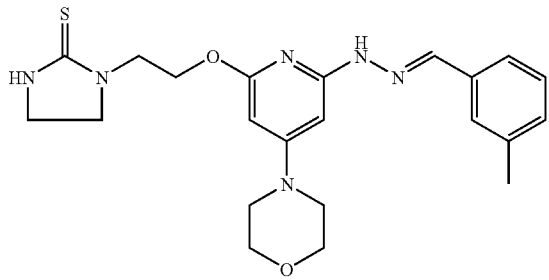

1-(2-{6-[N'-(3-Methyl-benzylidene)-hydrazino]-4-morpholin-4-yl-pyridin-2-yloxy}-ethyl)-imidazolidine-2-thione

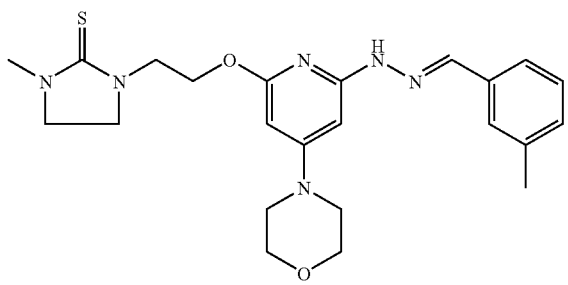

1-Methyl-3-(2-{6-[N'-(3-methyl-benzylidene)-hydrazino]-4-morpholin-4-yl-pyridin-2-yloxy}-ethyl)-imidazolidine-2-thione

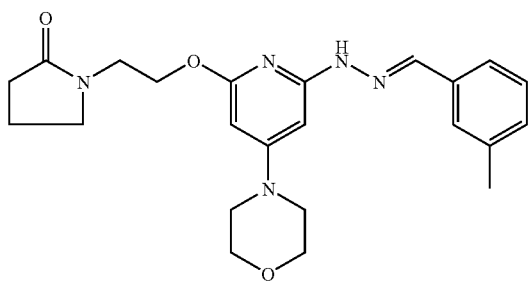

1-(2-{6-[N'-(3-Methyl-benzylidene)-hydrazino]-4-morpholin-4-yl-pyridin-2-yloxy}-ethyl)-pyrrolidin-2-one

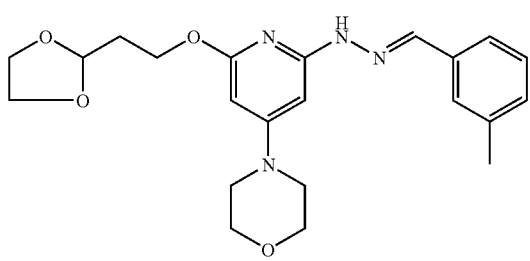

N-[6-(2-[1,3]Dioxolan-2-yl-ethoxy)-4-morpholin-4-yl-pyridin-2-yl]-N'-(3-methyl-benzylidene)-hydrazine

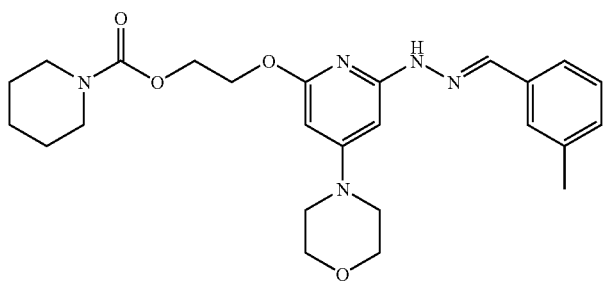

Piperidine-1-carboxylic acid 2-{6-[N'-(3-methyl-benzylidene)-hydrazino]-4-morpholin-4-yl-pyridin-2-yloxy}-ethyl ester

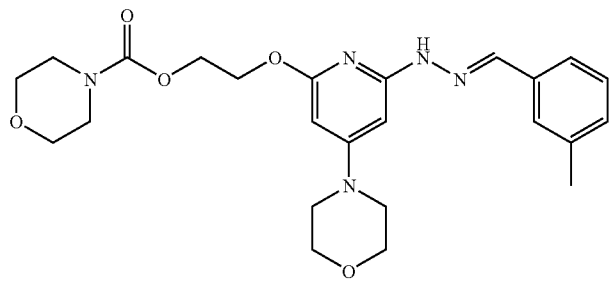

Morpholine-4-carboxylic acid 2-{6-[N'-(3-methyl-benzylidene)-hydrazino]-4-morpholin-4-yl-pyridin-2-yloxy}-ethyl ester

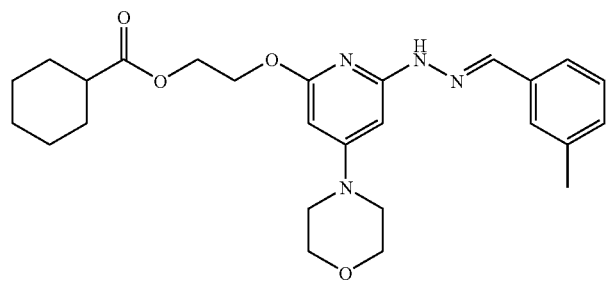

Cyclohexanecarboxylic acid 2-{6-[N'-(3-methyl-benzylidene)-hydrazino]-4-morpholin-4-yl-pyridin-2-yloxy}-ethyl ester

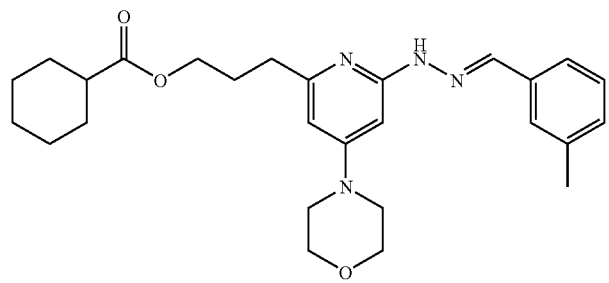

Cyclohexanecarboxylic acid 3-{6-[N'-(3-methyl-benzylidene)-hydrazino]-4-morpholin-4-yl-pyridin-2-yl}-propyl ester

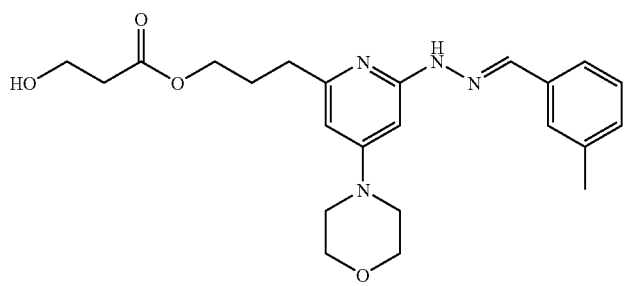

3-Hydroxy-propionic acid 3-{6-[N'-(3-methyl-benzylidene)-hydrazino]-4-morpholin-4-yl-pyridin-2-yl}-propyl ester

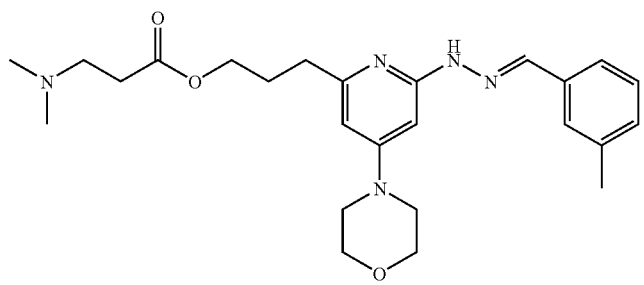

3-Dimethylamino-propionic acid 3-{6-[N'-(3-methyl-benzylidene)-hydrazino]-4-morpholin-4-yl-pyridin-2-yl}-propyl ester

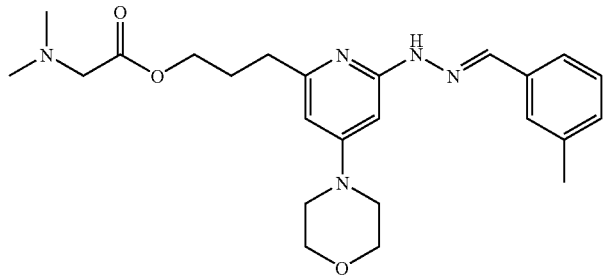

Dimethylamino-acetic acid 3-{6-[N'-(3-methyl-benzylidene)-hydrazino]-4-morpholin-4-yl-pyridin-2-yl}-propyl ester

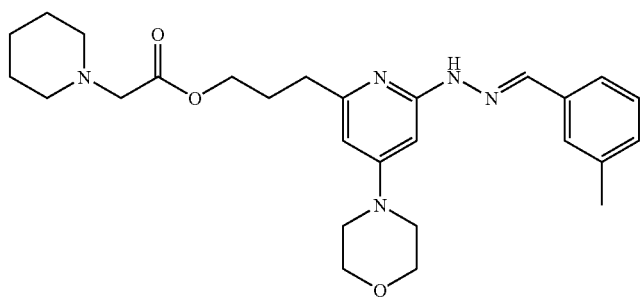

Piperidin-1-yl-acetic acid 3-{6-[N'-(3-methyl-benzylidene)-hydrazino]-4-morpholin-4-yl-pyridin-2-yl}-propyl ester

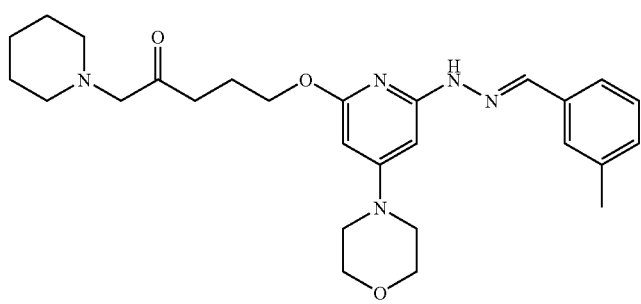

5-{6-[N'-(3-Methyl-benzylidene)-hydrazino]-4-morpholin-4-yl-pyridin-2-yloxy}-1-piperidin-1-yl-pentan-2-one

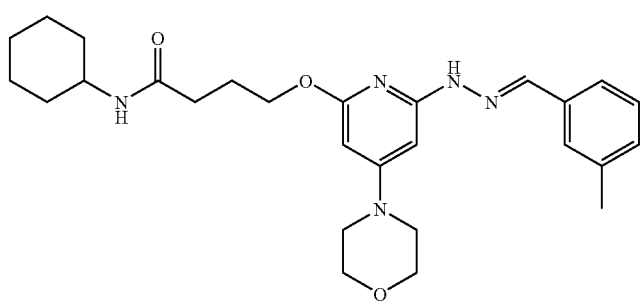

N-Cyclohexyl-4-{6-[N'-(3-methyl-benzylidene)-hydrazino]-4-morpholin-4-yl-pyridin-2-yloxy}-butyramide

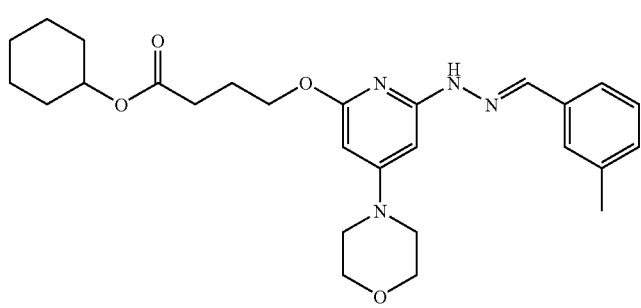

4-{6-[N'-(3-Methyl-benzylidene)-hydrazino]-4-morpholin-4-yl-pyridin-2-yloxy}-butyric acid cyclohexyl ester -continued

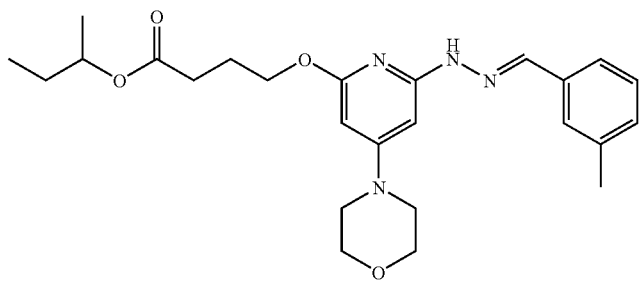

4-{6-[N'-(3-Methyl-benzylidene)-hydrazino]-4-morpholin-4-yl-pyridin-2-yloxy}-butyric acid sec-butyl ester

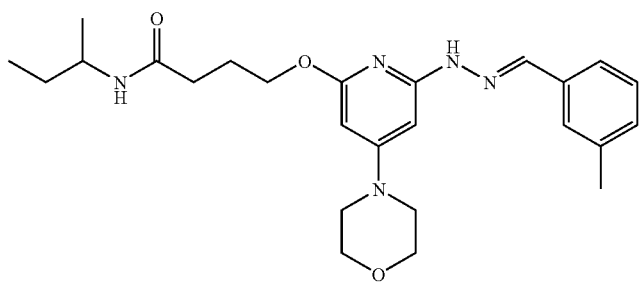

N-sec-Butyl-4-{6-[N'-(3-methyl-benzylidene)-hydrazino]-4-morpholin-4-yl-pyridin-2-yloxy}-butyramide

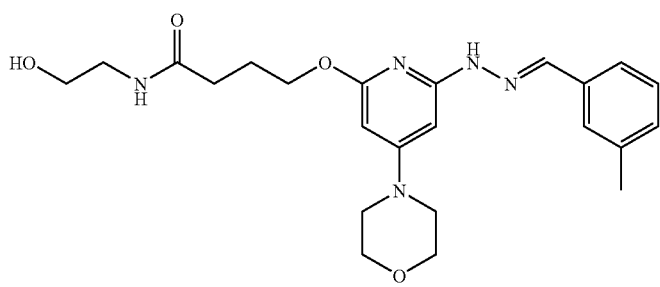

N-(2-Hydroxy-ethyl)-4-{6-[N'-(3-methyl-benzylidene)-hydrazino]-4-morpholin-4-yl-pyridin-2-yloxy}-butyramide

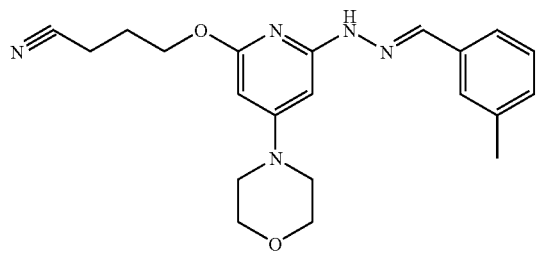

4-{6-[N'-(3-Methyl-benzylidene)-hydrazino]-4-morpholin-4-yl-pyridin-2-yloxy}-butyronitrile

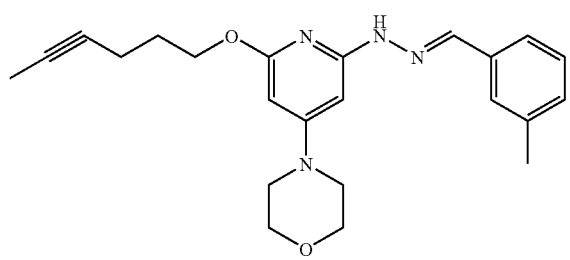

N-(6-Hex-4-ynyloxy-4-morpholin-4-yl-pyridin-2-yl)-N'-(3-methyl-benzylidene)-hydrazine

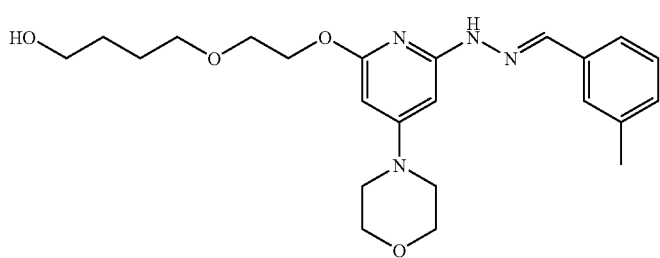

4-(2-{6-[N'-(3-Methyl-benzylidene)-hydrazino]-4-morpholin-4-yl-pyridin-2-yloxy}-ethoxy)-butan-1-ol

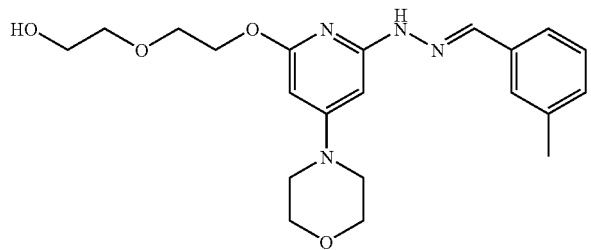

2-(2-{6-[N'-(3-Methyl-benzylidene)-hydrazino]-4-morpholin-4-yl-pyridin-2-yloxy}-ethoxy)-ethanol

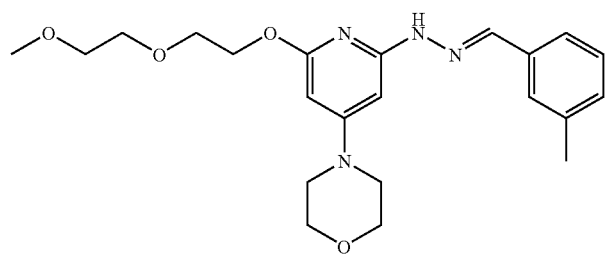

N-{6-[2-(2-Methoxy-ethoxy)-ethoxy]-4-morpholin-4-yl-pyridin-2-yl}-N'-(3-methyl-benzylidene)-hydrazine

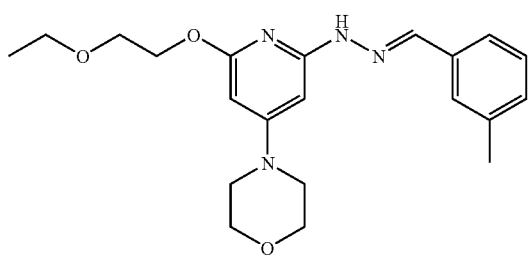

N-[6-(2-Ethoxy-ethoxy)-4-morpholin-4-yl-pyridin-2-yl]-N'-(3-methyl-benzylidene)-hydrazine

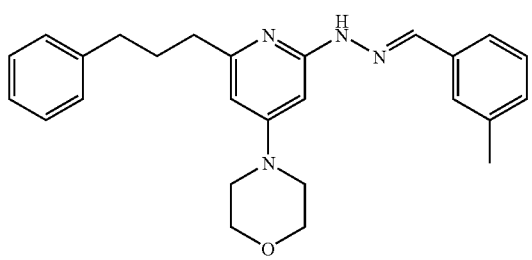

N-(3-Methyl-benzylidene)-N'-[4-morpholin-4-yl-6-(3-phenyl-propyl)-pyridin-2-yl]-hydrazine

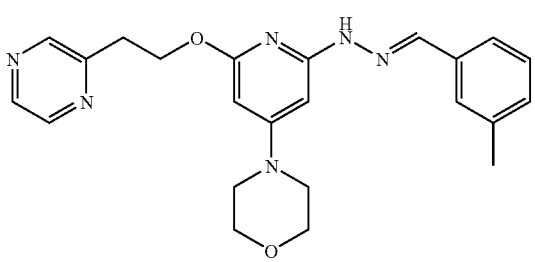

N-(3-Methyl-benzylidene)-N'-[4-morpholin-4-yl-6-(2-pyrazin-2-yl-ethoxy)-pyridin-2-yl]-hydrazine

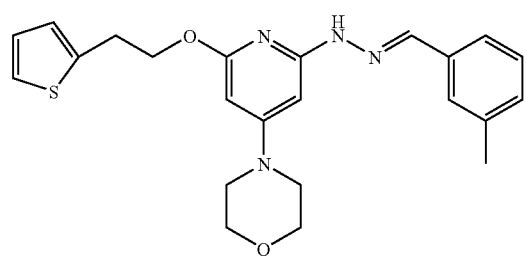

N-(3-Methyl-benzylidene)-N'-[4-morpholin-4-yl-6-(2-thiophen-2-yl-ethoxy)-pyridin-2-yl]-hydrazine

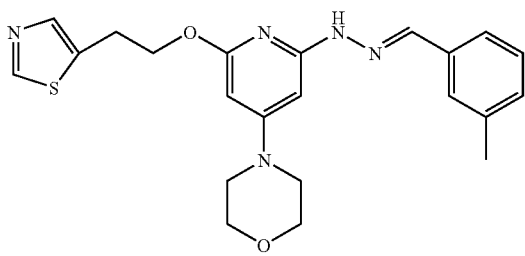

N-(3-Methyl-benzylidene)-N'-[4-morpholin-4-yl-6-(2-thiazol-5-yl-ethoxy)-pyridin-2-yl]-hydrazine

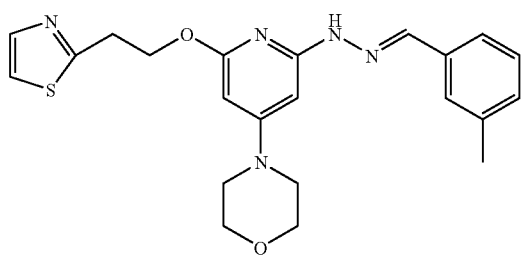

N-(3-Methyl-benzylidene)-N'-[4-morpholin-4-yl-6-(2-thiazol-2-yl-ethoxy)-pyridin-2-yl]-hydrazine

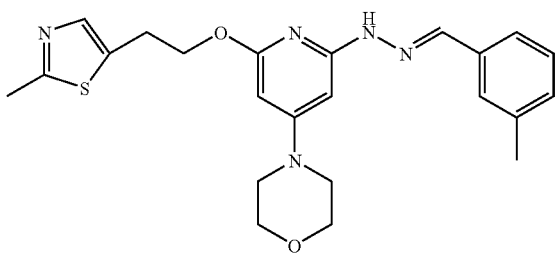

N-(3-Methyl-benzylidene)-N'-{6-[2-(2-methyl-thiazol-5-yl)-ethoxy]-4-morpholin-4-yl-pyridin-2-yl}-hydrazine

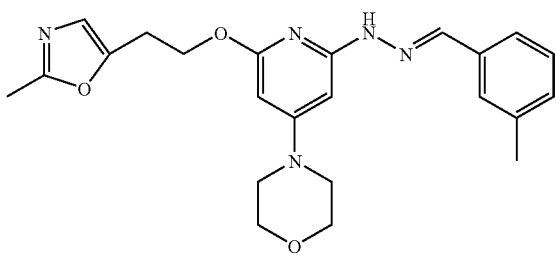

N-(3-Methyl-benzylidene)-N'-{6-[2-(2-methyl-oxazol-5-yl)-ethoxy]-4-morpholin-4-yl-pyridin-2-yl}-hydrazine

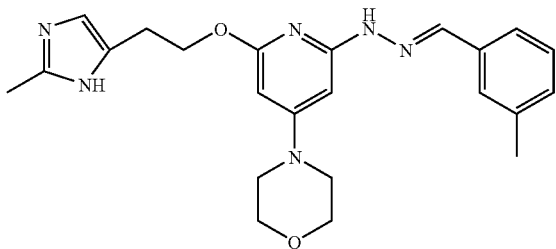

N-(3-Methyl-benzylidene)-N'-{6-[2-(2-methyl-3H-imidazol-4-yl)-ethoxy]-4-morpholin-4-yl-pyridin-2-yl}-hydrazine

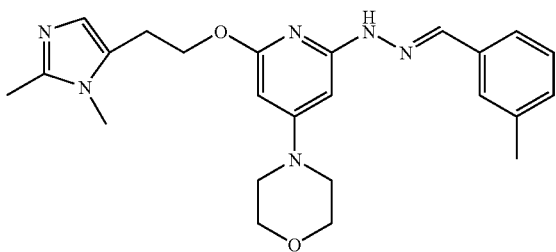

N-{6-[2-(2,3-Dimethyl-3H-imidazol-4-yl)-ethoxy]-4-morpholin-4-yl-pyridin-2-yl}-N'-(3-methyl-benzylidene)-hydrazine

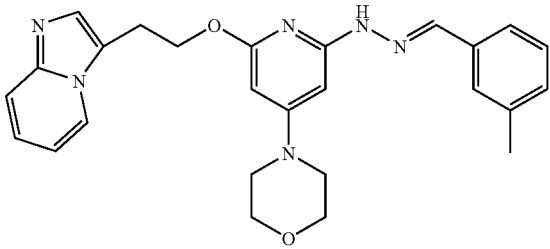 N-[6-(2-Imidazo[1,2-a]pyridin-3-yl-ethoxy)-4-morpholin-4-yl-pyridin-2-yl]-N'-(3-methyl-benzylidene)-hydrazine

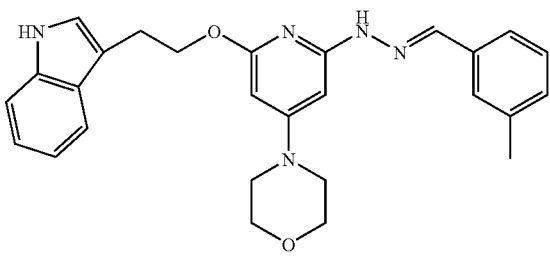 N-{6-[2-(1H-Indol-3-yl)-ethoxy]-4-morpholin-4-yl-pyridin-2-yl}-N'-(3-methyl-benzylidene)-hydrazine

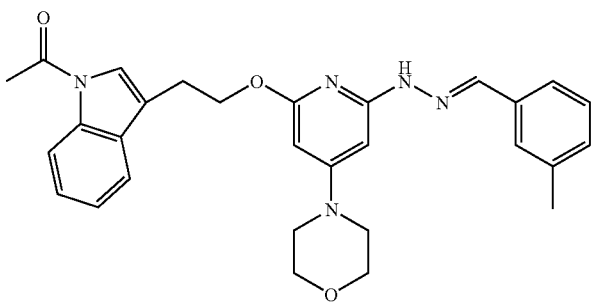 1-[3-(2-{6-[N'-(3-Methyl-benzylidene)-hydrazino]-4-morpholin-4-yl-pyridin-2-yloxy}-ethyl)-indol-1-yl]-ethanone

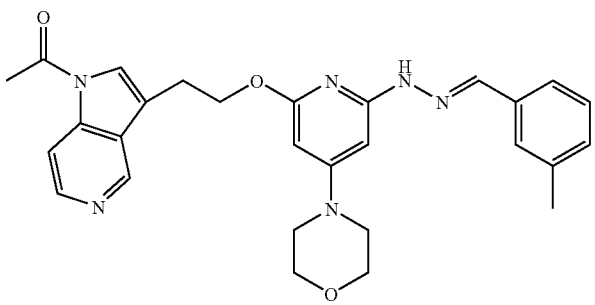 1-[3-(2-{6-[N'-(3-Methyl-benzylidene)-hydrazino]-4-morpholin-4-yl-pyridin-2-yloxy}-ethyl)-pyrrolo[3,2-c]pyridin-1-yl]-ethanone

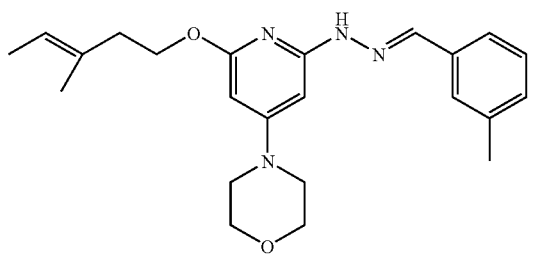 N-(3-Methyl-benzylidene)-N'-[6-(3-methyl-pent-3-enyloxy)-4-morpholin-4-yl-pyridin-2-yl]-hydrazine

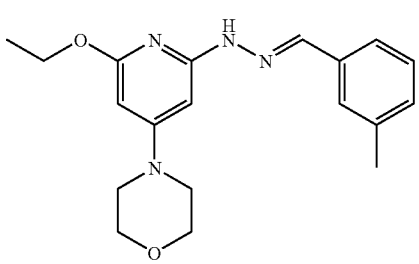 N-(6-Ethoxy-4-morpholin-4-yl-pyridin-2-yl)-N'-(3-methyl-benzylidene)-hydrazine

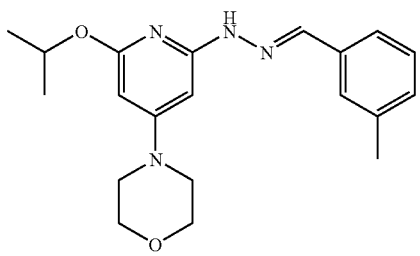 N-(6-Isopropoxy-4-morpholin-4-yl-pyridin-2-yl)-N'-(3-methyl-benzylidene)-hydrazine

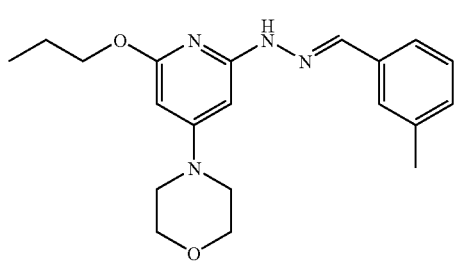 N-(3-Methyl-benzylidene)-N'-(4-morpholin-4-yl-6-propoxy-pyridin-2-yl)-hydrazine

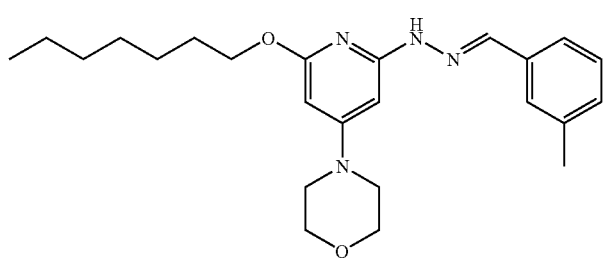 N-(6-Heptyloxy-4-morpholin-4-yl-pyridin-2-yl)-N'-(3-methyl-benzylidene)-hydrazine

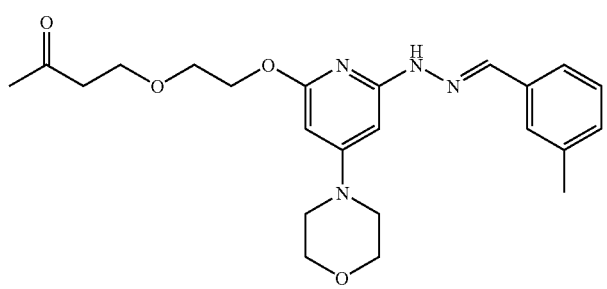 4-(2-{6-[N'-(3-Methyl-benzylidene)-hydrazino]-4-morpholin-4-yl-pyridin-2-yloxy}-ethoxy)-butan-2-one

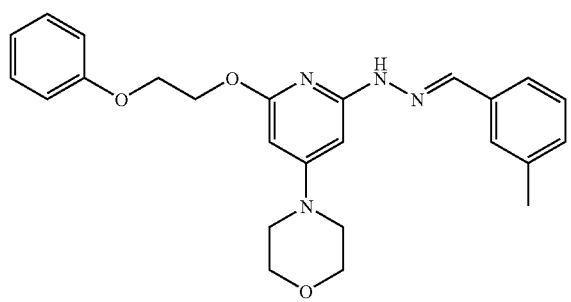 N-(3-Methyl-benzylidene)-N'-[4-morpholin-4-yl-6-(2-phenoxy-ethoxy)-pyridin-2-yl]-hydrazine

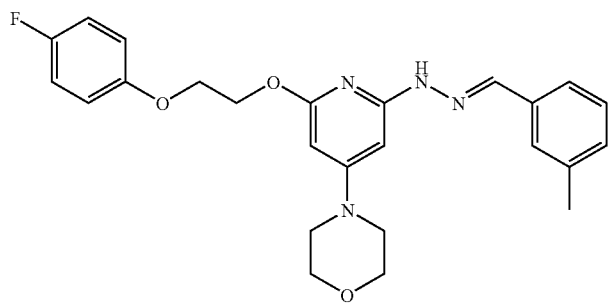

N-{6-[2-(4-Fluoro-phenoxy)-ethoxy]-4-morpholin-4-yl-pyridin-2-yl}-N'-(3-methyl-benzylidene)-hydrazine

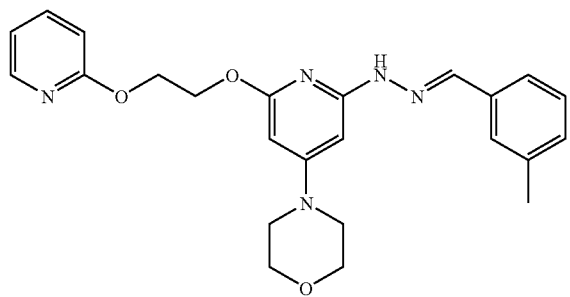

N-(3-Methyl-benzylidene)-N'-{4-morpholin-4-yl-6-[2-(pyridin-2-yloxy)-ethoxy]-pyridin-2-yl}-hydrazine

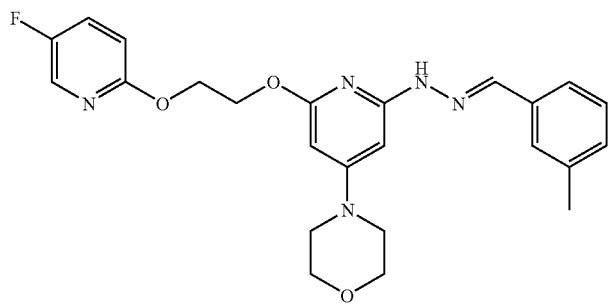

N-{6-[2-(5-Fluoro-pyridin-2-yloxy)-ethoxy]-4-morpholin-4-yl-pyridin-2-yl}-N'-(3-methyl-benzylidene)-hydrazine

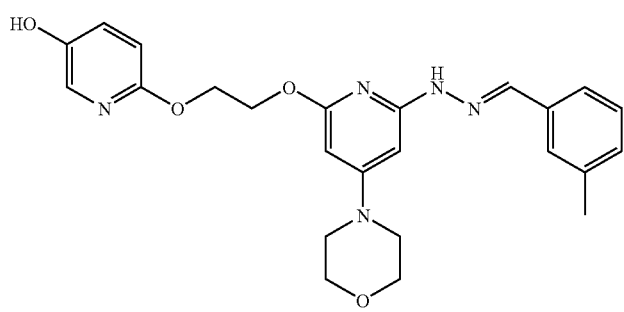

6-(2-{6-[N'-(3-Methyl-benzylidene)-hydrazino]-4-morpholin-4-yl-pyridin-2-yloxy}-ethoxy)-pyridin-3-ol

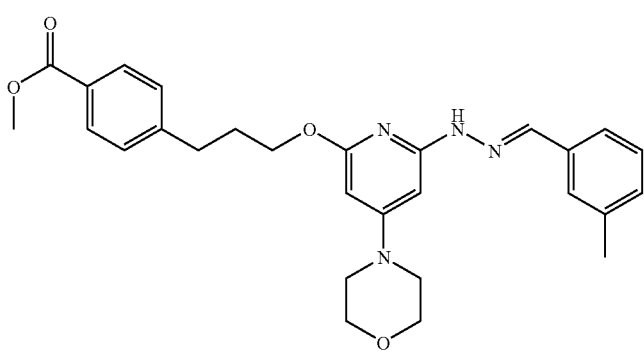

4-(3-{6-[N'-(3-Methyl-benzylidene)-hydrazino]-4-morpholin-4-yl-pyridin-2-yloxy}-propyl)-benzoic acid methyl ester -continued

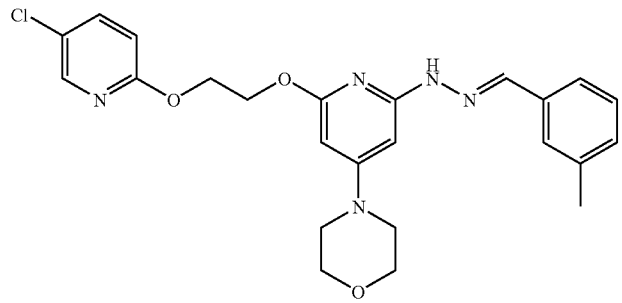

N-{6-[2-(5-Chloro-pyridin-2-yloxy)-ethoxy]-4-morpholin-4-yl-pyridin-2-yl}-N'-(3-methyl-benzylidene)-hydrazine

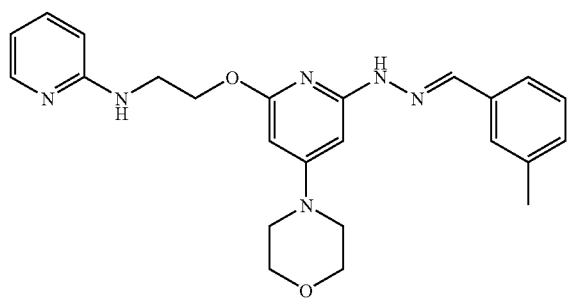

(2-{6-[N'-(3-Methyl-benzylidene)-hydrazino]-4-morpholin-4-yl-pyridin-2-yloxy}-ethyl)-pyridin-2-yl-amine

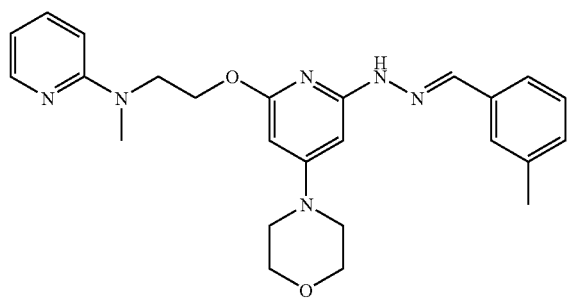

Methyl-(2-{6-[N'-(3-methyl-benzylidene)-hydrazino]-4-morpholin-4-yl-pyridin-2-yloxy}-ethyl)-pyridin-2-yl-amine

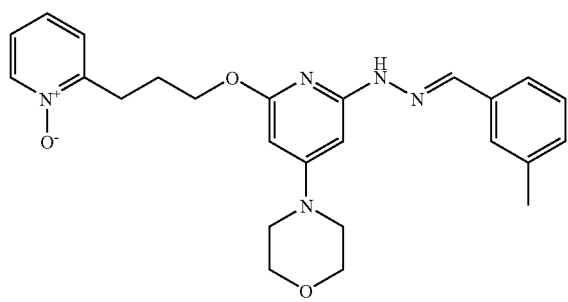

N-(3-Methyl-benzylidene)-N'-{4-morpholin-4-yl-6-[3-(1-oxy-pyridin-2-yl)-propoxy]-pyridin-2-yl}-hydrazine

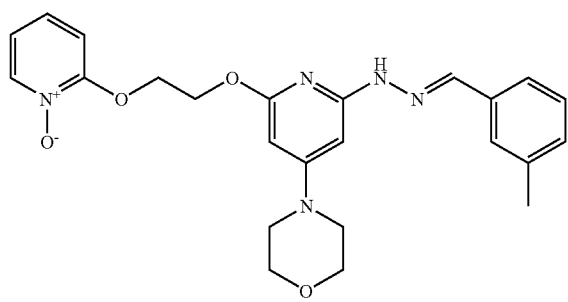

N-(3-Methyl-benzylidene)-N'-{4-morpholin-4-yl-6-[2-(1-oxy-pyridin-2-yloxy)-ethoxy]-pyridin-2-yl}-hydrazine -continued

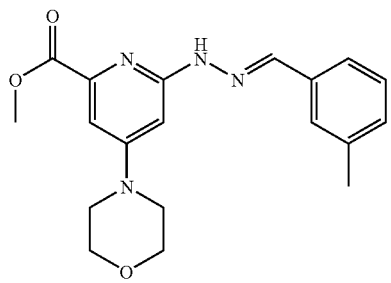
6-[N'-(3-Methyl-benzylidene)-hydrazino]-4-morpholin-4-yl-pyridine-2-carboxylic acid methyl ester

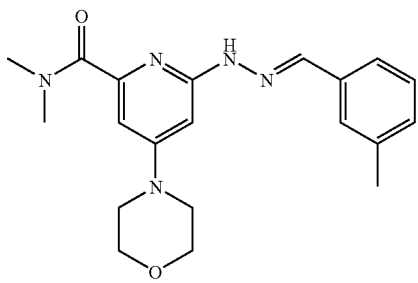
6-[N'-(3-Methyl-benzylidene)-hydrazino]-4-morpholin-4-yl-pyridine-2-carboxylic acid dimethylamide

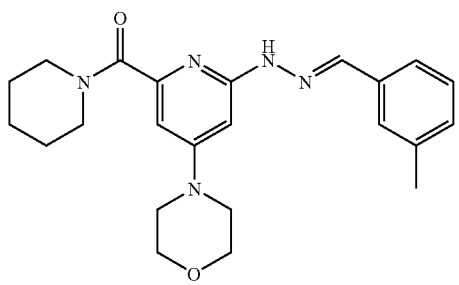
{6-[N'-(3-Methyl-benzylidene)-hydrazino]-4-morpholin-4-yl-pyridin-2-yl}-piperidin-1-yl-methanone

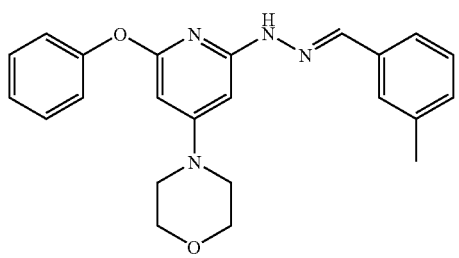
N-(3-Methyl-benzylidene)-N'-(4-morpholin-4-yl-6-phenoxy-pyridin-2-yl)-hydrazine

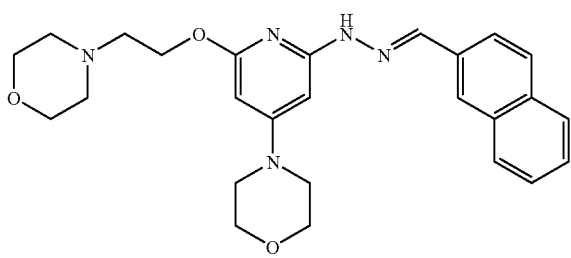
N-[4-Morpholin-4-yl-6-(2-morpholin-4-yl-ethoxy)-pyridin-2-yl]-N'-naphthalen-2-ylmethylene-hydrazine

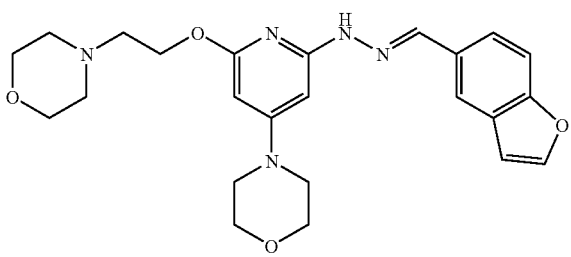
N-Benzofuran-5-ylmethylene-N'-[4-morpholin-4-yl-6-(2-morpholin-4-yl-ethoxy)-pyridin-2-yl]-hydrazine

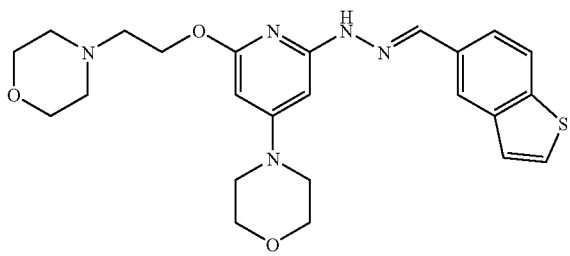

N-Benzo[b]thiophen-5-ylmethylene-N'-[4-morpholin-4-yl-6-(2-morpholin-4-yl-ethoxy)-pyridin-2-yl]-hydrazine

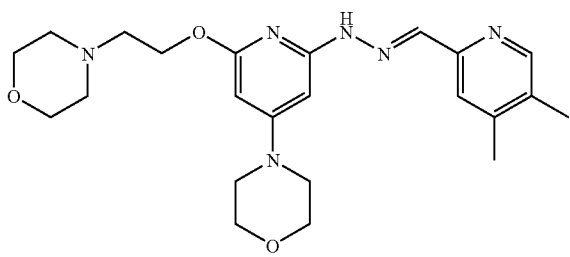

N-(4,5-Dimethyl-pyridin-2-ylmethylene)-N'-[4-morpholin-4-yl-6-(2-morpholin-4-yl-ethoxy)-pyridin-2-yl]-hydrazine

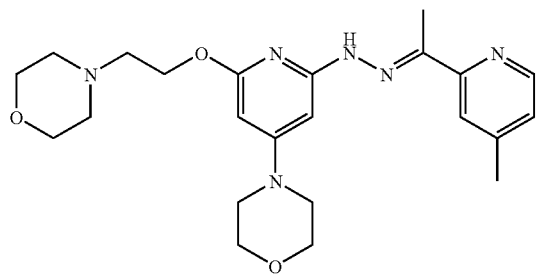

N-[1-(4-Methyl-pyridin-2-yl)-ethylidene]-N'-[4-morpholin-4-yl-6-(2-morpholin-4-yl-ethoxy)-pyridin-2-yl]-hydrazine

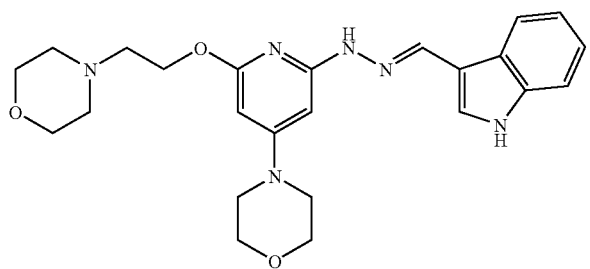

1H-Indole-3-carbaldehyde O-[4-morpholin-4-yl-6-(2-morpholin-4-yl-ethoxy)-pyridin-2-yl]-oxime

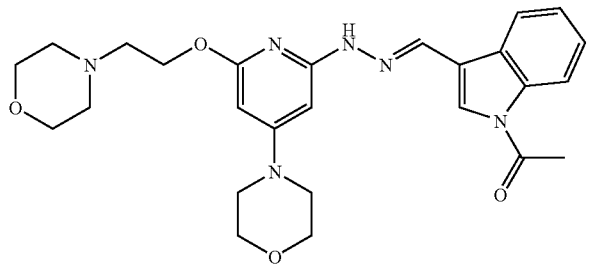

1-(3-{[4-Morpholin-4-yl-6-(2-morpholin-4-yl-ethoxy)-pyridin-2-yl]-hydrazonomethyl}-indol-1-yl)-ethanone

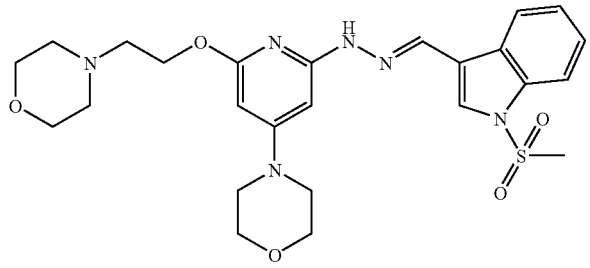

N-(1-Methanesulfonyl-1H-indol-3-ylmethylene)-N'-[4-morpholin-4-yl-6-(2-morpholin-4-yl-ethoxy)-pyridin-2-yl]-hydrazine

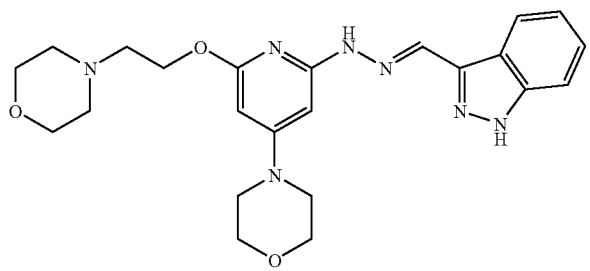

N-(1H-Indazol-3-ylmethylene)-N'-[4-morpholin-4-yl-6-(2-morpholin-4-yl-ethoxy)-pyridin-2-yl]-hydrazine

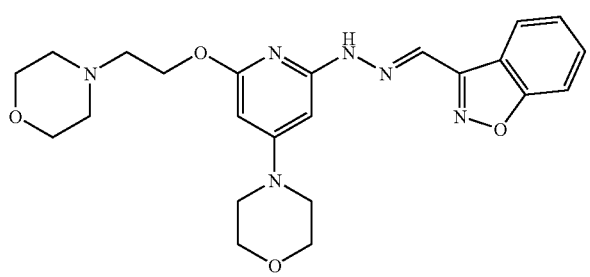

N-Benzo[d]isoxazol-3-ylmethylene-N'-[4-morpholin-4-yl-6-(2-morpholin-4-yl-ethoxy)-pyridin-2-yl]-hydrazine

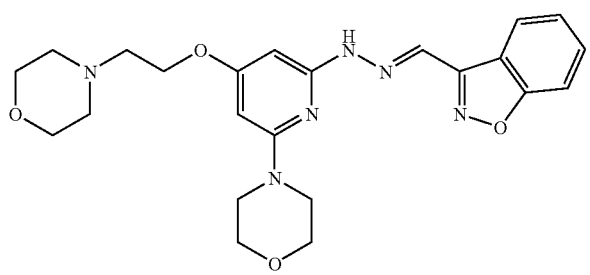

N-Benzo[d]isoxazol-3-ylmethylene-N'-[6-morpholin-4-yl-4-(2-morpholin-4-yl-ethoxy)-pyridin-2-yl]-hydrazine

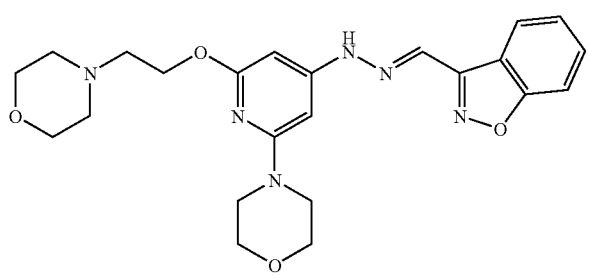

N-Benzo[d]isoxazol-3-ylmethylene-N'-[2-morpholin-4-yl-6-(2-morpholin-4-yl-ethoxy)-pyridin-4-yl]-hydrazine

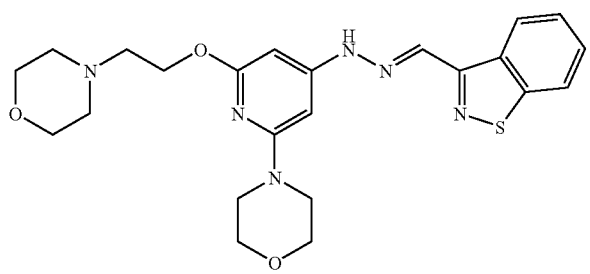

N-Benzo[d]isothiazol-3-ylmethylene-N'-[2-morpholin-4-yl-6-(2-morpholin-4-yl-ethoxy)-pyridin-4-yl]-hydrazine

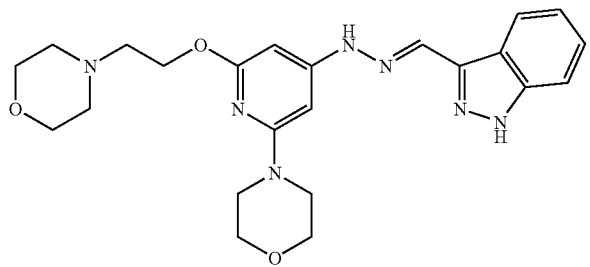

N-(1H-Indazol-3-ylmethylene)-N'-[2-morpholin-4-yl-6-(2-morpholin-4-yl-ethoxy)-pyridin-4-yl]-hydrazine

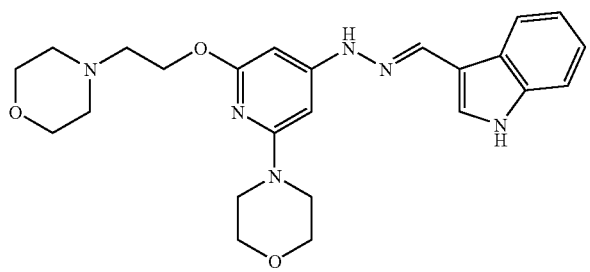

N-(1H-Indol-3-ylmethylene)-N'-[2-morpholin-4-yl-6-(2-morpholin-4-yl-ethoxy)-pyridin-4-yl]-hydrazine

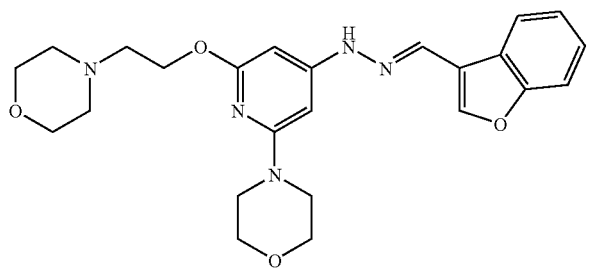

N-Benzofuran-3-ylmethylene-N'-[2-morpholin-4-yl-6-(2-morpholin-4-yl-ethoxy)-pyridin-4-yl]-hydrazine

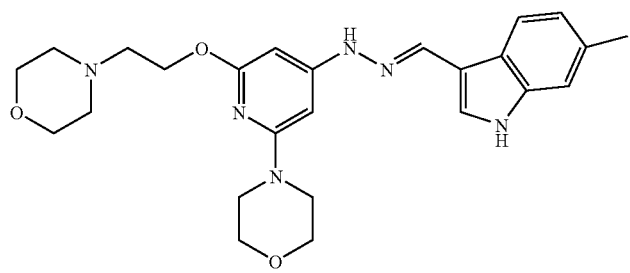

N-(6-Methyl-1H-indol-3-ylmethylene)-N'-[2-morpholin-4-yl-6-(2-morpholin-4-yl-ethoxy)-pyridin-4-yl]-hydrazine

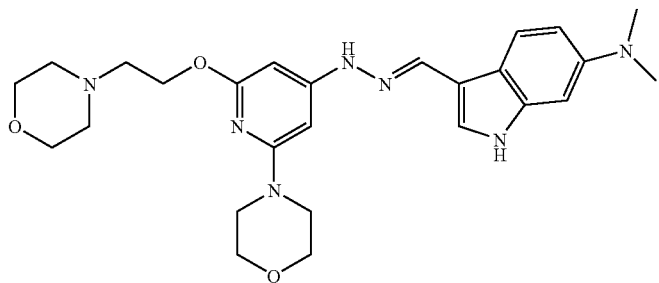

Dimethyl-(3-{[2-morpholin-4-yl-6-(2-morpholin-4-yl-ethoxy)-pyridin-4-yl]-hydrazonomethyl}-1H-indol-6-yl)-amine

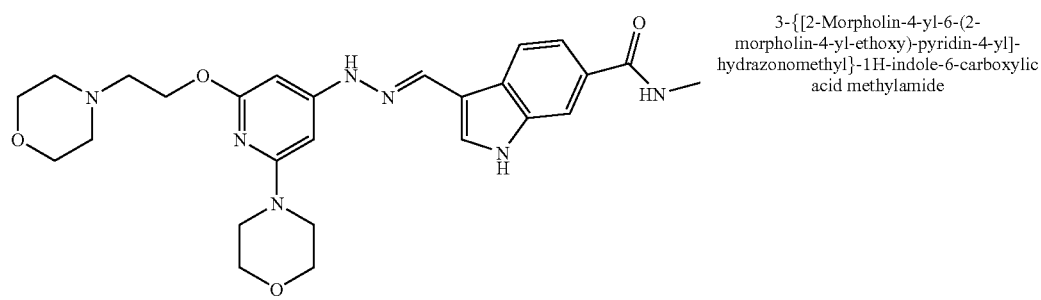

3-{[2-Morpholin-4-yl-6-(2-morpholin-4-yl-ethoxy)-pyridin-4-yl]-hydrazonomethyl}-1H-indole-6-carboxylic acid methylamide

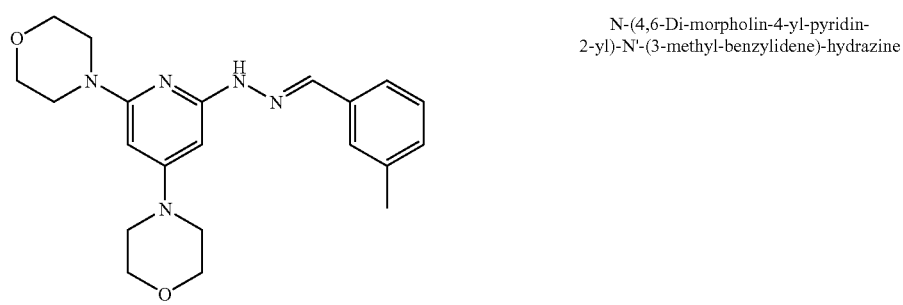

N-(4,6-Di-morpholin-4-yl-pyridin-2-yl)-N'-(3-methyl-benzylidene)-hydrazine

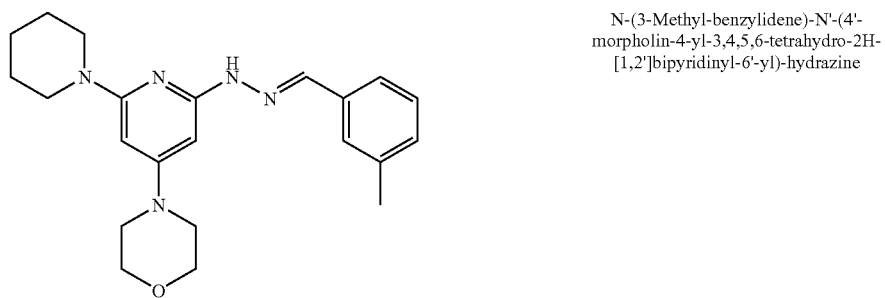

N-(3-Methyl-benzylidene)-N'-(4'-morpholin-4-yl-3,4,5,6-tetrahydro-2H-[1,2']bipyridinyl-6'-yl)-hydrazine

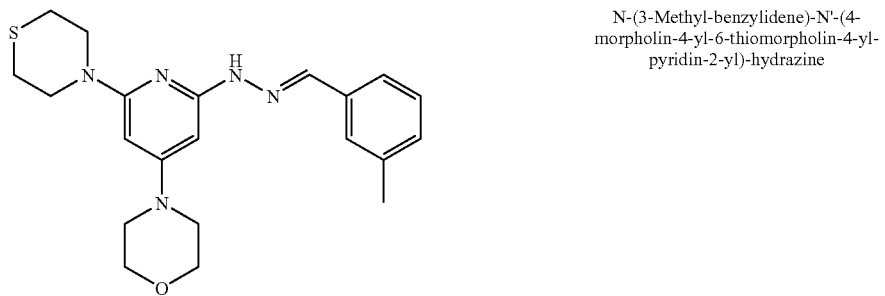

N-(3-Methyl-benzylidene)-N'-(4-morpholin-4-yl-6-thiomorpholin-4-yl-pyridin-2-yl)-hydrazine

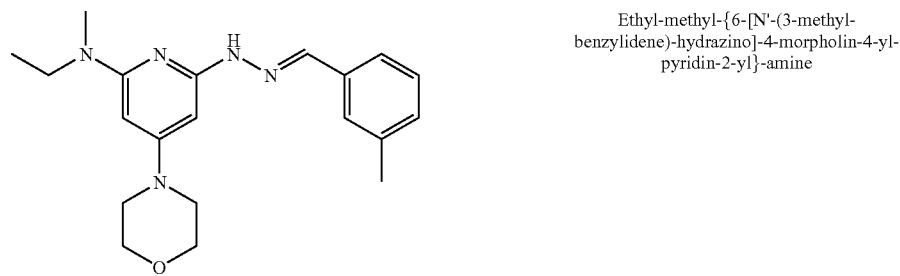

Ethyl-methyl-{6-[N'-(3-methyl-benzylidene)-hydrazino]-4-morpholin-4-yl-pyridin-2-yl}-amine

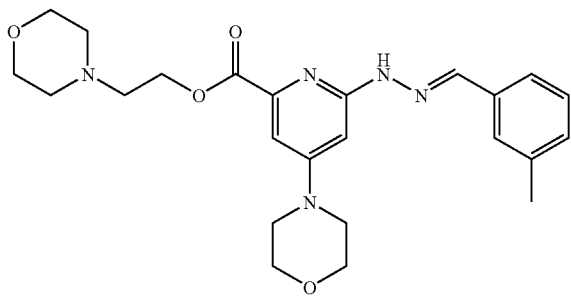

6-[N'-(3-Methyl-benzylidene)-hydrazino]-4-morpholin-4-yl-pyridine-2-carboxylic acid 2-morpholin-4-yl-ethyl ester

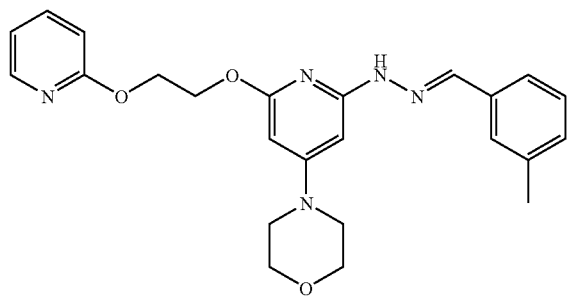

N-(3-Methyl-benzylidene)-N'-{4-morpholin-4-yl-6-[2-(pyridin-2-yloxy)-ethoxy]-pyridin-2-yl}-hydrazine

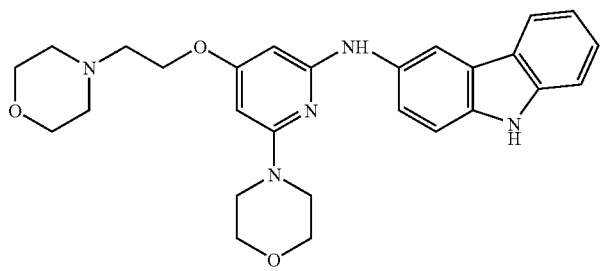

(9H-Carbazol-3-yl)-[6-morpholin-4-yl-4-(2-morpholin-4-yl-ethoxy)-pyridin-2-yl]-amine

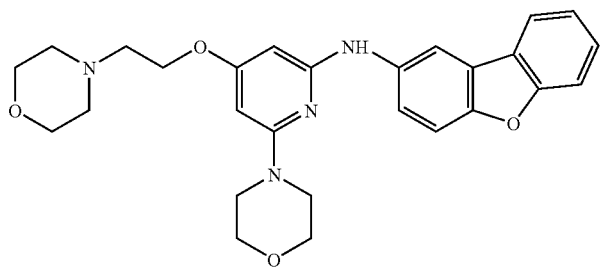

Dibenzofuran-2-yl-[6-morpholin-4-yl-4-(2-morpholin-4-yl-ethoxy)-pyridin-2-yl]-amine

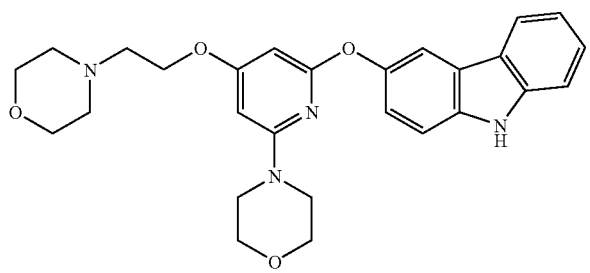

3-[6-Morpholin-4-yl-4-(2-morpholin-4-yl-ethoxy)-pyridin-2-yloxy]-9H-carbazole

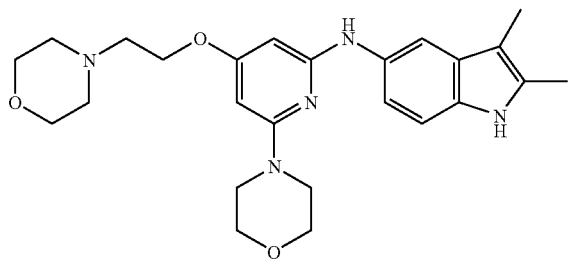

(2,3-Dimethyl-1H-indol-5-yl)-[6-morpholin-4-yl-4-(2-morpholin-4-yl-ethoxy)-pyridin-2-yl]-amine

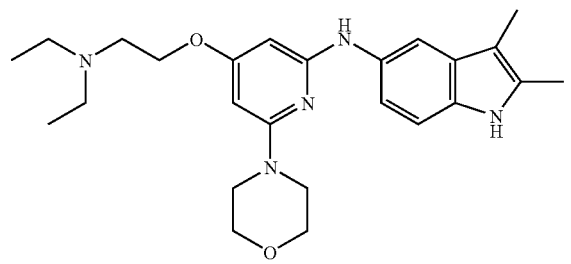

[4-(2-Diethylamino-ethoxy)-6-morpholin-4-yl-pyridin-2-yl]-(2,3-dimethyl-1H-indol-5-yl)-amine

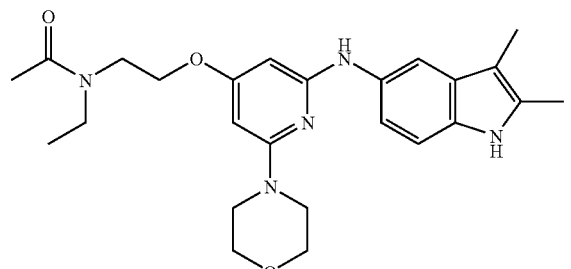

N-{2-[2-(2,3-Dimethyl-1H-indol-5-ylamino)-6-morpholin-4-yl-pyridin-4-yloxy]-ethyl}-N-ethyl-acetamide

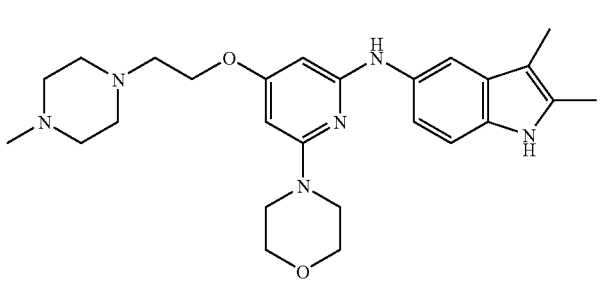

(2,3-Dimethyl-1H-indol-5-yl)-{4-[2-(4-methyl-piperazin-1-yl)-ethoxy]-6-morpholin-4-yl-pyridin-2-yl}-amine

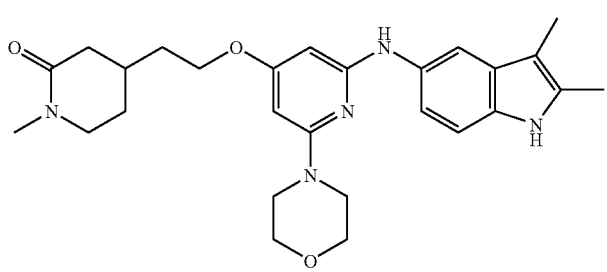

4-{2-[2-(2,3-Dimethyl-1H-indol-5-ylamino)-6-morpholin-4-yl-pyridin-4-yloxy]-ethyl}-1-methyl-piperidin-2-one

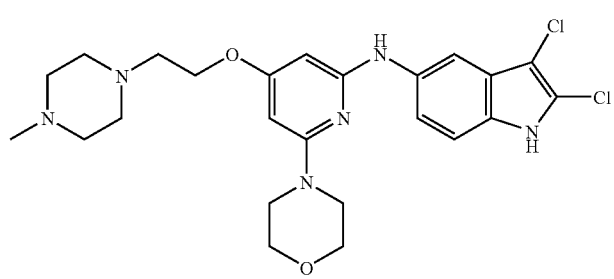

(2,3-Dichloro-1H-indol-5-yl)-{4-[2-(4-methyl-piperazin-1-yl)-ethoxy]-6-morpholin-4-yl-pyridin-2-yl}-amine -continued

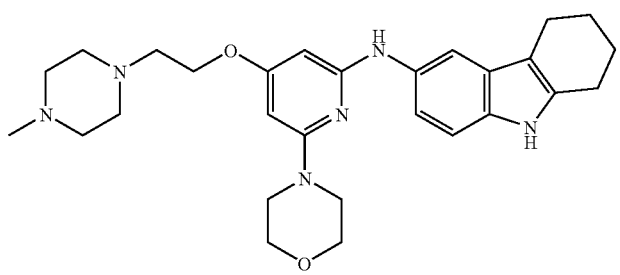

{4-[2-(4-Methyl-piperazin-1-yl)-ethoxy]-6-morpholin-4-yl-pyridin-2-yl}-(6,7,8,9-tetrahydro-5H-carbazol-3-yl)-amine

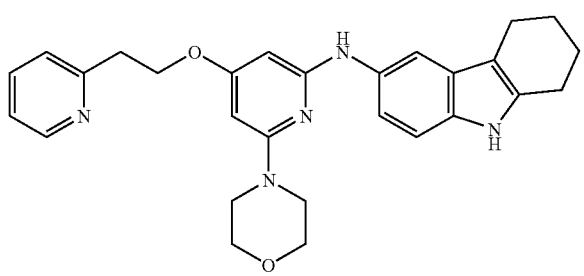

[6-Morpholin-4-yl-4-(2-pyridin-2-yl-ethoxy)-pyridin-2-yl]-(6,7,8,9-tetrahydro-5H-carbazol-3-yl)-amine

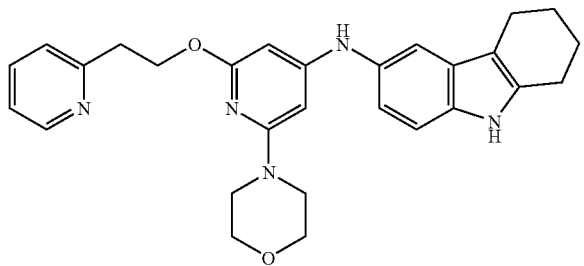

[2-Morpholin-4-yl-6-(2-pyridin-2-yl-ethoxy)-pyridin-4-yl]-(6,7,8,9-tetrahydro-5H-carbazol-3-yl)-amine

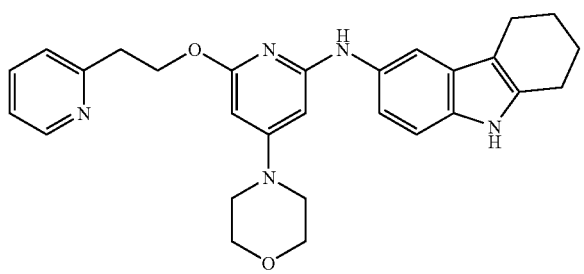

[4-Morpholin-4-yl-6-(2-pyridin-2-yl-ethoxy)-pyridin-2-yl]-(6,7,8,9-tetrahydro-5H-carbazol-3-yl)-amine

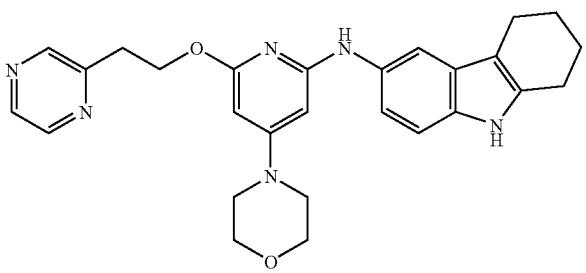

[4-Morpholin-4-yl-6-(2-pyrazin-2-yl-ethoxy)-pyridin-2-yl]-(6,7,8,9-tetrahydro-5H-carbazol-3-yl)-amine Still more compounds of the invention are the following:

N-[3,5-Difluoro-6-morpholin-4-yl-4-(2-morpholin-4-yl-ethoxy)-pyridin-2-yl]-N'-(3-methyl-benzylidene)-hydrazine:

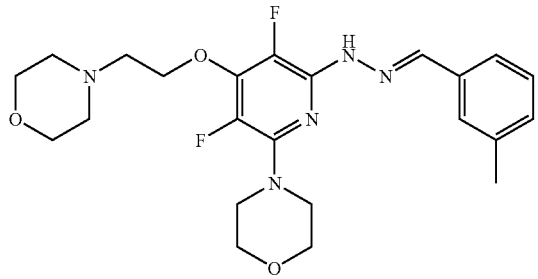

N-[3,5-Difluoro-6-morpholin-4-yl-4-(2-pyridin-2-yl-ethoxy)-pyridin-2-yl]-N'-(3-methyl-benzylidene)-hydrazine:

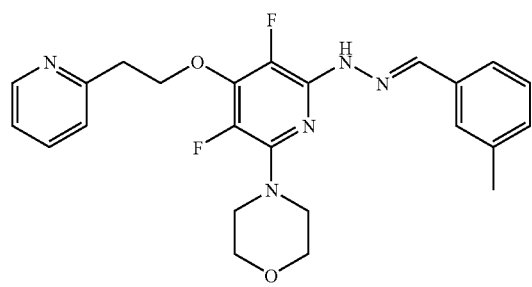

N-[3,5-Difluoro-4-morpholin-4-yl-6-(2-pyridin-2-yl-ethoxy)-pyridin-2-yl]-N'-naphthalen-2-ylmethylene-hydrazine:

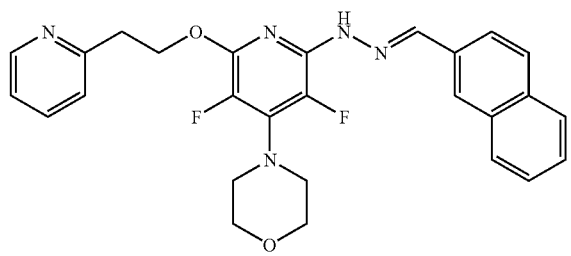

1-[3,5-Difluoro-4-morpholin-4-yl-6-(N'-naphthalen-2-ylmethylene-hydrazino)-pyridin-2-yloxy]-2-methyl-propan-2-ol:

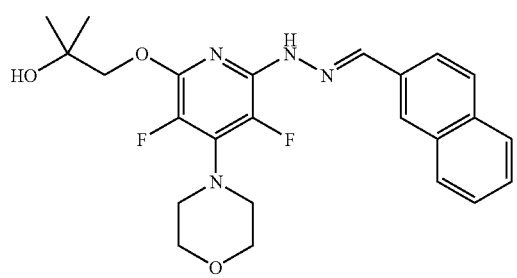

3-{2-[3,5-Difluoro-6-morpholin-4-yl-4-(N'-naphthalen-2-ylmethylene-hydrazino)-pyridin-2-yloxy]-ethyl}-oxazolidin-2-one:

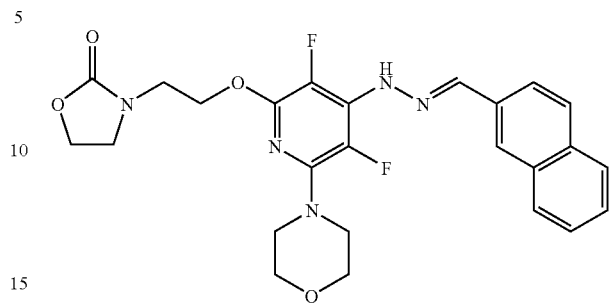

3-(2-{4-[N'-(3,4-Dimethyl-benzylidene)-hydrazino]-3,5-difluoro-6-morpholin-4-yl-pyridin-2-yloxy}-ethyl)-oxazolidin-2-one:

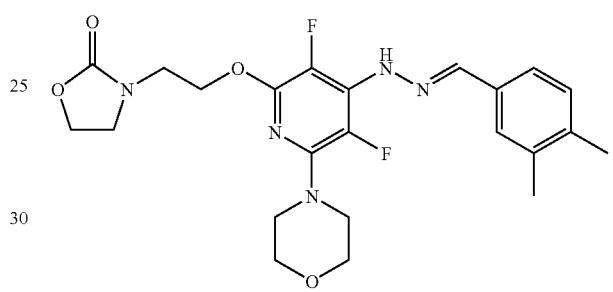

4-{4-[N'-(3,4-Dimethyl-benzylidene)-hydrazine]-3,5-difluoro-6-morpholin-4-yl-pyridin-2-yl}-2-methyl-butan-2-ol:

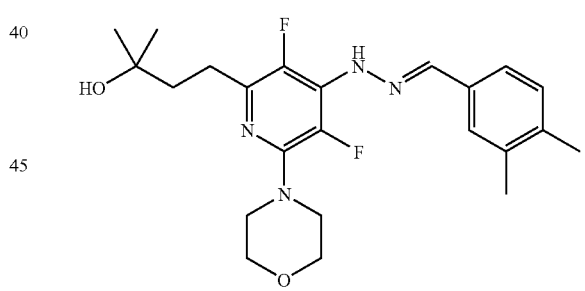

2-{3,5-Difluoro-4-[N'-(1H-indol-3-ylmethylene)-hydrazino]-6-morpholin-4-yl-pyridin-2-yloxy}-ethanol:

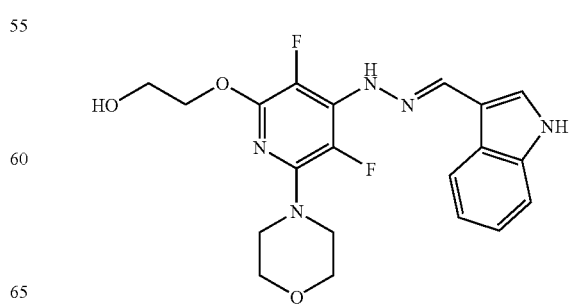

N-[3,5-Difluoro-4-(2-methoxy-ethoxy)-6-morpholin-4-yl-pyridin-2-yl]-N'-(1H-indol-3-ylmethylene)-hydrazine:

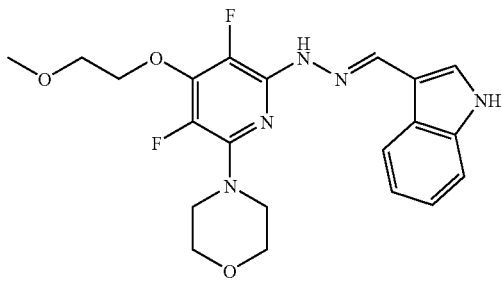

N-{3,5-Difluoro-6-[2-(4-methyl-piperazin-1-yl)-ethoxy]-4-morpholin-4-yl-pyridin-2-yl}-N'-(6-methyl-1H-indol-3-ylmethylene)-hydrazine:

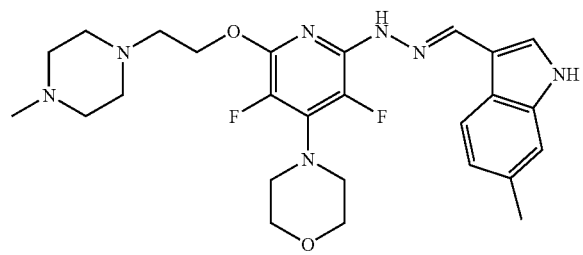

N-(3-Methyl-benzylidene)-N'-[4-morpholin-4-yl-6-(2-morpholin-4-yl-ethoxy)-1-oxy-pyridin-2-yl]-hydrazine:

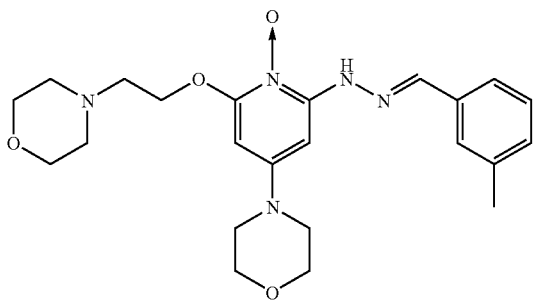

In another aspect, the invention provides a pharmaceutical composition. The pharmaceutical composition includes a pharmaceutically acceptable carrier and a compound of the invention, e.g., any of the formulae or named compounds described herein. Thus, in one embodiment, the pharmaceutical composition comprises a compound of any of the formulae herein or a pharmaceutically acceptable salt, solvate, clathrate, hydrate, polymorph, or prodrug thereof, and a pharmaceutically acceptable carrier.

The compounds of the invention are particularly useful in inhibiting the production of IL-12 and/or inhibiting the production of cytokines such as IL-23 and IL-27 which stimulate and/or otherwise augment the production of IL-12 and/or the proliferation of $T_H1$ lymphocytes. Thus, in one aspect, the present invention provides a method of inhibiting the production of IL-12 and/or inhibiting the production of a cytokine that stimulates or facilitates the production of IL-12 (e.g., IL-23 and IL-27) in a subject by administering to the subject an effective amount of a compound of any of the formulae herein, or a pharmaceutically acceptable salt, solvate, clathrate, hydrate, polymorph, or prodrug thereof.

In another aspect, the invention provides a method of inhibiting IL-23 production in a subject, comprising administering to the subject an effective amount of a compound of the invention, e.g., any of the formulae or named compounds described herein, or pharmaceutically acceptable salt, solvate, clathrate, hydrate, polymorph, or prodrug thereof. In preferred embodiments, the method further comprises inhibiting the production of IL-12.

In another aspect, the invention provides a method of inhibiting IL-27 production in a subject, comprising administering to the subject an effective amount of a compound of the invention, e.g., any of the formulae or named compounds described herein, or pharmaceutically acceptable salt, solvate, clathrate, hydrate, polymorph, or prodrug thereof. In preferred embodiments, the method further comprises inhibiting $T_H1$ lymphocyte proliferation; more preferably, the method still further comprises inhibiting the production of IL-12.

In another aspect, the invention provides method for treating an interleukin-12 production-related disorder, comprising administering to a subject in need thereof an effective amount of a compound of any of the formulae herein, or a pharmaceutically acceptable salt, solvate, clathrate, hydrate, polymorph, or prodrug thereof. In certain embodiments, the disorder is selected from the group consisting of multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease, more preferably rheumatoid arthritis, sepsis, Crohn's disease, multiple sclerosis, psoriasis, or immune-mediated diabetes mellitus. In certain preferred embodiments, in the compound of formula (I), $R_1$ is

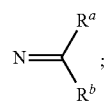

each of $R_2$ and $R_4$ is H; $R_3$ is H, —C(O)OR$^k$, —OC(O)R$^k$, —C(O)NR$^h$R$^j$, —NR$^k$C(O)R$^k$, —C(S)OR$^k$, —OC(S)R$^k$, —NR$^k$C(O)NR$^h$R$^j$, —NR$^k$C(S)NR$^h$R$^j$, —C(O)NR$^h$R$^j$, —S(O)$_2$R$^k$, —S(O)$_2$NR$^h$R$^j$, —OC(O)NR$^h$R$^j$, or —NR$^k$C(O)OR$^k$, a halo, nitro, cyano, an optionally substituted alkyl, an optionally substituted aryl, an optionally substituted heteroaryl, an optionally substituted cyclyl, an optionally substituted heterocyclyl, an optionally substituted alkyloxycarbonyl, an optionally substituted alkylaminocarbonyl, or an optionally substituted alkylcarbonyl; and X is NR$^k$; more preferably, one of R$^a$ and R$^b$ is H or alkyl, and the other is aryl or heteroaryl, wherein the aryl or heteroaryl is optionally substituted with R$^q$ and R$^r_z$, and wherein R$^q$ is halogen, CN, —NH$_2$, alkylamino, dialkylamino, alkyl, alkyloxy, alkylcarbonyl, alkyloxycarbonyl, aryloxycarbonyl, heteroaryloxycarbonyl, hydroxyalkyl, alkylamino, or alkylaminocarbonyl; each $R^r$ is, independently, halogen, CN, —$NH_2$, alkylamino, dialkylamino, hydroxyl, alkyl, aryl, heteroaryl, alkoxyl, aryloxyl, heteroaryloxyl, or —NHC(O)$R^y$, wherein $R^y$ is a lower alkyl; and z is 0, 1, 2, 3, or 4.

In another aspect, the invention provides a method for treating or preventing disorders associated with excessive bone loss, the method comprising administering to a subject in need thereof an effective amount of a compound of any of the formulae herein, or a pharmaceutically acceptable salt, solvate, clathrate, hydrate, polymorph, or prodrug thereof. In preferred embodiments, the disorder is periodontal disease, non-malignant bone disorders, osteoporosis, Paget's disease of bone, osteogenesis imperfecta, fibrous dysplasia, and primary hyperparathyroidism, estrogen deficiency, inflammatory bone loss, bone malignancy, arthritis, osteopetrosis, hypercalcemia of malignancy (HCM), osteolytic bone lesions of multiple myeloma and osteolytic bone metastases of breast cancer, and metastatic cancers.

In another aspect, the invention provides a method for inhibiting osteoclast formation in vitro or in vivo, the method comprising contacting a pre-osteoclast cell with an effective amount of a compound of any of the formulae herein, or a pharmaceutically acceptable salt, solvate, clathrate, hydrate, polymorph, or prodrug thereof.

In another aspect, the invention provides a method of treating or preventing a disorder associated with excessive bone resorption by osteoclasts in a subject in need thereof, the method comprising administering to the subject an effective amount of a compound of any of the formulae herein, or a pharmaceutically acceptable salt, solvate, clathrate, hydrate, polymorph, or prodrug thereof.

Since the function of IL-12 is induction of INF-γ expression from T and NK cells which promotes the development of $T_H1$ T lymphocyte type, the compounds of the invention can be used to inhibit the production of $T_H1$ cells. Therefore, in another aspect, the invention features a method of inhibiting the production and/or development of $T_H1$ cells in a subject by administering to the subject an effective amount of a compound of any of the formulae herein, or a pharmaceutically acceptable salt, solvate, clathrate, hydrate, polymorph, or prodrug thereof.

In still another embodiment, the invention provides a method of inhibiting the proliferation of $T_H1$ lymphocytes in a subject, comprising administering to the subject an effective amount of a compound of the invention, e.g., a compound of formula (I) or any compound named herein.

In another aspect, the invention provides a method of treating an IL-12 overproduction-related disorder, comprising administering to a subject in need thereof a therapeutically effective amount of a compound of any of the formulae herein or a pharmaceutically acceptable salt, solvate, clathrate, hydrate, polymorph, or prodrug thereof. IL-12 overproduction disorders include, but are not limited to multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease.

In another aspect, the invention provides a method of inhibiting the production of IL-12 and/or inhibiting the production of a cytokine that stimulates or facilitates the production of IL-12 (e.g., IL-23 and IL-27) in a subject. The method includes administering to the subject a compound of any of the formulae herein or a pharmaceutically acceptable salt, solvate, clathrate, hydrate, polymorph, or prodrug thereof.

Although the mechanism is not yet understood, compounds of the invention have been found to inhibit the formation of osteoclasts (see co-owned PCT Application Number US04/17064 filed on May 28, 2004, the entire teachings of which are incorporated herein by reference). Osteoclasts are unique multinucleated cells within bone that are responsible for bone degradation and resorption. These are the only cells in the body known to be capable of this function. The regulation of osteoclastic formation and activity is only partly understood but it is known that excessive bone resorption by osteoclasts contributes to the pathology of many human diseases associated with excessive bone loss. Thus, in one aspect, the invention provides a method of treating or preventing disorders associated with excessive bone loss, comprising administering to a subject in need thereof a therapeutically effective amount of a compound of any of the formulae herein or pharmaceutically acceptable salt, solvate, clathrate, hydrate, polymorph, or prodrug thereof. Disorders associated with excessive bone loss include, but are not limited to periodontal disease, non-malignant bone disorders, osteoporosis, Paget's disease of bone, osteogenesis imperfecta, fibrous dysplasia, and primary hyperparathyroidism, estrogen deficiency, inflammatory bone loss, bone malignancy, arthritis, osteopetrosis, hypercalcemia of malignancy (HCM), osteolytic bone lesions of multiple myeloma and osteolytic bone metastases of breast cancer, and metastatic cancers.

In another aspect, the invention provides a method for inhibiting osteoclast formation in vitro or in vivo, comprising contacting a pre-osteoclast cell with an effective amount of a compound of any of the formulae herein or pharmaceutically acceptable salt, solvate, clathrate, hydrate, polymorph, or prodrug thereof.

In another aspect, the invention provides a method of treating or preventing a disorder associated with excessive bone resorption by osteoclasts in a subject in need thereof, comprising administering to the subject an effective amount of a compound of any of the formulae herein or pharmaceutically acceptable salt, solvate, clathrate, hydrate, polymorph, or prodrug thereof. The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

In another aspect, the invention provides a method of treating or preventing an inflammatory disorder in a subject in need thereof, the method comprising administering to the subject an effective amount of a compound of the invention, e.g., any of the formulae or named compounds described herein, or pharmaceutically acceptable salt, solvate, clathrate, hydrate, polymorph, or prodrug thereof. In certain embodiments, the inflammatory disorder is asthma, adult respiratory distress syndrome, systemic lupus erythematosus, inflammatory bowel disease (including Crohn's disease and ulcerative colitis), multiple sclerosis, insulin-dependent diabetes mellitus, autoimmune arthritis (including rheumatoid arthritis, juvenile rheumatoid arthritis, psoriatic arthritis), inflammatory pulmonary syndrome, pemphigus vulgaris, idiopathic thrombocytopenic purpura, autoimmune meningitis, myasthenia gravis, autoimmune thyroiditis, dermatitis (including atopic dermatitis and eczematous dermatitis), psoriasis, Sjogren's Syndrome (including keratoconjunctivitis sicca secondary to Sjogren's Syndrome), alopecia greata, allergic responses due to arthropod bite reactions, aphthous ulcer, iritis, conjunctivitis, keratoconjunctivitis, cutaneous lupus erythematosus, scleroderma, vaginitis, proctitis, drug eruptions (such as Stevens-Johnson syndrome), leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves opthalmopathy, primary biliary cirrhosis, uveitis posterior, or interstitial lung fibrosis. In another aspect, the invention provides a method of treating or preventing an immune disease in a subject in need thereof, the method comprising administering to the subject an effective amount of a compound of the invention, e.g., any of the formulae or named compounds described herein, or pharmaceutically acceptable salt, solvate, clathrate, hydrate, polymorph, or prodrug thereof. In certain embodiments, the immune disease is rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), or chronic salicylate intoxication.

In another aspect, the invention provides a method of treating or preventing a neurological disorder in a subject in need thereof, the method comprising administering to the subject an effective amount of a compound of the invention, e.g., any of the formulae or named compounds described herein, or pharmaceutically acceptable salt, solvate, clathrate, hydrate, polymorph, or prodrug thereof. In certain embodiments, the neurological disorder is a neurodegenerative disease, multiple sclerosis, migraine headache, AIDS dementia complex, demyelinating disease, such as multiple sclerosis and acute transverse myelitis; extrapyramidal and cerebellar disorders such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; or Dementia pugilistica.

Other embodiments include the compounds, intermediates, or a pharmaceutically acceptable salt, solvate, clatharate, hydrate, polymorph, or prodrug thereof delineated herein, or compositions including them; as well as their methods of use for treatment or prevention of disease, inhibition of IL-12, or modulation of IL-12 mediated disease.

Another embodiment is a method of making a compound of any of the formulae herein using any one, or combination of, reactions delineated herein. The method can include the use of one or more intermediates or chemical reagents delineated herein.

Another aspect is a radiolabeled compound of any of the formulae delineated herein. Such compounds have one or more radioactive atoms (e.g., $^3$H, $^2$H, $^{14}$C, $^{13}$C, $^{32}$P, $^{35}$S, $^{125}$I, $^{131}$I) introduced into the compound. Such compounds are useful for drug metabolism studies and diagnostics.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The sp$^2$ or sp carbons of an alkenyl group and an alkynyl group, respectively, may optionally be the point of attachment of the alkenyl or alkynyl groups.

The term "alkoxy" refers to an —O-alkyl radical. The term "ester" refers to a —C(O)O—R$^k$; or, where a divalent group is indicated, an "ester" group is —C(O)O— or —OC(O)—. An "amido" is an —C(O)NH$_2$, and an "N-alkyl-substituted amido" is of the formula C(O)NHR$^k$; where a divalent "amide" group is indicated, the group is —C(O)N$^k$— or —N$^k$C(O)—.

The term "mercapto" refers to a —SH group.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

The term "cycloalkyl" refers to a hydrocarbon 3-8 membered monocyclic or 7-14 membered bicyclic ring system having at least one non-aromatic, completely saturated ring. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cyclyl" refers to a hydrocarbon 3-8 membered monocyclic or 7-14 membered bicyclic ring system having at least one non-aromatic ring, wherein the non-aromatic ring has some degree of unsaturation. Cyclyl groups may be optionally substituted with one or more substituents. In one embodiment, 0, 1, 2, 3, or 4 atoms of each ring of a cyclyl group may be substituted by a substituent. Examples of cyclyl groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "aralkyl" means an aryl group that is attached to another group by a $(C_1$-$C_6)$alkylene group. Aralkyl groups may be optionally substituted, either on the aryl portion of the aralkyl group or on the alkylene portion of the aralkyl group, with one or more substituent. Representative aralkyl groups include benzyl, 2-phenyl-ethyl, naphth-3-yl-methyl and the like.

As used herein, the term "alkylene" refers to an alkyl group that has two points of attachment. The term "$(C_1$-$C_6)$alkylene" refers to an alkylene group that has from one to six carbon atoms. Non-limiting examples of alkylene groups include methylene (—CH$_2$—), ethylene (—CH$_2$CH$_2$—), n-propylene (—CH$_2$CH$_2$CH$_2$—), isopropylene (—CH$_2$CH(CH$_3$)—), and the like.

The term "arylalkoxy" refers to an alkoxy substituted with aryl.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo[b]thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a $(C_1$-$C_6)$alkylene. Heteroaralkyl groups may be optionally substituted, either on the heteroaryl portion of the heteroaralkyl group or on the alkylene portion of the heteroaralkyl group, with one or more substituent. Representative heteroaralkyl groups include 2-(pyridin-4-yl)-propyl, 2-(thien-3-yl)-ethyl, imidazol-4-yl-methyl and the like.

The term "heterocycloalkyl" refers to a nonaromatic, completely saturated 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl, thiirene.

The term "heterocyclyl" refers to a nonaromatic 5-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclyl groups may be optionally substituted with one or more substituents. In one embodiment, 0, 1, 2, 3, or 4 atoms of each ring of a heterocyclyl group may be substituted by a substituent. Examples of these groups include thiirenyl, thiadiazirinyl, dioxazolyl, 1,3-oxathiolyl, 1,3-dioxolyl, 1,3-dithiolyl, oxathiazinyl, dioxazinyl, dithiazinyl, oxadiazinyl, thiadiazinyl, oxazinyl, thiazinyl, 1,4-oxathiin, 1,4-dioxin, 1,4-dithiin, 1H-pyranyl, oxathiepinyl, 5H-1,4-dioxepinyl, 5H-1,4-dithiepinyl, 6H-isoxazolo[2,3-d]1,2,4-oxadiazolyl, 7aH-oxazolo[3,2-d]1,2,4-oxadiazolyl, and the like.

The term "alkylamino" refers to an amino substituent which is further substituted with one or two alkyl groups. The term "aminoalkyl" refers to an alkyl substituent which is further substituted with one or more amino groups. The term "mercaptoalkyl" refers to an alkyl substituent which is further substituted with one or more mercapto groups. The term "hydroxyalkyl" or "hydroxylalkyl" refers to an alkyl substituent which is further substituted with one or more hydroxyl groups. The term "sulfonylalkyl" refers to an alkyl substituent which is further substituted with one or more sulfonyl groups. The term "sulfonylaryl" refers to an aryl substituent which is further substituted with one or more sulfonyl groups. The term alkylcarbonyl refers to an —C(O)-alkyl. The term "mercaptoalkoxy" refers to an alkoxy substituent which is further substituted with one or more mercapto groups. The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, cyclyl, heterocycloalkyl, or heterocyclyl group) is replaced with any desired group that do not substantially adversely affect the stability of the compound. In one embodiment, desired substituents are those which do not adversely affect the activity of a compound. A substituent that substantially affects the activity of a compound is one that causes the $IC_{50}$ of the compound to be greater than 100 µM. In preferred embodiments, a compound of the invention has an $IC_{50}$ in an assay or test indicative of activity useful for treatment of IL-12- or IL-23- or IL-27-related diseases or conditions. Such assays are known to one of ordinary skill in the art, and include, e.g., the assays described herein, e.g., the assays of Examples 22-25. In preferred embodiments, the assay is an assay of Example 22 and the compound has an $IC_{50}$ less than 1.0 mM, more preferably less than 100 µM, more preferably less than 10 µM, more preferably less than 1 µM, more preferably less than 100 nM, and more preferably less than 10 nM. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), or imino (=NR$^c$).

In other embodiments, substituents on any group (such as, for example, alkyl, alkenyl, alkynyl, aryl, aralkyl, heteroaryl, heteroaralkyl, cycloalkyl, cyclyl, heterocycloalkyl, and heterocyclyl) can be at any atom of that group, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocyclyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents an alkyl, alkenyl, alkynyl, aryl, aralkyl, heteroaryl, heteroaralkyl, cycloalkyl, cyclyl, heterocycloalkyl, and heterocyclyl include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, (=O), (=S), (=$NR^{15}$), $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)H$, $C(O)R^{17}$, $NR^{15}C(O)R^{17}$, $Si(R^{15})_3$, $OSi(R^{15})_3$, $Si(OH)_2R^{15}$, $B(OH)_2$, $P(O)(OR^{15})_2$, $S(O)R^{17}$, or $S(O)_2R^{17}$. Each $R^{15}$ is independently hydrogen, $C_1$-$C_6$ alkyl optionally substituted with cycloalkyl, aryl, heterocyclyl, or heteroaryl. Each $R^{16}$ is independently hydrogen, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, COOH, $C(O)OC_1$-$C_4$ alkyl, $NH_2$, $C_1$-$C_4$ alkylamino, or $C_1$-$C_4$ dialkylamino.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

Note that unless otherwise depicted, in the groups described above that have one point of attachment, the left atom shown in any substituted group is the point of attachment.

In the compounds represented by formula (I), when n is 2 or greater, a compound of the invention may have two or more different $C(R^2R^4)$ moieties. When there are more than one group having a designation (e.g., $R^c$-, or $R^d$-containing substituted groups) in a compound of the invention, the moieties (e.g., $R^c$, $R^d$) can be the same or different. The same rules apply to other R-groups (e.g., R, $R^a$, $R^b$, $R^f$, $R^g$, $R^h$, $R^j$, $R^k$, etc).

The recitation of a listing of chemical groups in any definition of a variable herein includes definitions of that variable as any single group or combination of listed groups.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating IL-12 overproduction-related disorders such as rheumatoid arthritis, sepsis, Crohn's disease, multiple sclerosis, psoriasis, or insulin-dependent diabetes mellitus). The compounds produced by the methods herein can be incorporated into compositions, including solutions, capsules, crémes, or ointments for administration to a subject (e.g., human, animal). Such compositions (e.g., pharmaceuticals) are useful for providing to the subject desirable health or other physiological benefits that are associated with such compounds.

The compounds of this invention include the compounds themselves, as well as their salts, solvate, clathrate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, which further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

In addition, some of the heterocyclic compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Further, the aforementioned heterocyclic compounds also include their N-oxides. The term "N-oxides" refers to one or more nitrogen atoms, when present in a heterocyclic or heteroaryl compound, are in N-oxide form, i.e., N→O. For example, in compounds of formula (I), when one of Q, U, or V is N, also included are compounds in which Q, U, or V, respectively, is N→O.

The term "inflammatory disorders" includes any inflammatory disease, disorder or condition caused, exasperated or mediated by IL-12 production. Such inflammatory disorders may include, without limitation, asthma, adult respiratory distress syndrome, systemic lupus erythematosus, inflammatory bowel disease (including Crohn's disease and ulcerative colitis), multiple sclerosis, insulin-dependent diabetes mellitus, autoimmune arthritis (including rheumatoid arthritis, juvenile rheumatoid arthritis, psoriatic arthritis), inflammatory pulmonary syndrome, pemphigus vulgaris, idiopathic thrombocytopenic purpura, autoimmune meningitis, myasthenia gravis, autoimmune thyroiditis, dermatitis (including atopic dermatitis and eczematous dermatitis), psoriasis, Sjogren's Syndrome (including keratoconjunctivitis sicca secondary to Sjogren's Syndrome), alopecia greata, allergic responses due to arthropod bite reactions, aphthous ulcer, iritis, conjunctivitis, keratoconjunctivitis, cutaneous lupus erythematosus, scleroderma, vaginitis, proctitis, drug eruptions (such as Stevens-Johnson syndrome), leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves opthalmopathy, primary biliary cirrhosis, uveitis posterior and interstitial lung fibrosis.

"Inflammatory disorders" expressly include acute inflammatory disorders. Examples of acute inflammatory disorders include graft versus host disease, transplant rejection, septic shock, endotoxemia, Lyme arthritis, infectious meningitis (e.g., viral, bacterial, Lyme disease-associated), an acute episode of asthma and acute episodes of an autoimmune disease.

"Inflammatory disorders" expressly include chronic inflammatory disorders. Nonlimiting examples of chronic inflammatory disorder include asthma, rubella arthritis, and chronic autoimmune diseases, such as systemic lupus erythematosus, psoriasis, inflammatory bowel disease, including Crohn's disease and ulcerative colitis, multiple sclerosis and rheumatoid arthritis.

The term "immune diseases" includes any immune disease, disorder or condition caused, exasperated or mediated by IL-12 production. Such immune diseases may include, without limitation, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The term "bone loss disease" includes any bone loss disease, disorder or condition caused, exasperated or mediated by IL-12 production e.g., periodontal disease, non-malignant bone disorders (e.g., osteoporosis, Paget's disease of bone, osteogenesis imperfecta, fibrous dysplasia, and primary hyperparathyroidism), estrogen deficiency, inflammatory bone loss, bone malignancy, arthritis, osteopetrosis, and certain cancer-related disorders (e.g., hypercalcemia of malignancy (HCM), osteolytic bone lesions of multiple myeloma and osteolytic bone metastases of breast cancer and other metastatic cancers.

The term "neurological disorder" includes any neurological disease, disorder or condition caused, exasperated or mediated by IL-12 production. Such neurological disorders may include, without limitation, neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16, Edition, Merck & Company, Rahway, N.J. (1992)

In the case of overlap in these definitions, the disease, condition or disorder may be considered to be a member of any of the above listed classes of IL-12 production-related disorders.

In still another aspect, the present invention features a method for treating an IL-12 production-related disorder (e.g., rheumatoid arthritis, sepsis, Crohn's disease, multiple sclerosis, psoriasis, or insulin-dependent diabetes mellitus). The method includes administering to a subject (e.g., a human or an animal) in need thereof an effective amount of one or more compounds of formula (I) or a pharmaceutically acceptable salt, solvate, clathrate, hydrate, polymorph or prodrug thereof, or a pharmaceutical composition having an effective amount of one or more compounds of formula (I) or a pharmaceutically acceptable salt, solvate, clathrate, hydrate, polymorph or prodrug thereof. The method can also include the step of identifying that the subject is in need of treatment of diseases or disorders described above. The identification can be in the judgment of a subject or a health professional and can be subjective (e.g., opinion) or objective (e.g., measurable by a test or a diagnostic method).

In one aspect, this invention features a method for treating or preventing disorders associated with excessive bone loss, e.g., periodontal disease, non-malignant bone disorders (e.g., osteoporosis, Paget's disease of bone, osteogenesis imperfecta, fibrous dysplasia, and primary hyperparathyroidism), estrogen deficiency, inflammatory bone loss, bone malignancy, arthritis, osteopetrosis, and certain cancer-related disorders (e.g., hypercalcemia of malignancy (HCM), osteolytic bone lesions of multiple myeloma and osteolytic bone metastases of breast cancer and other metastatic cancers). The method includes administering to a subject (e.g., a human or an animal) in need thereof an effective amount of one or more compounds of formula (I) or a pharmaceutically acceptable salt, solvate, clathrate, or prodrug thereof, or a pharmaceutical composition having an effective amount of one or more compounds of formula (I) or a pharmaceutically acceptable salt, solvate, clathrate, or prodrug thereof. The method can also include the step of identifying that the subject is in need of treatment of diseases or disorders described above. The identification can be in the judgment of a subject or a health professional and can be subjective (e.g., opinion) or objective (e.g., measurable by a test or a diagnostic method).

In another aspect, this invention features methods for inhibiting osteoclast formation in vitro or in vivo. The method includes contacting a pre-osteoclast cell (e.g., a cell capable of forming an osteoclast cell upon differentiation and/or fusion) with an effective amount of a compound of formula (I) or a pharmaceutically acceptable salt, solvate, clathrate, or prodrug thereof or a pharmaceutical composition comprising an effective amount of a compound of formula (I) or a pharmaceutically acceptable salt, solvate, clathrate, hydrate, polymorph or prodrug thereof.

In a further aspect, this invention features methods of treating or preventing a disorder associated with excessive bone resorption by osteoclasts in a subject in need thereof. The method includes administering to a subject (e.g., a human or an animal) in need thereof an effective amount of one or more compounds of formula (I) or a pharmaceutically acceptable salt, solvate, clathrate, or prodrug thereof, or a pharmaceutical composition having an effective amount of one or more compounds of formula (I) or a pharmaceutically acceptable salt, solvate, clathrate, hydrate, polymorph or prodrug thereof. The method can also include the step of identifying that the subject is in need of treatment of diseases or disorders described above. The identification can be in the judgment of a subject or a health professional and can be subjective (e.g., opinion) or objective (e.g., measurable by a test or a diagnostic method).

Also within the scope of this invention are a composition containing one or more of the pyridine compounds described above for use in treating an IL-12 production-related disorder (e.g., rheumatoid arthritis, sepsis, Crohn's disease, multiple sclerosis, psoriasis, or insulin-dependent diabetes mellitus), treating or preventing disorders associated with excessive bone loss, e.g., periodontal disease, non-malignant bone disorders (e.g., osteoporosis, Paget's disease of bone, osteogenesis imperfecta, fibrous dysplasia, and primary hyperparathyroidism) estrogen deficiency, inflammatory bone loss, bone malignancy, arthritis, osteopetrosis, and certain cancer-related disorders (e.g., hypercalcemia of malignancy (HCM), osteolytic bone lesions of multiple myeloma and osteolytic bone metastases of breast cancer and other metastatic cancers), inhibiting osteoclast formation in vitro or in vivo, or treating or preventing a disorder associated with excessive bone resorption by osteoclasts) and the use of such a composition for the manufacture of a medicament for the just-described use.

The compounds described above can be prepared by methods described herein, some of which are known in the art. For example, a pyridine compound can be prepared by using 2,4,6-trichloro-pyridine as a starting material. The three chloro groups can be displaced by various substitutents. More specifically, a first chloro group (e.g., at position 2 or position 4) can react with, e.g., morpholine, to form a morpholinyl pyridine, e.g., compounds A and B in Scheme 1 below. The desired isomeric product can be separated from others by, e.g., high performance liquid chromatography or flash chromatography. A second chloro group can be replaced by reacting with a nucleophile, such as an alcohol in the presence of base, e.g., sodium hydride, to provide, e.g., compounds C and D in Scheme 1 below. In other examples, a compound of formula (I), wherein Y is CH$_2$ (e.g., Compound 1), can be prepared by reacting the pyridine chloride with a Grignard reagent, an organotin reagent, an organocopper reagent, an organoboric acid, or an organozinc reagent in the presence of an organopalladium compound as a catalyst. Isomeric forms may be produced. The desired isomeric product can be separated from others by, e.g., high performance liquid chromatography. A third chloro group undergoes a displacement reaction with, e.g., hydrazine, to afford, e.g., compound E in Scheme 1, and the primary amine of the coupled hydrazine moiety further reacts with an aldehyde, e.g., indole-3-carboxaldehyde to form a hydrazone linkage, e.g., compound 1 in Scheme 1. Thus, a pyridine compound of this invention is obtained. If preferred, other types of linkages can be prepared by similar reactions. Sensitive moieties on a pyridinyl intermediate and a nucleophile can be protected prior to coupling. A pyridine compound can also be prepared via a palladium mediated amination of a chloro substituted pyridine starting material. For example, 5-amino-2,3-dimethylindole and 4-{2-chloro-6-[2-(3,4-dimethoxy-phenyl)-pyridin-4-yl]}-morpholine can be coupled in the presence of palladium acetate, binap, and cesium carbonate in refluxing toluene to provide compound 4.

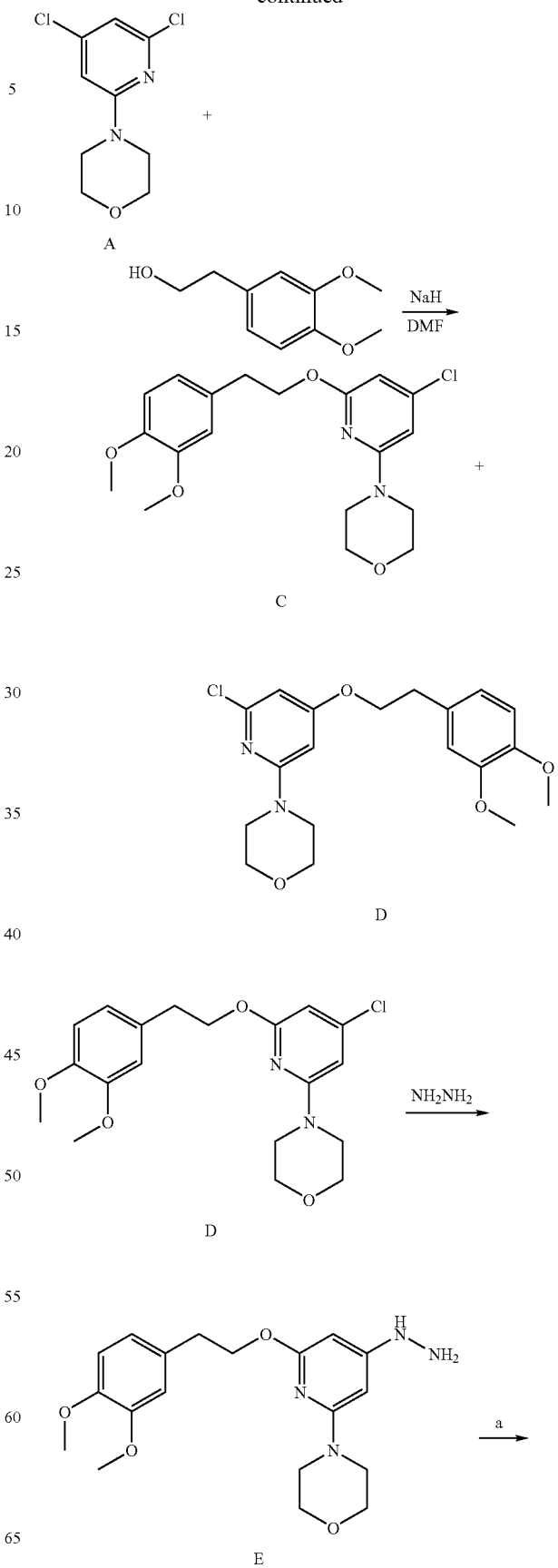

-continued

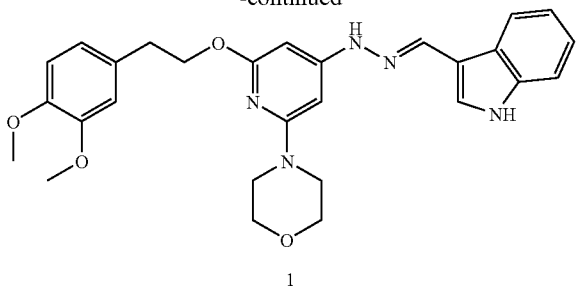

1

(a) = 3-indolecarboxaldehyde

The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the pyridine compounds. In addition, various synthetic steps may be performed in an alternate sequence or order to give the desired compounds. Synthetic chemistry transformations and protecting group methodologies (protection and deprotection) useful in synthesizing applicable pyridine compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A pyridine compound thus obtained can be further purified by flash column chromatography, high performance liquid chromatography, or crystallization.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)$CF_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally include steps, either before or after the steps described specifically herein, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography). Other embodiments relate to the intermediate compounds delineated herein, and their use in the methods (e.g., treatment, synthesis) delineated herein.

The compounds and compositions described herein are useful to treat and prevent any IL-12 production-related disorders, e.g., inflammatory disorders, immune diseases, and bone loss diseases. The method involves administering an effective amount of a compound of the invention, or a pharmaceutically acceptable salt, solvate, clathrate, hydrate, polymorph, or prodrug thereof, to a subject in need of treatment of IL-12 overproduction related diseases As used herein, the term "effective amount" refers to an amount of a compound of this invention which is sufficient to reduce or ameliorate the severity, duration, progression, or onset of an inflammatory disorder, immune diseases, or bone loss disease, prevent the advancement of an inflammatory disorder, immune diseases, or bone loss disease, cause the regression of an inflammatory disorder, immune diseases, or bone loss disease, prevent the recurrence, development, onset or progression of a symptom associated with an inflammatory disorder, immune diseases, or bone loss disease, or enhance or improve the prophylactic or therapeutic effect(s) of another therapy. In certain preferred embodiments, treatment according to the invention provides a reduction in or prevention of at least one symptom or manifestation of an IL-12-, IL-23-, or IL-27-related disorder (e.g., inflammatory disorder, immune diseases, or bone loss disease), as determined in vivo or in vitro of at least about 10%, more preferably 20%, 30%, 40%, 50%, 60%, 70%, 80%, 90%, 95%, 98% or 99%.

The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the pyridine compound of this invention can range from about 0.001 mg/kg to about 1000 mg/kg, more preferably 0.01 mg/kg to about 100 mg/kg, more preferably 0.1 mg/kg to about 10 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents.

To practice the method of the present invention, a compound disclosed herein, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A heterocyclic compound of this invention can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the compounds of this invention, or one or more solubilizing agents, can be utilized as pharmaceutical excipients for delivery of the heterocyclic compounds. Examples of other carriers include colloidal silicon dioxide, magnesium stearate, cellulose, sodium lauryl sulfate, and D&C Yellow # 10.

In certain embodiments, pharmaceutical compositions and dosage forms of the invention comprise one or more active ingredients in relative amounts and formulated in such a way that a given pharmaceutical composition or dosage form inhibits the uptake of calcium. Preferred pharmaceutical compositions and dosage forms comprise a compound of formula (I), or a pharmaceutically acceptable prodrug, salt, solvate, or clathrate thereof, optionally in combination with one or more additional active agents.

The methods for treating or preventing disorders associated with excessive bone loss in a patient in need thereof can further comprise administering to the patient being administered a compound of this invention, an effective amount of one or more other therapeutic agents. Such therapeutic agents may include other therapeutic agents such as those conventionally used to prevent or treat disorders associated with excessive bone resorption or symptoms thereof. For example, such other agents include anti-resorptive agents for example progestins, polyphosphonates, bisphosphonate(s), estrogen agonists/antagonists, estrogen (such as Premarin®), estrogen/progestin combinations, and estrogen derivatives (such as estrone, estriol or 17α, 17β-ethynyl estradiol).

In such combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the compound of this invention is less than its effective amount would be where the other therapeutic agent is not administered. In another embodiment, the effective amount of the conventional agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, dthynodiol diacetate, etonogestrel, fluorogestone acetate, gestaclone, gestodene, gestonorone caproate, gestrinone, haloprogesterone, hydroxyprogesterone, caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol. Preferred progestins are medroxyprogestrone, norethindrone and norethynodrel.

Exemplary bone resorption inhibiting polyphosphonates include polyphosphonates of the type disclosed in U.S. Pat. No. 3,683,080. Preferred polyphosphonates are geminal dipolyphosphonates (also referred to as bis-phosphonates). Tiludronate disodium is an especially preferred polyphosphonate. Ibandronic acid is an especially preferred polyphosphonate. Alendronate is an especially preferred polyphosphonate. Zoledronic acid is an especially preferred polyphosphonate. Other preferred polyphosphonates are 6-amino-1-hydroxy-hexylidene-biphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl)amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used for this purpose. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue; and blocking the actions of estrogen in one or more tissues. Such activities are readily determined by those skilled in the art of standard assays including estrogen receptor binding assays, standard bone histomorphometric and densitometer methods, and E. F Eriksen et al., Bone Histomorphometry, Raven Press, New York, pp. 1-74 (1994); S. J. Grier et. al., The Use of Dual-Energy X-Ray Absorptiometry In Animals, Inv. Radiol. 31(1): 50-62 (1996); Wahner H. W. and Fogelman I., The Evaluation of Osteoporosis: Dual Energy X-Ray Absorptiometry in Clinical Practice., Martin Dunitz Ltd., London, pp. 1-296 (1994)). A variety of these compounds are described and referenced below.

A preferred estrogen agonist/antagonist is droloxifene: (phenol, 3-(1-(4-(2-(dimethylamino)ethoxy)phenyl)-2-phenyl-1-butenyl)-, (E)-) and related compounds which are disclosed in U.S. Pat. No. 5,047,431. Another preferred estrogen agonist/antagonist is 3-(4-(1,2-diphenyl-but-1-enyl)-phenyl)-acrylic acid, which is disclosed in Wilson et al., Endocrinology 138: 3901-11 (1997). Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516. Another related compound is 4-hydroxy tamoxifen which is disclosed in U.S. Pat. No. 4,623,660.

A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)hydrochloride) which is disclosed in U.S. Pat. No. 4,418,068. Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225. Another preferred estrogen agonist/antagonist is centchroman: 1-(2-((4-(-methoxy-2,2,dimethyl-3-phenyl-chroman-4-yl)-phenoxy)-ethyl)-pyrrolidine, which is disclosed in U.S. Pat. No. 3,822,287. Also preferred is levormeloxifene. Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155. Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058. Another preferred estrogen agonist/antagonist is 6-(4-hydroxy-phenyl)-5-(4-(2-piperidin-1-yl-ethoxy)-benzyl)-naphthalen-2-ol which is disclosed in U.S. Pat. No. 5,484,795. Another preferred estrogen agonist/antagonist is (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone which is disclosed, along with methods of preparation, in PCT publication no. WO 95/10513 assigned to Pfizer Inc. Other preferred estrogen agonist/antagonists include compounds as described in U.S. Pat. No. 5,552,412. Especially preferred compounds described therein are: cis-6-(4-fluoro-phenyl)-5-(4-(2-piperidin-1-yl-ethoxy)-phenyl)-5,6,7,8-tetr ahydro-naphthalene-2-ol; (−)-cis-6-phenyl-5-(4-(2-pyrrolidin-1-yl-ethoxy)-phenyl)-5,6,7,8-tetrahydro-naphthalene-2-ol; cis-6-phenyl-5-(4-(2-pyrrolidin-1-yl-ethoxy)-phenyl)-5,6,7,8-tetrahydro-naphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-(4-(2-piperidin-1-yl-ethoxy)-phenyl)-5,6,7,8-tetrahydro-naphthalene-2-ol; and 1-(4'-pyrrolidinolethoxyphenyl)-2-phenyl-6-hydroxy-1,2,3,4-tetrahydroisoquinoline. Other estrogen agonist/antagonists are described in U.S. Pat. No. 4,133,814. U.S. Pat. No. 4,133,814 discloses derivatives of 2-phenyl-3-aroyl-benzothiophene and 2-phenyl-3-aroylbenzothiophene-1-oxide.

Those skilled in the art will recognize that other bone anabolic agents, also referred to as bone mass augmenting agents, may be used in conjunction with the compounds of this invention. A bone mass augmenting agent is a compound that augments bone mass to a level which is above the bone fracture threshold as detailed in the World Health Organization Study World Health Organization, "Assessment of Fracture Risk and its Application to Screening for Postmenopausal Osteoporosis (1994). Report of a WHO Study Group. World Health Organization Technical Series 843." Any prostaglandin, or prostaglandin agonist/antagonist may be used in combination with the compounds of this invention. Those skilled in the art will recognize that IGF-1, sodium fluoride, parathyroid hormone (PTH), active fragments of parathyroid hormone, growth hormone or growth hormone secretagogues may also be used. The following paragraphs describes in greater detail exemplary compounds that may be administered in combination with compounds of this invention Prostaglandins: The term prostaglandin refers to compounds which are analogs of the natural prostaglandins $PGD_1$, $PGD_2$, $PGE_2$, $PGE_1$ and $PGF_2$ which are useful in the treatment of osteoporosis and other disorders associated with excessive osteoclastic bone resorption. These compounds bind to the prostaglandins receptors. Such binding is readily determined by those skilled in the art of standard assays (e.g., S. An et al., Cloning and Expression of the $EP_2$ Subtype of Human Receptors for Prostaglandin $E_2$ Biochemical and Biophysical Research Communications, 197(1): 263-270 (1993)).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while $PGE_2$ contains a trans unsaturated double bond at the $C_{13}$-$C_{14}$ and a cis double bond at the $C_5$-$C_6$ position.

A variety of prostaglandins are described and referenced below. However, other prostaglandins will be known to those skilled in the art. Exemplary prostaglandins are disclosed in U.S. Pat. Nos. 4,171,331 and 3,927,197, Norrdin et al., The Role of Prostaglandins in Bone in Vivo, Prostaglandins Leukotriene Essential Fatty Acids 41: 139-150 (1990) is a review of bone anabolic prostaglandins. Any prostaglandin agonist/antagonist may be used in combination with the compounds of this invention. The term prostaglandin agonist/antagonist refers to compounds which bind to prostaglandin receptors (eg., An S. et al., Cloning and Expression of the $EP_2$ Subtype of Human Receptors for Prostaglandin $E_2$, Biochemical and Biophysical Research Communications 197(1): 263-70 (1993)) and mimic the action of prostaglandin in vivo (e.g., stimulate bone formation and increase bone mass). Such actions are readily determined by those skilled in the art of standard assays. Eriksen E. F. et al., Bone Histomorphometry, Raven Press, New York, 1994, pp. 1-74; S. J. Grier et al., The Use of Dual-Energy X-Ray Absorptiometry In Animals, Inv. Radiol. 31(1): 50-62 (1996); H. W. Wahner and I. Fogelman, The Evaluation of Osteoporosis: Dual Energy X-Ray Absorptiometry in Clinical Practice, Martin Dunitz Ltd. London, pp. 1-296 (1994). A number of these compounds are described and reference below. However, other prostaglandin agonists/antagonists will be known to those skilled in the art. Exemplary prostaglandin agonists/antagonists are disclosed as follows. U.S. Pat. No. 3,932,389 discloses 2-descarboxy-2-(tetrazol-5-yl)-11-desoxy-15-substituted-omega-pentanorprostaglandins useful for bone formation activity. U.S. Pat. No. 4,018,892, discloses 16-aryl-13,14-dihydro-$PGE_2$ p-biphenyl esters useful for bone formation activity. U.S. Pat. No. 4,219,483, discloses 2,3,6-substituted-4-pyrones useful for bone formation activity. U.S. Pat. No. 4,132,847, discloses 2,3,6-substituted-4-pyrones useful for bone formation activity. U.S. Pat. No. 4,000,309, discloses 16-aryl-13,14-dihydro-$PGE_2$ p-biphenyl esters useful for bone formation activity. U.S. Pat. No. 3,982,016, discloses 16-aryl-13,14-dihydro-$PGE_2$ p-biphenyl esters useful for bone formation activity. U.S. Pat. No. 4,621,100, discloses substituted cyclopentanes useful for bone formation activity. U.S. Pat. No. 5,216,183, discloses cyclopentanones useful for bone formation activity.

Sodium fluoride may be used in combination with the compounds of this invention. The term sodium fluoride refers to sodium fluoride in all its forms (e.g., slow release sodium fluoride, sustained release sodium fluoride). Sustained release sodium fluoride is disclosed in U.S. Pat. No. 4,904,478. The activity of sodium fluoride is readily determined by those skilled in the art of biological protocols.

Bone morphogenetic protein may be used in combination with the compounds of this invention (e.g., see Ono et al., Promotion of the Osteogenetic Activity of Recombinant Human Bone Morphogenetic Protein by Prostaglandin $E_1$, Bone 19(6): 581-588 (1996)).

Any parathyroid hormone (PTH) may be used in combination with the compound of this invention. The term parathyroid hormone refers to parathyroid hormone, fragments or metabolites thereof and structural analogs thereof which can stimulate bone formation and increase bone mass. Also included are parathyroid hormone related peptides and active fragments and analogs of parathyroid related peptides (see PCT publication No. WO 94/01460). Such bone anabolic functional activity is readily determined by those skilled in the art of standard assays. A variety of these compounds are described and referenced below. However, other parathyroid hormone will be known to those skilled in the art. Exemplary parathyroid hormones are disclosed in the following references. "Human Parathyroid Peptide Treatment of Vertebral Osteoporosis", Osteoporosis Int., 3, (Supp 1): 199-203. "PTH 1-34 Treatment of Osteoporosis with Added Hormone Replacement Therapy: Biochemical, Kinetic and Histological Responses" Osteoporosis Int. 1: 162-170.

Any growth hormone or growth hormone secretagogue may be used in combination with the compounds of this invention. The term growth hormone secretagogue refers to a compound which stimulates the release of growth hormone or mimics the action of growth hormone (e.g., increases bone formation leading to increased bone mass). Such actions are readily determined by those skilled in the art of standard assays well known to those of skill in the art. A variety of these compounds are disclosed in the following published PCT patent applications: WO 95/14666; WO 95/13069; WO 94/19367; WO 94/13696; and WO 95/34311. However, other growth hormones or growth hormone secretagogues will be known to those skilled in the art. In particular, a preferred growth hormone secretagogue is N-[1(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-667. Other preferred growth hormone secretagogues include 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide or its L-tartaric acid salt; 2-amino-N-(1-(R)-benzyloxymethyl-2-(3a-(R)-(4-fluoro-benzyl)-2-methyl-3-oxo -2,3,3a,4,6,7-hexahydro-pyrazolo[4,3-c]pyridin-5-yl)-2-oxo-ethyl)isobutyramide; 2-amino-N-(2-(3a-(R)-benzyl-3-oxo-2,3,3a,4,6,7-hexahydro-pyrazolo[4,3-c]pyridin-5-yl)-1-(R) benzyloxymethyl-2-oxo-ethyl)isobutyramide; and 2-amino-N-(1-(2,4-difluoro-benzyloxymethyl)-2-oxo-2-(3-oxo-3a-pyridin-2-ylmethyl-2-(2,2,2-trifluoro-ethyl)-2,3,3a,4,6,7-hexahydro-pyrazolo[4,3-c]pyridin-5-yl)-ethyl)-2-methyl-propionamide.

The other therapeutic agent can be a steroid or a non-steroidal anti-inflammatory agent. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see *Paul A. Insel, Analgesic-Antipyretic and Antiinflammatory Agents and Drugs Employed in the Treatment of Gout, in Goodman & Gilman's The Pharmacological Basis of Therapeutics* 617-57 (Perry B. Molinhoff and Raymond W. Ruddon eds., $9^{th}$ ed 1996) and Glen R. Hanson,

*Analgesic, Antipyretic and Anti-Inflammatory Drugs in Remington: The Science and Practice of Pharmacy Vol II* 1196-1221 (A.R. Gennaro ed. 19th ed. 1995) which are hereby incorporated by reference in their entireties.

For arthritis, inflammation-mediated bone loss and other disorders that have an inflammatory component, preferred conventional treatments for use in combination therapy with the compounds and compositions of this invention include (without limitation) naproxen sodium (Anaprox® and Anaprox® DS, Roche), flurbiprofen (Ansaid®; Pharmacia), diclofenac sodium+misoprostil (Arthrotec®, Searle), valdecoxib (Bextra®, Pharmacia), diclofenac potassium (Cataflam® and Voltaren®, Novartis), celecoxib (Celebrex®, Pharmacia), sulindac (Clinoril®, Merck), oxaprozin (Daypro®, Pharmacia), salsalate (Disalcid®, 3M), diflunisal (Dolobid®, Merck), naproxen sodium (EC Naprosyn®, Roche), piroxicam (Feldene®, Pfizer), indomethacin (Indocin® and Indocin SR®, Merck), etodolac (Lodine® and Lodine XL®, Wyeth), meloxicam (Mobic®, Boehringer Ingelheim), ibuprofen (Motrin®, Pharmacia), naproxen (Naprelan®, Elan), naproxen (Naprosyn®, Roche), ketoprofen (Orudis® and Oruvail®, Wyeth), nabumetone (Relafen®, SmithKline), tolmetin sodium (Tolectin®, McNeil), choline magnesium trisalicylate (Trilisate®, Purdue Fredrick), and rofecoxib (Vioxx®, Merck).

In any case where pain in a component of the target disorder, the other therapeutic agent can be an analgesic. Useful analgesics include, but are not limited to, phenacetin, butacetin, acetaminophen, nefopam, acetoamidoquinone, and mixtures thereof.

For use against osteoporosis, Paget's disease and other disorders associated with bone deterioration, preferred conventional agents that may be used in combination with compounds and compositions of this invention include (without limitation) bisphosphonates (such as etidronate (Didronel®, Procter & Gamble), pamidronate (Aredia®, Novartis), and alendronate (Fosamax®, Merck)), tiludronate (Skelid®, Sanofi-Synthelabo, Inc.), risedronate (Actonel®, Procter & Gamble/Aventis), calcitonin (Miacalcin®), estrogens (Climara®, Estrace®, Estraderm®, Estratab®, Ogen®, Ortho-Est®, Vivelle®, Premarin®, and others) estrogens and progestins (Activella™, FemHrt®, Premphase®, Prempro®, and others), parathyroid hormone and portions thereof, such as teriparatide (Forteo®, Eli Lilly and Co.), selective estrogen receptor modulators (SERMs) (such as raloxifene (Evista®)) and treatments currently under investigation (such as other parathyroid hormones, sodium fluoride, vitamin D metabolites, and other bisphosphonates and selective estrogen receptor modulators).

Any method of the present invention can comprise administering an effective amount of a composition or pharmaceutical composition comprising at least one compound of this invention to a cell, tissue, organ, animal or patient in need of such modulation, treatment or therapy. Such a method can optionally further comprise co-administration or combination therapy for treating an IL-12 production related disorder, wherein the administering further comprises administering before, concurrently with, and/or after the compound of this invention, at least one additional active agent selected from a TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonistm. Suitable dosages are well known in the art. See, e.g., Wells et al., eds., Pharmacotherapy Handbook, 2.sup.nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

TNF antagonists suitable for compositions, combination therapy, co-administration, devices and/or methods of the present invention include, but are not limited to, anti-TNF antibodies (such as, Remicade (Infliximab) or Humira (adalimumab)) for example, or, antigen-binding fragments thereof, and receptor molecules which bind specifically to TNF (such as, for example, Enbrel (Etanercept)); compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

For clarifiation, a "tumor necrosis factor antibody," "TNF antibody," "TNF antibody," or fragment and the like decreases, blocks, inhibits, abrogates or interferes with TNF activity in vitro, in situ and/or preferably in vivo. For example, a suitable TNF human antibody of the present invention can bind TNFa and includes anti-TNF antibodies, antigen-binding fragments thereof, and specified mutants or domains thereof that bind specifically to TNFa. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

The foregoing and other useful combination therapies will be understood and appreciated by those of skill in the art. Potential advantages of such combination therapies include the ability to use less of each of the individual active ingredients to minimize toxic side effects, synergistic improvements in efficacy, improved ease of administration or use and/or reduced overall expense of compound preparation or formulation.

As used herein, the terms "animal", "subject" and "patient", include, but are not limited to, a cow, monkey, horse, sheep, pig, chicken, turkey, quail, cat, dog, mouse, rat, rabbit, guinea pig and human (preferably, a human).

As used herein, the term "pharmaceutically acceptable solvate," is a solvate formed from the association of one or more solvent molecules to one of the compounds of formula (I). The term solvate includes hydrates (e.g., mono-hydrate, dihydrate, trihydrate, tetrahydrate, and the like).

As used herein, the term "pre-osteoclast cell" is a cell capable of forming an osteoclast cell upon differentiation and/or fusion and includes without limitation, circulating monocytes and tissue macrophages (N. Kurihara et al., Endocrinology 126: 2733-41 (1990)). Without wishing to be bound by theory, pre-osteoclasts are converted to activated osteoclasts in a process thought to involve two factors produced by pre-osteoblasts, M-CSF and ODF. These factors activate certain genes that are needed for the conversion of a pre-osteoclast into an osteoclast.

The biological activities of a heterocyclic compound can be evaluated by a number of cell-based assays. One of such assays can be conducted using cells from human peripheral blood mononuclear cells (PBMC) or human monocytic cell line (THP-1). The cells are stimulated with a combination of human interferon-γ (IFNγ) and lipopolysaccharide or a combination of IFNγ and *Staphylococcus aureus* Cowan I in the presence of a test compound. The level of inhibition of IL-12 production can be measured by determining the amount of p70 by using a sandwich ELISA assay with anti-human IL-12 antibodies. $IC_{50}$ of the test compound can then be determined. Specifically, PBMC or THP-1 cells are incubated with the test compound. Cell viability was assessed using the bioreduction of MTS [3-(4,5-dimethylthiazol-2-yl)-5-(3-carboxymethoxyphenyl)-2-(4-sulfophenyl)-2H-tetrazolium] (Promega, Madison, Wis.).

A compound can also be evaluated by animal studies. For example, one of such studies involves the ability of a test compound to treat adjuvant arthritis (i.e., a IL-12 overproduction related disorder) in rats.

Responsiveness of a particular condition, disease or disorder to compounds and compositions of this invention can be measured directly by comparison against conventional drugs, or can be inferred based on an understanding of disease etiology and progression. There are a number of cellular and bone resorption assay systems that are widely accepted in the art as predictive of in vivo effects. As the bone resorption assay uses material that includes all bone cells, it is an ex vivo assay. Thus, the showing that a compound of this invention inhibits bone resorption in these assays is evidence of the clinical utility of these for treating or preventing conditions associated with excessive bone loss. Various scientific publications (such as Carano et al. J. Clin. Invest. 85: 456-461 (1990); Blair & Schlesinger, The Biology and Physiology of the Osteoclast, CRC Press, Eds., Gay, C. V. and Rifkin, B. R., pp. 259-288 (1992); and Vaananen et al., J. Cell Biology 111: 1305-1311 (1990)) support the fact that such assays are accepted as being predictive of in vivo activity. Furthermore, the in vitro effects of Herbimycin A on bone resorption were shown to correlate with in vivo activity (Yoneda et al., J. Clin. Invest. 91: 2791-95 (1993)).

Without further elaboration, it is believed that the above description has adequately enabled the present invention. The following specific embodiments are, therefore, to be construed as merely illustrative, and not limitative of the remainder of the disclosure in any way whatsoever. All of the references and publications cited herein are hereby incorporated by reference in their entirety.

EXAMPLES

Example 1

Preparation of Compound 1

The structures of compounds A-E referred to below are shown in Scheme 1 above.

To a solution of 2,4,6-trichloropyridine (3.65 g, 20 mmol) in 20 ml dioxane was added morpholine (1.75 ml, 20 mmol) and DIPEA (3.50 ml, 20 mmol). The mixture was heated at 85° C. for 5 hours. After cooling to room temperature, the reaction mixture was diluted with water and extracted with EtOAc (300 ml). The organic phase was dried ($Na_2SO_4$), filtered and evaporated in vacuo to afford a crude mixture of isomers A and B, which were separated by flash chromatography (Hexane-EtOAc, 9:1). Compound A (2.38 g, 51%) eluted first followed by compound B (1.05 g, 22,5%).

Analytical data for Compound A: $^1$H-NMR ($CDCl_3$) δ (ppm), 6.66 (s, 1H), 6.46 (s, 1H), 3.83-3.77 (m, 4H), 3.56-3.50 (m, 4H); ESMS clcd for $C_9H_{10}Cl_2N_2O$: 232.02; Found: 233.1 $(M+H)^+$.

To a solution of 3,4-dimethoxyphenylethyl alcohol (1.10 g, 6.0 mmol) in anhydrous DMF (15 ml) at 0° C. under the nitrogen, was added NaH (0.32 g, 8.0 mmol). The suspension was stirred for 0.5 hours at 0° C. then compound A (1.40 g, 6.0 mmol) was added as a solid. The mixture was warmed to room temperature and stirred for 12 hours. The reaction was quenched by ice brine and extracted with EtOAc (200 ml). The organic phase was washed with brine, dried ($Na_2SO_4$), filtered and evaporated in vacuo to afford a crude mixture of isomers C and D, which were separated by flash chromatography, which were separated by flash chromatography (Hexane-EtOAc, 8:2). Compound C (0.550 g, 24%) eluted first followed by compound D (1.25 g, 54,9%).

Analytical data for Compound C: $^1$H-NMR ($CDCl_3$) δ (ppm), 6.81-6.79 (m, 3H), 6.12 (s, 2H), 4.40 (t, J=7.2 Hz, 2H), 3.88 (s, 3H), 3.87 (s, 3H), 3.79 (t, J=4.8 Hz, 4H), 3.46 (t, J=4.8 Hz, 4H), 2.99 (t, J=7.2 Hz, 2H); ESMS clcd for $C_{19}H_{23}ClN_2O_4$: 378.13; Found: 379.1 $(M+H)^+$.

To compound C (220 mg, 0.58 mmol) was added anhydrous hydrazine (3 ml). The mixture was heated at 130-145° C. for 6 h. and quenched by brine (2 ml) and extracted with EtOAc (15 ml). The organic phase was washed with brine (5 ml) and water (5 ml×2) and dried ($Na_2SO_4$). The solvent was evaporated in vacuo to give a crude product E.

To a solution of compound E (200 mg, 0.53 mmol) and 3-indole carboxaldehyde (78 mg, 0.53 mmol) in MeOH (5 ml) was added catalytic amount of acetic acid (1 drop). The reaction mixture was stirred at room temperature for 12 h and a white solid was precipitated. The resulting precipitate was collected by filtration and washed with a minimal volume of methanol to give (55 mg) of N-{2-[2-(3,4-dimethoxy-phenyl)-ethoxy]-6-morpholin-4-yl-pyridin-4-yl}-N'-(1H-indol-3-ylmethylene)-hydrazine (compound 1) in 21% yield. Analytical data for compound 1: $^1$H-NMR ($CDCl_3$) δ (ppm), 8.40-8.25 (m, 2H), 7.95 (s, 1H), 7.48 (s, 1H), 7.42-7.36 (m, 2H), 7.32-7.22 (m, 2H), 6.83 (s, 3H), 5.96 (d, J=12 Hz, 2H), 4.45 (t, J=7.5 Hz, 2H), 3.90-3.80 (m, 10 H), 3.54-3.45 (m, 4H), 3.04 (t, J=7.5 Hz, 2H); ESMS calculated for $C_{28}H_{31}N_5O_4$: 501.24; Found: 502.3 $(M+H)^+$.

Example 2

Preparation of Compound 2

Compound 2, N-{6-[2-(3,4-dimethoxy-phenyl)-ethoxy]-4-morpholin-4-yl-pyridin-2-yl}-N'-(1H-indol-3-ylmethylene)-hydrazine, was prepared in a manner similar to that described for compound 1. Analytical data for compound 2: $^1$H-NMR (CDCl$_3$) δ (ppm), 8.26-8.40 (m 2H), 7.98 (s, 1H), 7.79 (s, 1H), 7.44-7.34 (m, 2H), 7.30-7.22 (m, 2H), 6.83 (s, 3H), 6.47 (s, 1H), 5.66 (s, 1H), 4.40 (t, J=7.2 Hz, 2H), 3.90-3.82 (m, 10 H), 3.38-3.30 (m, 4H), 3.02 (t, J=6.3 Hz, 2H); ESMS clcd for C$_{28}$H$_{31}$N$_5$O$_4$: 501.24; Found: 502.3 (M+H)$^+$.

Example 3

Preparation of Compound 3

Compound 3, N-{4-[2-(3,4-dimethoxy-phenyl)-ethoxy]-6-morpholin-4-yl-pyridin-2-yl}-N'-(1H-indol-3-ylmethylene)-hydrazine, was prepared in a manner similar to that described for compound 1. Analytical data for compound 3: $^1$H-NMR (CDCl$_3$) δ (ppm), 8.33 (d, J=7.8 Hz, 1H), 8.25 (s, 1H), 7.95 (s, 1H), 7.87 (s, 1H), 7.40-7.12 (m, 4H), 6.88-6.80 (m, 3H), 6.43 (s, 1H), 5.64 (s, 1H), 4.29 (t, J=6.9 Hz, 2H), 3.86 (s, 6H), 3.80-3.75 (m, 4H), 3.43-3.39 (m, 4H), 3.09 (t, J=7.2 Hz, 2 H); ESMS clcd for C$_{28}$H$_{31}$N$_5$O$_4$: 501.24; Found: 502.3 (M+H)$^+$.

Example 4

Preparation of Compound 4

A 25 mL round bottom flask was dried and charged with palladium acetate (10 mg, 0.05 mmol), binap (35 mg, 0.05 mmol) and toluene (8 mL). The flask and its contents were flushed with nitrogen for 5 minutes and stirred under nitrogen for an additional 10 minutes. To a dried 50 mL of round bottom flask was added cesium carbonate (0.88 g, 2.7 mmol), 5-amino-2,3-dimethylindole (100 mg, 0.65 mmol), 4-{2-chloro-6-[2-(3,4-dimethoxy-phenyl)-pyridin-4-yl}morpholine (200 mg, 0.54 mmol), and toluene (12 mL) followed by the palladium/binap solution prepared above. The resulting mixture was flushed with nitrogen for 5 min. and heated at reflux under niteogen for 4 hours. Thereaction mixture was cooled to room temperature, then concentrated. The crude residue was purified by flash column chromatography (1:4 Ethyl acetate/Hexane) to afford 84 mg (yield 32%) of compound 4, {6-[2-(3,4-Dimethoxy-phenyl)-ethoxy]-4-morpholin-4-yl-pyridin-2-yl}-(2,3-dimethyl-1H-indol-5-yl)-amine.

Analytical data for compound 4: $^1$H NMR (CDCl$_3$): δ (ppm) 7.69 (s, 1H); 7.40 (s, 1H); 7.20 (d, J=8.0 Hz, 1H); 7.02 (d, J=8.0 Hz, 2H); 6.82 (s, 2H); 6.16 (s, 1H); 5.72 (s, 1H); 5.59 (s, 1H); 4.44 (t, J=6.0 Hz, 2H); 3.89 (s, 6H); 3.72 (m, 4H); 3.12 (m, 4H); 3.02 (t, J=6.0 Hz, 2H); 2.36 (s, 3H); 2.16 (s, 3H). ESMS calcd (C$_{27}$H$_{32}$N$_4$O$_4$): 502.3; found: 503.5 (M+H)$^+$.

Example 5

Preparation of Compound 5

Compound 5, N-{4-[2-(3,4-Dimethoxy-phenyl)-ethoxy]-6-morpholin-4-yl-pyridin-2-yl}-N'-(3-methyl-benzylidene)-hydrazine, was prepared in a manner similar to that described for compound 1. Analytical data for compound 5: $^1$H NMR (CDCl$_3$): δ (ppm) 8.08 (s, 1H); 7.95 (s, 1H); 7.66 (s, 1H); 7.43 (m, 2H); 7.27 (m, 1H); 7.15 (d, J=6.0 Hz. 1H); 6.84 (d, J=6.0 Hz, 3H); 6.36 (d, J=3.0 Hz, 1H); 5.66 (d, J=3.0 Hz, 1H); 4.25 (t, J=6.0 Hz, 2H); 3.88 (m, 10H); 3.40 (t, J=6.0 Hz, 4H); 3.07 (t, J=6.0 Hz, 2H); 2.38 (s, 3H). ESMS calcd (C$_{27}$H$_{32}$N$_4$O$_4$): 476.2; found: 477.5 (M+H)$^+$.

Example 6

Preparation of Compound 6

Compound 6, N-{2-[2-(3,4-Dimethoxy-phenyl)-ethoxy]-6-morpholin-4-yl-pyridin-4-yl}-N'-(3-methyl-benzylidene)-hydrazine, was prepared in a manner similar to that described for compound 1. Analytical data for compound 6: $^1$H NMR (CDCl$_3$): δ (ppm) 7.65 (m, 2H); 7.45 (m, 2H); 7.27 (m, 1H); 7.16 (m, 1H); 6.82 (s, 2H); 5.95 (s, 1H); 5.89 (s, 1H); 4.42 (t, J=6.0 Hz, 2H); 3.86 (m, 10H); 3.31 (t, J=6.0 Hz, 4H); 3.00 (t, J=6.0 Hz, 2H); 2.39 (s, 3H). ESMS calcd (C$_{27}$H$_{32}$N$_4$O$_4$): 476.2; found: 477.5 (M+H)$^+$.

Example 7

Preparation of Compound 7

Compound 7, N-{6-[2-(3,4-Dimethoxy-phenyl)-ethoxy]-4-morpholin-4-yl-pyridin-2-yl}-N'-(3-methyl-benzylidene)-hydrazine, was prepared in a manner similar to that described for compound 1. Analytical data for compound 7: $^1$H NMR (CDCl$_3$): δ (ppm) 7.95 (s, 1H); 7.67 (s, 1H); 7.45 (m, 2H); 7.27 (m, 1H); 7.15 (m, 1H); 6.82 (m, 2H); 6.40 (d, J=3.0 Hz, 1H); 5.66 (d, J=3.0 Hz, 1H); 4.37 (t, J=6.0 Hz, 2H); 3.86 (m, 10H); 3.31 (t, J=6.0 Hz, 4H); 3.00 (t, J=6.0 Hz, 2H); 2.39 (s, 3H). ESMS calcd (C$_{27}$H$_{32}$N$_4$O$_4$): 476.2; found: 477.5 (M+H)$^+$.

Example 8

Preparation of Compound 8

Compound 8, {2-[2-(3,4-Dimethoxy-phenyl)-ethoxy]-6-morpholin-4-yl-pyridin-4-yl}-(2,3-dimethyl-1H-indol-5-yl)-amine, was prepared in a manner similar to that described for compound 4. Analytical data for compound 8: $^1$H NMR (CDCl$_3$): δ (ppm) 7.74 (s, 1H); 7.20 (d, J=9.0 Hz, 2H); 6.94 (m, 1H); 6.78 (m, 2H); 5.82 (s, 1H); 5.62 (m, 2H); 4.36 (t, J=6.0 Hz, 2H); 3.76 (m, 10H); 3.36 (t, J=6.0 Hz, 4H); 2.97 (t, J=6.0 Hz, 2H); 2.36 (s, 3H); 2.18 (s, 3H). ESMS calcd (C$_{27}$H$_{32}$N$_4$O$_4$): 502.3; found: 503.5 (M+H)$^+$.

Example 9

Preparation of Compound 9

Compound 9, {4-[2-(3,4-Dimethoxy-phenyl)-ethoxy]-6-morpholin-4-yl-pyridin-2-yl}-(2,3-dimethyl-1H-indol-5-yl)-amine, was prepared in a manner similar to that described for compound 4. Analytical data for compound 9: $^1$H NMR (CDCl$_3$): δ (ppm) 7.78 (s, 1H); 7.39 (s, 1H); 7.16 (d, J=9.0 Hz, 1H); 6.98 (m, 1H); 6.78 (m, 2H); 6.25 (s, 1H); 5.67 (s, 1H); 5.57 (s, 1H); 4.10 (t, J=6.0 Hz, 2H); 3.86 (m, 10H); 3.36 (t, J=6.0 Hz, 4H); 2.94 (t, J=6.0 Hz, 2H); 2.34 (s, 3H); 2.16 (s, 3H). ESMS calcd (C$_{27}$H$_{32}$N$_4$O$_4$): 502.3; found: 503.5 (M+H)$^+$.

Example 10

Preparation of Compound 10

Compound 10, {4-[2-(3,4-Dimethoxy-phenyl)-ethoxy]-6-morpholin-4-yl-pyridin-2-yl}-m-tolyl-amine, was prepared in a manner similar to that described for compound 4. Analytical data for compound 9: $^1$H NMR (CDCl$_3$): δ (ppm) 7.18 (m, 1H); 7.09 (m, 2H); 6.80 (m, 4H); 6.24 (s, 1H); 5.84 (s, 1H); 5.62 (s, 1H); 5.72 (s, 1H); 5.59 (s, 1H); 4.11 (t, J=6.0 Hz, 2H); 3.86 (s, 6H); 3.78 (t, J=6.0 Hz, 4H); 3.44 (t, J=6.0 Hz, 2H); 3.0 (t, J=6.0 Hz, 2H); 2.32 (s, 3H). ESMS calcd (C$_{27}$H$_{32}$N$_4$O$_4$): 449.2; found: 450.5 (M+H)$^+$.

Example 11

Preparation of Compound 11

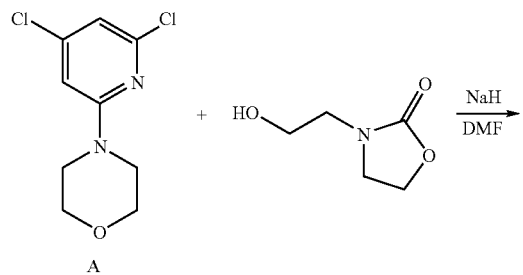

A

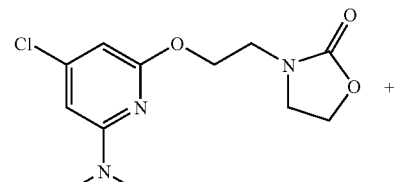

F

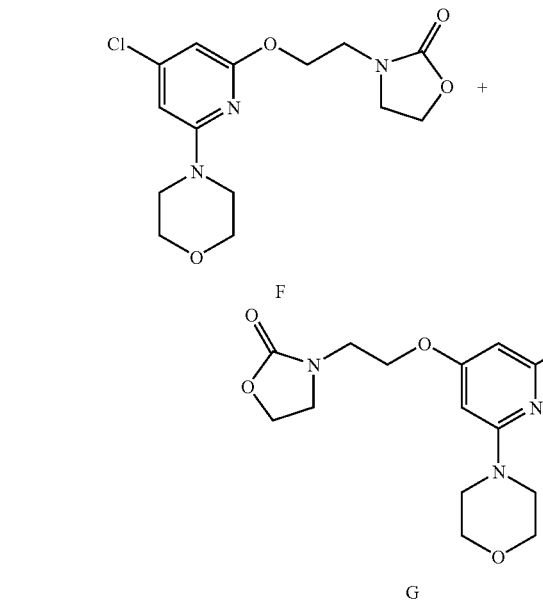

G

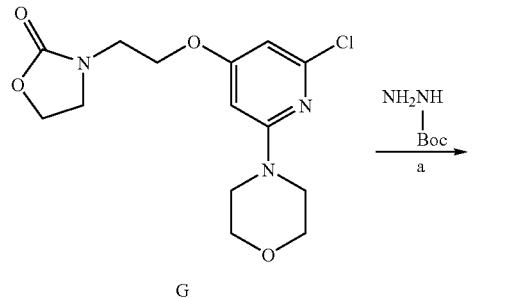

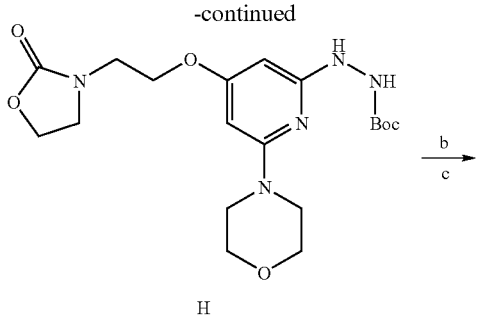

H

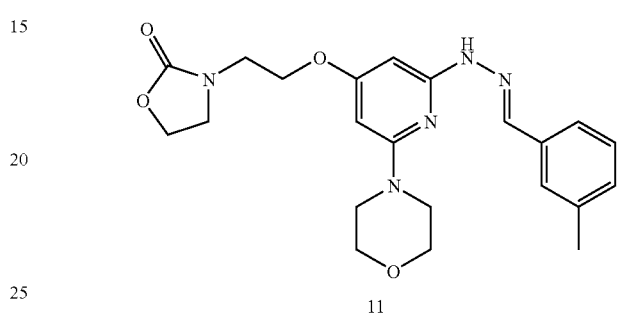

11

(a) Cs$_2$CO$_3$, Pd$_2$(dba)$_3$, DPPF, toluene
(b) TFA, CH$_2$Cl$_2$
(c) m-tolualdehyde, MeOH Compound 11 (3-(2-{2-[N'-(3-methyl-benzylidene)-hydrazino]-6-morpholin-4-yl-pyridin-4-yloxy}-ethyl)oxazolidin-2-one) was prepared as follows:

To a solution of 3-(2-hydroxyethyl)-oxazolidin-2-one (0.66 g, 5.0 mmol) in anhydrous DMF (10 ml) at 0° C. under nitrogen was added NaH (0.240 g, 6.0 mmol). The suspension was stirred for 0.5 h at 0° C. and solid compound A 4-(4,6-dichloro-pyridin-2-yl)-morpholine (see Example 1, 1.17 g, 5.0 mmol) was added. After the mixture warmed to room temperature and stirred for 12 h, the reaction was quenched with ice brine and extracted with EtOAc (200 ml). The organic phase was washed with brine, dried (Na$_2$SO$_4$), filtered and evaporated in vacuo. The isomers F and G were separated by flash chromatography (Hexane EtOAc, 3:1). ESMS clcd for F and G C$_{14}$H$_{18}$ClN$_3$O$_4$: 327.10; Found: 328.2 (M+H)

A mixture of compound G 3-[2-(2-chloro-6-morpholin-4-yl-pyridin-4-yloxy)-ethyl]-oxazolidin-2-one (165 mg, 0.50 mmol), t-butylcarbazate (135 mg, 1.0 mmol), Pd$_2$(dba)$_3$ (20 mg, 0.02 mmol), DPPF (35 mg, 0.06 mmol), Cs$_2$CO$_3$ (325 mg, 1.0 mmol) and toluene (3 ml) in a sealed tube under the nitrogen, was heated at 100° C. for 16 h. The reaction mixture was allowed to cool to room temperature, diluted with dichloromethane, filtered and concentrated. The crude product was then purified by flash column chromatography on silica gel (Hexane EtOAc, 1:1), to give compound H, N-{6-morpholi-4-yl-4-[2-(2-oxo-oxozolidin-3-yl)-ethoxy]-pyridin-yl}-hydrazinecarboxylic acid tert-butyl ester (130 mg, 61%).

To a solution of compound H (120 mg, 0.28 mmol) in anhydrous CH$_2$Cl$_2$ (3 ml) was added trifluoroacetic acid (TFA) (2 ml) and the mixture was heated at 50° C. for 5 h. The solvent was evaporated to give crude 3-[2-(2-hydrazino-6-morpholin-4-yl-pyridin-4-yloxy)-ethyl]-oxazolidin-2-one trifluoro-acetic salt. The crude product was then dissolved in methanol (4 ml) and to the solution was added m-tolualdehyde (40 mg, 0.33 mmol) and acetic acid (1 drop). The reaction mixture was stirred at room temperature for 12 h; a white solid was precipitated. The resulting precipitate was collected by filtration and washed with a small amount of methanol to give 85 mg (71%) 3-(2-{2-[N'-(3-methyl-benzylidene)-hydrazino]-6-morpholin-4-yl-pyridin-4-yloxy}-ethyl)oxazolidin-2-one.

$^1$H-NMR (CDCl$_3$) δ (ppm), 7.82 (s, 1H), 7.48-7.45 (m, 2H), 7.30-7.25 (m, 2H), 7.17-7.12 (m, 1H), 6.36 (d, J=1.5 Hz, 1H) 5.61 (d, J=1.8 Hz, 1H), 4.35 (t, J=6.6 Hz, 2H), 4.27 (t, J=4.8 Hz, 2H), 3.82-3.74 (m, 6H), 3.70 (t, J=4.8 Hz, 2H), 3.42 (t, J=4.8 Hz, 4H), 2.39 (s, 3H).

ESMS calculated for C$_{22}$H$_{27}$N$_5$O$_4$: 425.21; Found: 426.1 (M+H)$^+$.

Example 12

Synthesis of (N-[3,5-Difluoro-4-morpholin-4-yl-6-(2-morpholin-4-yl-ethoxy)-pyridin-2-yl]-N'-(3-methyl-benzylidene)-hydrazine)

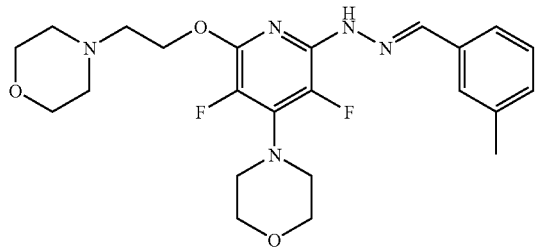

4-(2,3,5,6-Tetrafluoro-pyridin-4-yl)-morpholine: Pentafluoropyridine (3.4 g; 20 mmol) was dissolved in dichloromethane (50 mL) and chilled in an ice bath. To the solution was added morpholine (3.48 g; 40 mmol) and the reaction was allowed to warm to room temperature with stiffing overnight. The organic phase was washed with saturated ammonium chloride solution (2×20 mL), dried over magnesium sulfate, evaporated, and purified by column chromatography to give 4-(2,3,5,6-tetrafluoro-pyridin-4-yl)-morpholine.

4-[2,3,5-Trifluoro-6-(2-morpholin-4-yl-ethoxy)-pyridin-4-yl]-morpholine: 4-(2,3,5,6-Tetrafluoro-pyridin-4-yl)-morpholine (2.36 g; 10 mmol) was dissolved in tetrahydrofuran (50 mL). To the solution was added 4-(2-hydroxyethyl)-morpholine (1.57 g; 12 mmol) followed by sodium hydride (288 mg; 12 mmol), and it was stirred overnight. The solvent was then evaporated, and the solid was purified by column chromatography to give 4-[2,3,5-trifluoro-6-(2-morpholin-4-yl-ethoxy)-pyridin-4-yl]-morpholine (3.3 g).

Compound 12: 4-[2,3,5-Trifluoro-6-(2-morpholin-4-yl-ethoxy)-pyridin-4-yl]-morpholine (1.2 g; 3.5 mmol) and hydrazine (2 g) were added to dioxane (10 mL) and heated to 100° C. for six hours. The solvent was evaporated, and the residue was dissolved in dichloromethane (20 mL) and washed with a 10% sodium carbonate solution (2 mL). It was dried over magnesium sulfate, and evaporated, to give crude [3,5-Difluoro-4-morpholin-4-yl-6-(2-morpholin-4-yl-ethoxy)-pyridin-2-yl]-hydrazine. The crude product was then dissolved in ethanol. To the solution was added one drop of acetic acid, and m-tolylaldehyde (600 mL; 5 mmol) and it was heated at 60° C. overnight. The solvent was then evaporated, and the residue was purified by column chromatography to give Compound 12 (850 mg). Theoretical Mass Ion: 461.1; observed MH$^+$peak: 462.1.

Example 13

Synthesis of N-[3,5-Difluoro-2-morpholin-4-yl-6-(2-morpholin-4-yl-ethoxy)-pyridin-4-yl]-N'-(3-methyl-benzylidene)-hydrazine

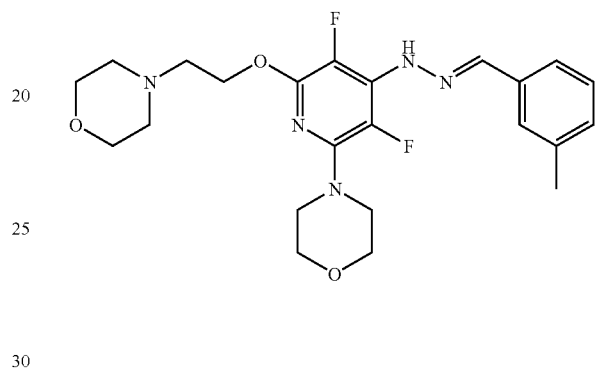

N-(3-Methyl-benzylidene)-N'-(2,3,5,6-tetrafluoro-pyridin-4-yl)-hydrazine: Pentafluoropyridine (3.4 g; 20 mmol) was dissolved in dichloromethane (50 mL) and chilled in an ice bath. To the solution was added hydrazine (640 mg; 22 mmol) and it was stirred overnight. The solvent was evaporated, and the residue was dissolved in dichloromethane (50 mL) and washed with a 10% sodium carbonate solution (5 mL). It was dried over magnesium sulfate, and evaporated, to give crude 2,3,5,6-tetrafluoro-pyridin-4-yl-hydrazine. The crude product was then dissolved in ethanol. To the solution was added one drop of acetic acid, and m-tolylaldehyde (1.45 g; 12 mmol) and it was heated at 60° C. overnight. The resulting precipitate was filtered and dried to give N-(3-methyl-benzylidene)-N'-(2,3,5,6-tetrafluoro-pyridin-4-yl)-hydrazine (2.2 g).

N-(3-Methyl-benzylidene)-N'-[2,3,5-trifluoro-6-(2-piperidin-1-yl-ethoxy)-pyridin-4-yl]-hydrazine: N-(3-methyl-benzylidene)-N'-(2,3,5,6-tetrafluoro-pyridin-4-yl)-hydrazine (2.2 g; 7.8 mmol) was dissolved in tetrahydrofuran (100 mL) and to the solution was added 4-(2-hydroxyethyl)-morpholine (1.3 g; 10 mmol) followed by sodium hydride (480 mg; 20 mmol). The solution was stirred at reflux for 24 hours. The solvent was then evaporated, and the solid was purified by column chromatography to give N-(3-methyl-benzylidene)-N'-[2,3,5-trifluoro-6-(2-piperidin-1-yl-ethoxy)-pyridin-4-yl]-hydrazine (830 mg).

Compound 13: N-(3-methyl-benzylidene)-N'-[2,3,5-trifluoro-6-(2-piperidin-1-yl-ethoxy)-pyridin-4-yl]-hydrazine (784 mg; 2 mmol) was dissolved in neat morpholine (2 mL) and heated in a sealed tube using microwave heating to 150° C. for ten minutes. The crude solution was purified by column chromatography to give Compound 13 (550 mg). Theoretical Mass Ion: 461.1; observed MH$^+$peak: 462.1.

Examples 14-21

Additional compounds according to the invention were prepared by methods similar to the methods of Examples 1-13, supra.

Compound 14: N-(3-Methyl-benzylidene)-N'-[4-morpholin-4-yl-6-(2-morpholin-4-yl-ethoxy)-pyridin-2-yl]-hydrazine

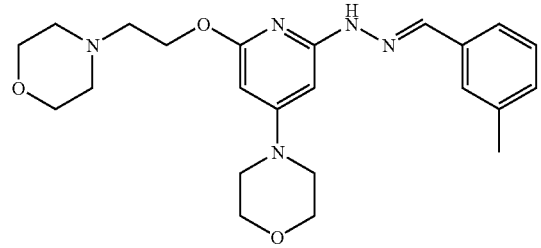

ESMS calculated for $C_{23}H_{31}N_5O_3$: 425.24; Found: 426.1 (M+H)$^+$.

Compound 15

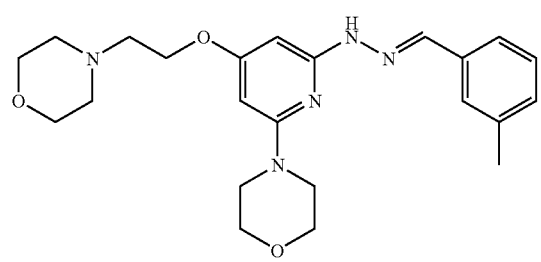

{2-[N'-(3-Methyl-benzylidene)-hydrazino]-6-morpholin-4-yl-pyridin-4-yl}-(2-morpholin-4-yl-ethyl)-amine ESMS calculated for $C_{23}H_{31}N_5O_3$: 425.24; Found: 426.2 (M+H)$^+$.

Compound 16

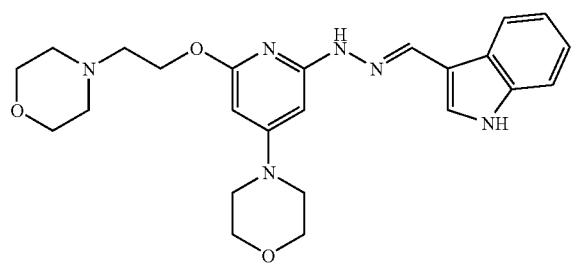

N-(1H-Indol-3-ylmethylene)-N'-[4-morpholin-4-yl-6-(2-morpholin-4-yl-ethoxy)-pyridin-2-yl]-hydrazine ESMS calculated for $C_{24}H_{30}N_6O_3$: 450.24; Found: 451.1 (M+H)$^+$.

Compound 17

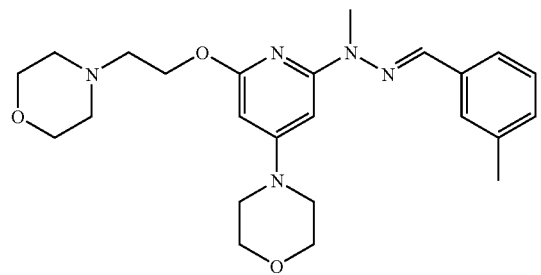

N-Methyl-N'-(3-methyl-benzylidene)-N-[4-morpholin-4-yl-6-(2-morpholin-4-yl-ethoxy)-pyridin-2-yl]-hydrazine ESMS calculated for $C_{24}H_{33}N_5O_3$: 439.26; Found: 440.2 (M+H)$^+$.

Compound 18

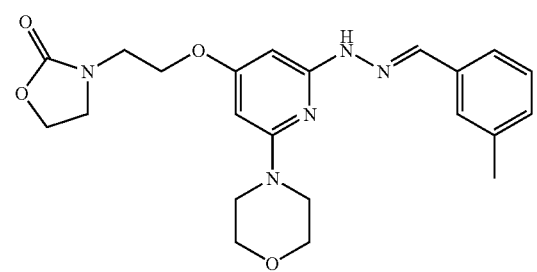

3-(2-{2-[N'-(3-Methyl-benzylidene)-hydrazino]-6-morpholin-4-yl-pyridin-4-yloxy}-ethyl)-oxazolidin-2-one ESMS calculated for $C_{22}H_{27}N_5O_4$: 425.21; Found: 426.1 (M+H)$^+$.

Compound 19

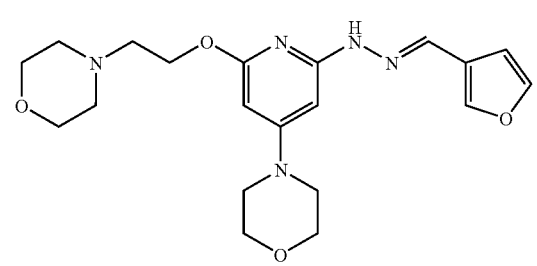

N-Furan-3-ylmethylene-N'-[4-morpholin-4-yl-6-(2-morpholin-4-yl-ethoxy)-pyridin-2-yl]-hydrazine ESMS calculated for $C_{20}H_{27}N_5O_4$: 401.21; Found: 402.1 $(M+H)^+$.

Compound 20

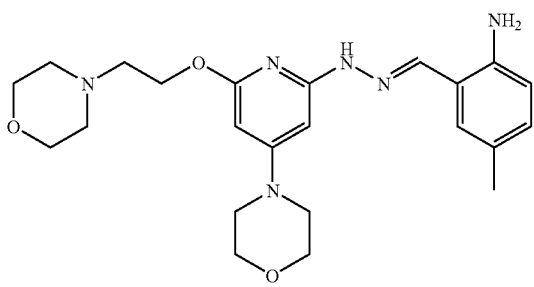

4-Methyl-2-{[4-morpholin-4-yl-6-(2-morpholin-4-yl-ethoxy)-pyridin-2-yl]-hydrazonomethyl}-phenylamine ESMS calculated for $C_{23}H_{32}N_6O_3$: 440.25; Found: 4410.1 $(M+H)^\pm$.

Compound 21

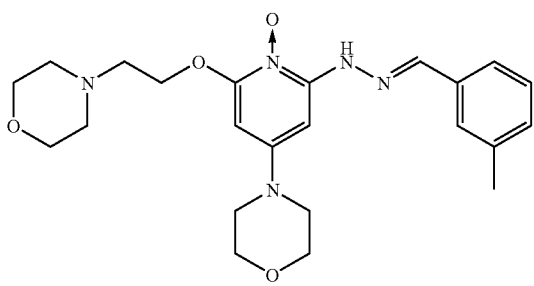

N-(3-Methyl-benzylidene)-N'-[4-morpholin-4-yl-6-(2-morpholin-4-yl-ethoxy)-1-oxy-pyridin-2-yl]-hydrazine ESMS calculated for $C_{23}H_{31}N_5O_4$: 441.24; Found: 442.1 $(M+H)^+$.

Example 22

In vitro Assays

Reagents. *Staphylococcus aureus* Cowan I (SAC) is obtained from Calbiochem (La Jolla, Calif.), and lipopolysaccharide (LPS, *Serratia marscencens*) is obtained from Sigma (St. Louis, Mo.). Human and mouse recombinant IFNγ are purchased from Boehringer Mannheim (Mannheim, Germany) and Pharmingen (San Diego, Calif.), respectively.

Human In Vitro Assay. Human PBMC were isolated by centrifugation using Ficoll-Paque (Pharmacia Biotech, Uppsala, Sweden) and prepared in RPMI medium supplemented with 10% fetal calf serum (FCS), 100 U/mL penicillin, and 100 μg/mL streptomycin. PBMC were plated in wells of a 96-well plate at a concentration of $5\times10^5$ cells/well, and primed by adding IFNγ (30 U/mL) for 22 h and stimulated by adding LPS (1 vg/mL), or by adding IFNγ (100 U/mL) and then stimulated by adding SAC (0.01%). A test pyridine compound was dissolved in DMSO, and added to wells of the 96-well plate. The final DMSO concentration was adjusted to 0.25% in all cultures, including the compound-free control. Human THP-1 cells were plated in wells, primed by adding IFNγ (100 U/mL) for 22 h and stimulated by adding SAC (0.025%) in the presence of different concentrations of the pyridine compound. Cell-free supernatants were taken 18 h later for measurement of cytokines. Cell viability was assessed using the bioreduction of MTS. Cell survival was estimated by determining the ratio of the absorbance in compound-treated groups versus compound-free control.

The supernatant was assayed for the amount of IL-12p40, IL-12p70, or IL-10 by using a sandwich ELISA with anti-human antibodies, i.e., a Human IL-12 p40 ELISA kit from R&D Systems (Berkeley, Calif.), and a Human IL-12 p70 or IL-10 ELISA kit from Endogen (Cambridge, Mass.). Assays were based on the manufacturer's instructions.

Murine In Vitro Assay. Balb/c mice (Taconic, Germantown, N.Y.) were immunized with *Mycobacterium tuberculosis* H37Ra (Difco, Detroit, Mich.). The splenocytes were harvested 5 days and prepared in RPMI medium supplemented with 10% FCS and antibiotics in a flat bottom 96-well plate with $1\times10^6$ cells/well. The splenocytes were then stimulated with a combination of IFNγ (60 ng/mL) and SAC (0.025%) [or LPS (20 vg/mL)] in the presence of a test compound. Cell-free supernatants were taken 24 h later for the measurement of cytokines. The preparation of compound and the assessment of cell viability were carried out as described above. Mouse IL-12 p'70, IL-10, IL-1β, and TNFα were measured using ELISA kits from Endogen, according to the manufacturer's instructions.

The biological activities of pyridine compounds were tested on human PBMC or THP-1 cells. $IC^{50}$ data is shown in Table 1 below.

TABLE 1

| Compound | $IC^{50}$ |
|---|---|
| 1 | 10 nM |
| 2 | 5 nM |
| 3 | 0.8 μM |
| 4 | 197 nM |
| 5 | 2 μM |
| 6 | 5 nM |
| 7 | 14.1 nM |
| 8 | 28 nM |
| 9 | 350 nM |
| 10 | 5 μM |
| 11 | 927 nM |
| 12 | >1000 nM |
| 13 | 148 nM |
| 14 | 25 nM |
| 15 | 714.8 nM |
| 16 | 36.6 nM |
| 17 | 14.2 nM |
| 18 | 927 nM |
| 19 | 5000 nM |
| 20 | 11.4 nM |
| 21 | 86 nM |

Example 23

In vivo Assays

Treatment of adjuvant arthritis in rats: Adjuvant arthritis (AA) can be induced in rats, and the ability of a compound of the invention to prevent, reduce, or reverse the induced arthritis can be measured (see, e.g., Example 24, infra). For example, AA can be induced by the intracutaneous injection of 0.1 mL of a 10 mg/mL bacterial suspension made from ground, heat-killed *Mycobacterium tuberculosis* H37Ra suspended in incomplete Freund's adjuvant. Rats are then given a test compound, and the development of polyarthritis is monitored daily by macroscopic inspection and assignment of an arthritis index to each animal, e.g., during the critical period (days 10 to 25 post-immunization).

Treatment of Crohn's disease in dinitrobenzene sulfonic acid-induced inflammatory bowel syndrome model rats: Wistar derived male or female rats weighing 200±20 g and fasted for 24 hours are used. Distal colitis is induced by intra-colonic instillation of 2,4-dinitrobenzene sulfonic acid (DNBS, 25 mg in 0.5 mL ethanol 30%) after which air (2 mL) is gently injected through the cannula to ensure that the solution remained in the colon. A test compound and/or vehicle is administered orally 24 and 2 hours before DNBS instillation and then daily for 5 days. One control group is similarly treated with vehicle alone while the other is treated with vehicle plus DNBS. The animals are sacrificed 24 hours after the final dose of test compound administration and each colon is removed and weighed. Colon-to-body weight ratio is then calculated for each animal according to the formula: Colon (g)/BW×100. The "Net" increase in ratio of Vehicle-control+DNBS group relative to Vehicle-control group is used as a base for comparison with test substance treated groups and expressed as "% Deduction."

Treatment of Crohn's disease in CD4$^+$CD45Rb$^{high}$ T cell-reconstituted SCID colitis model mice: Spleen cells are prepared from normal female BALB/c mice. For cell purification, the following anti-mouse antibodies are used to label non-CD4$^+$T cells: B220 (RA3-6B2), CD11b (M1/70), and CD8c (53-6.72). All antibodies are obtained from BioSource (Camarillo, Calif.). M450 anti-rat IgG-coated magnetic beads (Dynal, Oslo, Norway) are used to bind the antibodies and negative selection is accomplished using an MPC-1 magnetic concentrator. The enriched CD4$^+$cells are then labeled for cell sorting with FITC-conjugated CD45RB (16A, Pharmingen, San Diego, Calif.) and PE-conjugated CD4 (CT-CD4, Caltag, Burlingame, Calif.). CD4$^+$CD45RB$^{high}$ cells are operationally defined as the upper 40% of CD45RB-staining CD4$^+$cells and sorted under sterile conditions by flow cytometry. Harvested cells are resuspended at 4×10$^6$/mL in PBS and injected 100 µL intraperitoneally into female C.B-17 SCID mice. Pyridine compounds of this invention and/or vehicle is orally administered once a day, 5 days per week, starting the day following the transfer. The transplanted SCID mice are weighed weekly and their clinical condition was monitored.

Colon tissue samples are fixed in 10% buffered formalin and embedded in paraffin. Sections (4 µm) collected from ascending, transverse, and descending colon are cut and stained with hematoxylin and eosin. The severity of colitis is determined based on histological examination of the distal colon sections, whereby the extent of colonic inflammation is graded on a scale of 0-3 in each of four criteria: crypt elongation, cell infiltration, depletion of goblet cells, and the number of crypt abscesses.

LP lymphocytes are isolated from freshly obtained colonic specimens. After removal of payer's patches, the colon is washed in Ca/Mg-free HBSS, cut into 0.5 cm pieces and incubated twice in HBSS containing EDTA (0.75 mM), DTT (1 mM), and antibiotics (amphotericin 2.5 vg/mL, gentamicin 50 µg/mL from Sigma) at 37° C. for 15 min. Next, the tissue is digested further in RPMI containing 0.5 mg/mL collagenase D, 0.01 mg/mL DNase I (Boehringer Manheim), and antibiotics at 37° C. LP cells are then layered on a 40-100% Percoll gradient (Pharmacia, Uppsala, Sweden), and lymphocyte-enriched populations are isolated from the cells at the 40-100% interface.

To measure cytokine production, 48-well plates are coated with 10 µg/mL murine anti-CD3ε antibody (145-2C11) in carbonate buffer (PH 9.6) overnight at 4° C. 5×10$^5$ LP cells are then cultured in 0.5 ml of complete medium in precoated wells in the presence of 1 µg/mL soluble anti-CD28 antibody (37.51). Purified antibodies are obtained from Pharmingen. Culture supernatants are removed after 48 h and assayed for cytokine production. Murine IFNγ is measured using an ELISA kit from Endogen (Cambridge, Mass.), according to the manufacturer's instructions.

Example 24

Human peripheral blood mononuclear cells (PBMC) are isolated from healthy donor blood. The cells are seeded in multi-well plates at 7.5×10$^5$ cells/ml in RPMI 1640 medium including 10% FBS. Osteoclast formation is induced with 20 ng/ml of recombinant human receptor activator of NF-kB-ligand (RANKL) and 10 ng/ml of human M-CSF in the presence of various doses of test compounds. After 48 hours of culture, RANKL and M-CSF is replenished and further cultured for 2 days. Then, the cultured cells are stained for tartrate-resistant acid phosphatase (TRAP). Osteoclasts are identified as TRAP-positive cells with more than 3 nuclei.

Total cell viability is assessed by CCK-8 assay (Dojindo, Gaithersburg, Md.) with 24 hour incubation.

Example 25

In vivo Adjuvant Arthritis Assay

Treatment of adjuvant arthritis in rats: Adjuvant arthritis (AA) was induced in female Lewis rats by the intracutaneous injection (base of the tail) of 0.1 mL of a 10 mg/mL bacterial suspension made from ground, heat-killed *Mycobacterium tuberculosis* H37Ra suspended in incomplete Freund's adjuvant. Rats were given a test compound orally once a day for 7 days (day 7-14), starting day 7 after mycobacterium induction. The development of polyarthritis was monitored daily by macroscopic inspection and assignment of an arthritis index to each animal, during the critical period (days 10 to 25 post-immunization).

The intensity of polyarthritis was scored according to the following scheme: (a) Grade each paw from 0 to 3 based on erythema, swelling, and deformity of the joints: 0 for no erythema or swelling; 0.5 if swelling is detectable in at least one joint; 1 for mild swelling and erythema; 2 for swelling and erythema of both tarsus and carpus; and 3 for ankylosis and bony deformity.

Maximum score for all 4 paws was thus 12. (b) Grade for other parts of the body: for each ear, 0.5 for redness and another 0.5 if knots are present; 1 for connective tissue swelling (saddle nose); and 1 for the presence of knots or kinks in the tail. The highest possible arthritic index was 16.

Experiments with the AA model were repeated four times. Oral administration of a pyridine compound of this invention (N-(3-Methyl-benzylidene)-N'[4-morpholin-4-yl-6-(2-morpholin-4-yl-ethoxy)-pyridin-2-yl]-hydrazine, Compound 14) reproducibly reduced the arthritic score and delayed the development of polyarthritis in a dose-dependent manner (see FIG. 1). The arthritis score used in this model was a reflection of the inflammatory state of the structures monitored and the results therefore shows the ability of the test compound to provide relief for this aspect of the pathology.

Other Embodiments All of the features, specific embodiments and particular substituents disclosed herein may be combined in any combination. Each feature, embodiment or substituent disclosed in this specification may be replaced by an alternative feature, embodiment or substituent serving the same, equivalent, or similar purpose. In the case of chemical compounds, specific values can be combined in any combination resulting in a stable structure. Furthermore, specific values (whether preferred or not) for substituents in one type of chemical structure may be combined with values for other substituents (whether preferred or not) in the same or different type of chemical structure. Thus, unless expressly stated otherwise, each feature, embodiment or substituent disclosed is only an example of a generic series of equivalent or similar features feature, embodiments or substituents.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of inhibiting IL-23 and/or IL-27 production in a subject, comprising administering to the subject an effective amount of a compound of formula (I):

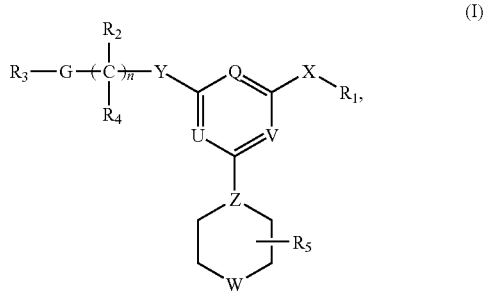

(I)

or a pharmaceutically acceptable salt thereof,
wherein,
$R_1$ is

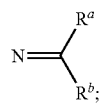

$R_2$ and $R_4$ are, independently, H, an optionally substituted alkyl, an optionally substituted alkylcarbonyl, —$OR^k$, —$SR^k$, —$NR^hR^j$, hydroxylalkyl, —$C(O)R^c$, —$OC(O)R^c$, —$SC(O)R^c$, —$NR^kC(O)R^c$, —$C(S)R^c$, —$OC(S)R^c$, —$SC(S)R^c$, —$NR^kC(S)R^c$, —$C(NR)R^c$, —$OC(NR)R^c$, —$SC(NR)R^c$, —$NR^kC(NR)R^c$, —$SO_2R^c$, —$S(O)R^c$, —$NR^kSO_2R^c$, —$OS(O)_2R^c$, —$OP(O)R^cR^c$, —$P(O)R^cR^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or $R_2$ and $R_4$ taken together are =O, =S, or =NR;

$R_3$ is an optionally substituted cyclyl, an optionally substituted cycloalkyl, an optionally substituted heterocyclyl, an optionally substituted heterocycloalkyl, an optionally substituted aryl, or an optionally substituted heteroaryl;

$R_5$ is —H, alkyl, alkylcarbonyl, halo, nitro, nitroso, cyano, azido, isothionitro, —$OR^P$ or —$SR^P$; and $R^P$ is —H, alkyl, or alkylcarbonyl;

n, for each occurrence, is independently 0, 1, 2, 3, 4, 5, 6 or 7;

X is NH;
Y is O;
Z is N;
W is O;
G is absent; and one of Q, U and V is N, and the other two are each $CR^g$ and each $CR^g$ may be the same or different;

wherein:

R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, —$C(O)R^c$, —$OR^k$, —$SR^k$, —$NR^hR^j$, hydroxylalkyl, nitro, cyano, haloalkyl, aminoalkyl, or —$S(O)_2R^c$;

$R^a$ is H and $R^b$ is optionally substituted aryl;

$R^c$ is H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —$OR^k$, —$SR^k$, —$NR^hR^j$, hydroxylalkyl, alkylcarbonylalkyl, mercaptoalkyl, aminoalkyl, sulfonylalkyl, sulfonylaryl, or thioalkoxy;

$R^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —$OR^k$, —$SR^k$, —$NR^hR^j$, hydroxylalkyl, alkylcarbonylalkyl, mercaptoalkyl, aminoalkyl, sulfonylalkyl, sulfonylaryl, thioalkoxy, —$C(O)R^c$, —$OC(O)R^c$, —$SC(O)R^c$, —$NR^kC(O)R^c$, —$C(S)R^c$, —$OC(S)R^c$, —$SC(S)R^c$, —$NR^kC(S)R^c$, —$C(NR)R^c$, —$OC(NR)R^c$, —$SC(NR)R^c$, —$NR^kC(NR)R^c$, —$SO_2R^c$, —$S(O)R^c$, —$NR^kSO_2R^c$, —$OS(O)_2R^c$, —$OP(O)R^cR^c$, —$P(O)R^cR^c$, halo, aminoalkyl, mercaptoalkyl, cyano, nitro, nitroso, or azide;

$R^h$ and $R^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or $R^h$ and $R^j$ taken together with the N to which they are attached is an optionally substituted heterocyclyl, an optionally substituted heterocycloalkyl, or an optionally substituted heteroaryl; and $R^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl.

2. The method of claim 1, further comprising inhibiting $T_H1$ lymphocyte proliferation.

3. The method of claim 2, further comprising inhibiting the production of IL-12.

4. The method of claim 1, wherein one of Q, U and V is N, and the other two are independently selected from the group consisting of CH, CF, C(CN), CCl, C(CH$_3$), C(OCH$_3$), C(OCF$_3$), and C(CF$_3$).

5. The method of claim 4, wherein U is N, and Q and V each are CH.

6. The method of claim 4, wherein R$_3$ is

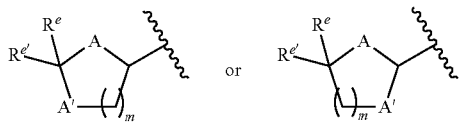

or wherein
each of A and A', independently, is O, S, NH or NR$^Y$, wherein R$^Y$ is lower alkyl;
each of R$^e$ and R$^{e'}$, independently is H, optionally substituted alkyl, substituted aryl, or substituted heteroaryl; and
m is 1 or 2.

7. The method of claim 1, wherein R$^b$ is

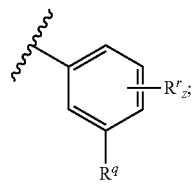

wherein
$R^q$ is H, halogen, CN, optionally substituted alkyl, optionally substituted cyclyl, optionally substituted alkyloxy, optionally substituted alkylcarbonyl, optionally substituted alkyloxycarbonyl, optionally substituted aryloxycarbonyl, optionally substituted heteroaryloxycarbonyl, hydroxyalkyl, alkylamino, or alkylaminocarbonyl;

each $R^r$ is, independently, H, halogen, NO$_2$, CN, optionally substituted alkyl, optionally substituted aryl, optionally substituted heteroaryl, OR$^k$, OC(O)R$^k$, SO$_2$R$^k$, S(O)R$^k$, S(O$_2$)NR$^h$R$^j$, SR$^k$, NR$^k$COR$^k$, NR$^k$C(O)OR$^k$, NR$^k$C(O)NR$^h$R$^j$, NR$^k$SO$_2$R$^k$, COR$^k$, C(O)OR$^k$, or C(O)NR$^h$R$^j$; and z is 0, 1, 2, 3, or 4.

8. The method of claim 7, wherein:
$R^q$ is H, methyl, ethyl, propyl, cyclopropyl, methoxy, ethoxy, methoxycarbonyl, or halogen;

each $R^r$ is, independently, F, Cl, CN, methyl, methoxy, ethoxy, —NH$_2$, —NHCH$_3$, —N(CH$_3$)$_2$, —NHCH$_2$CH$_3$, —N(CH$_2$CH$_3$)$_2$, OC(O)CH$_3$, OC(O)C$_2$H$_5$, C(O)OH, C(O)OC$_2$H$_5$, C(O)NH$_2$, NHC(O)CH$_3$, or S(O$_2$)NH$_2$;

$R^i$ is H, methyl, ethyl, or acetyl, and
z is 0, 1, or 2.

9. The method of claim 7, wherein one of Q, U and V is N, and the other two are each CH.

10. The method of claim 7, wherein R$_3$ is pyridinyl, 1-oxy-pyridinyl, 1H-pyridin-2-one, morpholin-4-yl, 4-methyl-piperazin-1-yl, or 2-oxo-oxazolidin-3-yl.

11. The method of claim 1, wherein the compound of formula (I) is selected from the group consisting of:

N-{2-[2-(3,4-Dimethoxy-phenyl)-ethoxy]-6-morpholin-4-yl-pyridin-4-yl}-N'-(1H-indol-3-ylmethylene)-hydrazine;

N-{6-[2-(3,4-Dimethoxy-phenyl)-ethoxy]-4-morpholin-4-yl-pyridin-2-yl}-N'-(1H-indol-3-ylmethylene)-hydrazine;

N-{4-[2-(3,4-Dimethoxy-phenyl)-ethoxy]-6-morpholin-4-yl-pyridin-2-yl}-N'-(1H-indol-3-ylmethylene)-hydrazine;

N-{4-[2-(3,4-Dimethoxy-phenyl)-ethoxy]-6-morpholin-4-yl-pyridin-2-yl}-N'-(3-methyl-benzylidene)-hydrazine;

N-{2-[2-(3,4-Dimethoxy-phenyl)-ethoxy]-6-morpholin-4-yl-pyridin-4-yl}-N'-(3-methyl-benzylidene)-hydrazine;

N-{6-[2-(3,4-Dimethoxy-phenyl)-ethoxy]-4-morpholin-4-yl-pyridin-2-yl}-N'-(3-methyl-benzylidene)-hydrazine;

3-(2-{2-[N'-(3-methyl-benzylidene)-hydrazino]-6-morpholin-4-yl-pyridin-4-yloxy}-ethyl)poxazolidin-2-one;

N-[3,5-Difluoro-4-morpholin-4-yl-6-(2-morpholin-4-yl-ethoxy)-pyridin-2-yl]-N'-(3-methyl-benzylidene)-hydrazine;

N-[3,5-Difluoro-2-morpholin-4-yl-6-(2-morpholin-4-yl-ethoxy)-pyridin-4-yl]-N'-(3-methyl-benzylidene)-hydrazine;

N-(3-methyl-benzylidene)-N'-[4-morpholin-4-yl-6-(2-morpholoine-4-yl-ethoxy)pyridine-2-yl]-hydrazine;

N-(1H-Indol-3-ylmethylene)-N'-[4-morpholin-4-yl-6-(2-morpholin-4-yl-ethoxy)-pyridin-2-yl]-hydrazine;

N-Methyl-N'(3-methyl-benzylidene)-N-[4-morpholin-4-yl-6-(2-morpholin-4-yl-ethoxy)-pyridin-2-yl]-hydrazine;

3-(2-{2-[N'-(3-Methyl-benzylidene)-hydrazino]-6-morpholin-4-yl-pyridin-4-yloxy}-ethyl)-oxazolidin-2-one;

N-Furan-3-ylmethylene-N'-[4-morpholin-4-yl-6-(2-morpholin-4-yl-ethoxy)-pyridin-2-yl]-hydrazine;

4-Methyl-2-{[4-morpholin-4-yl-6-(2-morpholin-4-yl-ethoxy)-pyridin-2-yl]-hydrazonomethyl}-phenylamine;

N-(3-Methyl-benzylidene)-N'-{4-morpholin-4-yl-6-[2-(4-oxy-morpholin-4-yl)-ethoxy]-pyridin-2-yl}-hydrazine;

Dimethyl-(3-{[4-morpholin-4-yl-6-(2-morpholin-4-yl-ethoxy)-pyridin-2-yl]-hydrazonomethyl}-phenyl)-amine;

N-(3-Cyclopropyl-benzylidene)-N'-[4-morpholin-4-yl-6-(2-morpholin-4-yl-ethoxy)-pyridin-2-yl]-hydrazine;

N-(3-Fluoro-benzylidene)-N'-[4-morpholin-4-yl-6-(2-morpholin-4-yl-ethoxy)-pyridin-2-yl]-hydrazine;

N-(3-Chloro-benzylidene)-N'-[4-morpholin-4-yl-6-(2-morpholin-4-yl-ethoxy)-pyridin-2-yl]-hydrazine;

N-(3-Bromo-benzylidene)-N'-[4-morpholin-4-yl-6-(2-morpholin-4-yl-ethoxy)-pyridin-2-yl]-hydrazine;
N-(3-Iodo-benzylidene)-N'-[4-morpholin-4-yl-6-(2-morpholin-4-yl-ethoxy)-pyridin-2-yl]-hydrazine;
N-(3,4-Dimethyl-benzylidene)-N'-[4-morpholin-4-yl-6-(2-morpholin-4-yl-ethoxy)-pyridin-2-yl]-hydrazine;
N-(2,5-Dimethyl-benzylidene)-N'-[4-morpholin-4-yl-6-(2-morpholin-4-yl-ethoxy)-pyridin-2-yl]-hydrazine;
4-Methyl-2-{[4-morpholin-4-yl-6-(2-morpholin-4-yl-ethoxy)-pyridin-2-yl]-hydrazonomethyl}-phenol;
4-Methyl-2-{[4-morpholin-4-yl-6-(2-morpholin-4-yl-ethoxy)-pyridin-2-yl]-hydrazonomethyl}-phenylamine;
Methyl-(4-methyl-2-{[4-morpholin-4-yl-6-(2-morpholin-4-yl-ethoxy)-pyridin-2-yl]-hydrazonomethyl}-phenyl)-amine;
Dimethyl-(4-methyl-2-{[4-morpholin-4-yl-6-(2-morpholin-4-yl-ethoxy)-pyridin-2-yl]-hydrazonomethyl}-phenyl)-amine;
N-Methyl-N-(4-methyl-2-{[4-morpholin-4-yl-6-(2-morpholin-4-yl-ethoxy)-pyridin-2-yl]-hydrazonomethyl}-phenyl)-acetamide;
N-Ethyl-N'-(3-methyl-benzylidene)-N-[4-morpholin-4-yl-6-(2-morpholin-4-yl-ethoxy)-pyridin-2-yl]-hydrazine;
3-{[4-Morpholin-4-yl-6-(2-morpholin-4-yl-ethoxy)-pyridin-2]-hydrazonomethyl}-benzoic acid methyl ester;
3-{[4-Morpholin-4-yl-6-(2-morpholin-4-yl-ethoxy)-pyridin-2-yl]-hydrazonomethyl}-benzoic acid ethyl ester;
3{[4-Morpholin-4-yl-6-(2-morpholin-4-yl-ethoxy)-pyridin-2-yl]-hydrazonomethyl}-benzoic acid isopropyl ester;
3-{[4-Morpholin-4-yl-6-(2-morpholin-4-yl-ethoxy)-pyridin-2-yl]-hydrazonomethyl}-benzoic acid;
3-{[4-Morpholin-4-yl-6-(2-morpholin-4-yl-ethoxy)-pyridin-2-yl]-hydrazonomethyl}-benzamide;
N-Methyl-3-{[4-morpholin-4-yl-6-(2-morpholin-4-yl-ethoxy)-pyridin-2-yl]-hydrazonomethyl}-benzamide;
N-Cyclopropyl-3-{[4-morpholin-4-yl-6-(2-morpholin-4-yl-ethoxy)-pyridin-2-yl]-hydrazonomethyl}-benzamide;
3-Methyl-5-{[4-morpholin-4-yl-6-(2-morpholin-4-yl-ethoxy)-pyridin-2-yl]-hydrazonomethyl}-benzamide;
3-Hydroxymethyl-5-{[4-morpholin-4-yl-6-(2-morpholin-4-yl-ethoxy)-pyridin-2yl]-hydrazonomethyl}-benzamide;
N-(3-Methyl-benzylidene)-N'-[5-methyl-4-morpholin-4-yl-6-(2-morpholin-4-yl-ethoxy)-pyridin-2-yl]-hydrazine;
N-[5-Fluoro-4-morpholin-4-yl-6-(2-morpholin-4-yl-ethoxy)-pyridin-2-yl]-N'-(3-methyl-benzylidene)-hydrazine;
N-[5-Chloro-4-morpholin-4-yl-6-(2-morpholin-4-yl-ethoxy)-pyridin-2-yl]-N'-(3-methyl-benzylidene)-hydrazine;
N-Benzylidene-N'[4-morpholin-4-yl-6-(2-morpholin-4-yl-ethoxy)-pyridin-2-yl]-hydrazine;
N-(3-Methyl-benzylidene)-N'-{6-[2-(4-methyl-piperazin-1-yl)-ethoxy]-4-morpholin-4-yl-pyridin-2-yl}-hydrazine;
N-(3-Methyl-benzylidene)-N'-[4-morpholin-4-yl-6-(2-piperazin-1-yl-ethoxy)-pyridin-2-yl]-hydrazine;
1-[4-(2-{6-[N'-(3-Methyl-benzylidene)-hydrazino]-4-morpholin-4-yl-pyridin-2-yloxy}-ethy)-piperazin-1-yl]-ethanone;
N-{6-[2-(4-Ethyl-piperazin-1-yl)-ethoxy]-4-morpholin-4-yl-pyridin-2-yl}-N'-(3-methyl-benzylidene)-hydrazine;
N-{6-[2-(4-Ethyl-3-methyl-piperazin-1-yl)-ethoxy]-4-morpholin-4-yl-pyridin-2-yl}-N'-(3-methyl-benzylidene)-hydrazine;
N-{6-[2-(4-Ethyl-2-methyl-piperazin-1-yl)-ethoxy]-4-morpholin-4-yl-pyridin-2-yl}-N'-(3-methyl-benzylidene)-hydrazine;
N-{6-[2-(2,6-Dimethyl-morpholin-4-yl)-ethoxy]-4-morpholin-4-yl-pyridin-2-yl}-N'-(3-methyl-benzylidene)-hydrazine;
N-(3-Methyl-benzylidene)-N'-[4-morpholin-4-yl-6-(2-piperidin-1-yl-ethoxy)-pyridin-2-yl]-hydrazine;
N-(3-Methyl-benzylidene)-N'-[4-morpholin-4-yl-6-(2-pyrrolidin-1-yl-ethoxy)-pyridin-2-yl]-hydrazine;
1-(2-{6-[N'-(3-Methyl-benzylidene)-hydrazino]-4-morpholin-4-yl-pyridin-2-yloxy}-ethyl)-pyrrolidin-2-one;
1-(2-{6-[N'-(3-Methyl-benzylidene)-hydrazino]-4-morpholin-4-yl-pyridin-2-yloxy}-ethyl)-pyrrolidine-2,5-dione;
1-(2-{6-[N'-(3-Methyl-benzylidene)-hydrazino]-4-morpholin-4-yl-pyridin-2-yloxy}-ethyl)-imidazolidine-2-thione;
1-Methyl-3-(2-{6-[N'-(3-methyl-benzylidene)-hydrazino]-4-morpholin-4-yl-pyridin-2-yloxy}-ethyl)-imidazolidine-2-thione;
1-(2-{6-[N'-(3-Methyl-benzylidene)-hydrazino]-4-morpholin-4-yl-pyridin-2-yloxy}-ethyl)-pyrrolidin-2-one;
N-[6-(2-[1,3]Dioxolan-2-yl-ethoxy)-4-morpholin-4-yl-pyridin-2-yl]-N'-(3-methyl-benzylidene)-hydrazine;
Dimethylamino-acetic acid 3-{6-[N'-(3-methyl-benzylidene)-hydrazino]-4-morpholin-4-yl-pyridin-2-yl}-propyl ester;
N-(3-Methyl-benzylidene)-N'-[4-morpholin-4-yl-6-(2-pyrazin-2-yl-ethoxy)-pyridin-2-yl]-hydrazine;
N-(3-Methyl-benzylidene)-N'-[4-morpholin-4-yl-6-(2-thiophen-2-yl-ethoxy)-pyridin-2-yl]-hydrazine;
N-(3-Methyl-benzylidene)-N'-[4-morpholin-4-yl-6-(2-thiazol-5-yl-ethoxy)-pyridin-2-yl]-hydrazine;
N-(3-Methyl-benzylidene)-N'-[4-morpholin-4-yl-6-(2-thiazol-2-yl-ethoxy)-pyridin-2-yl]-hydrazine;
N-(3-Methyl-benzylidene)-N'-{6-[2-(2-methyl-thiazol-5-yl)-ethoxy]-4-morpholin-4-yl-pyridin-2-yl}-hydrazine;
N-(3-Methyl-benzylidene)-N'-{6-[2-(2-methyl-oxazol-5-yl)-ethoxy]-4-morpholin-4-yl-pyridin-2-yl}-hydrazine;
N-(3-Methyl-benzylidene)-N'-{6-[2-(2-methyl-3H-imidazol-4-yl)-ethoxy]-4-morpholin-4-yl-pyridin-2-yl}-hydrazine;
N-{6-[2-(2,3-Dimethyl-3H-imidazol-4-yl)-ethoxy]-4-morpholin-4-yl-pyridin-2-yl}-N'-(3-methyl-benzylidene)-hydrazine;
N-[6-(2-Imidazo[1,2-a]pyridin-3-yl-ethoxy)-4-morpholin-4-yl-pyridin-2-yl]-N'-(3-methyl-benzylidene)-hydrazine;
N-{6-[2-(1H-Indol-3-yl)-ethoxy]-4-morpholin-4-yl-pyridin-2-yl}-N'-(3-methyl-benzylidene)-hydrazine;
1-[3-(2-{6-[N'-(3-Methyl-benzylidene)-hydrazino]-4-morpholin-4-yl-pyridin-2-yloxy}-ethyl)-indol-1-yl]-ethanone;
1-[3-(2-{6-[N'-(3-Methyl-benzylidene)-hydrazino]-4-morpholin-4-yl-pyridin-2-yloxy}-ethyl)-pyrrolo[3,2-c]pyridin-1-yl]-ethanone;
4-(3-{6-[N'-(3-Methyl-benzylidene)-hydrazino]-4-morpholin-4-yl-pyridin-2-yloxy}-propyl)-benzoic acid methyl ester;
N-(3-Methyl-benzylidene)-N'-{4-morpholin-4-yl-6-[3-(1-oxy-pyridin-2-yl)-propoxy]-pyridin-2-yl}-hydrazine;

N-[4-Morpholin-4-yl-6-(2-morpholin-4-yl-ethoxy)-pyridin-2-yl]-N'-naphthalen-2-ylmethylene-hydrazine;

N-Benzofuran-5-ylmethylene-N'-[4-morpholin-4-yl-6-(2-morpholin-4-yl-ethoxy)-pyridin-2-yl]-hydrazine;

N-Benzo[b]thiophen-5-ylmethylene-N'-[4-morpholin-4-yl-6-(2-morpholin-4-yl-ethoxy)-pyridin-2-yl]-hydrazine; and N-(3-Methyl-benzylidene)-N'-[4-morpholin-4-yl-6-(2-morpholin-4-yl-ethoxy)-1-oxy-pyridin-2-yl]-hydrazine;

or a pharmaceutically acceptable salt thereof.

* * * * *